US011499160B2

(12) United States Patent
McLean et al.

(10) Patent No.: US 11,499,160 B2
(45) Date of Patent: Nov. 15, 2022

(54) TRANSGENIC PLANT WITH REDUCED FUCOSYLTRANSFERASE AND XYLOSYLTRANSFERASE ACTIVITY

(71) Applicant: PlantForm Corporation, Toronto (CA)

(72) Inventors: Michael D. McLean, Guelph (CA); Zacharie LeBlanc, Guelph (CA)

(73) Assignee: PlantForm Corporation, Toronto (CA)

( * ) Notice: Subject to any disclaimer, the term of this patent is extended or adjusted under 35 U.S.C. 154(b) by 0 days.

(21) Appl. No.: 16/464,818

(22) PCT Filed: Nov. 29, 2017

(86) PCT No.: PCT/CA2017/051432

§ 371 (c)(1),
(2) Date: May 29, 2019

(87) PCT Pub. No.: WO2018/098572

PCT Pub. Date: Jun. 7, 2018

(65) Prior Publication Data

US 2020/0199608 A1 Jun. 25, 2020

Related U.S. Application Data

(60) Provisional application No. 62/428,700, filed on Dec. 1, 2016.

(51) Int. Cl.
*C12N 15/82* (2006.01)
*C12N 9/10* (2006.01)

(52) U.S. Cl.
CPC ....... *C12N 15/8258* (2013.01); *C12N 9/1051* (2013.01); *C12N 9/1077* (2013.01); *C12N 15/8218* (2013.01); *C12N 15/8243* (2013.01); *C12N 15/8245* (2013.01); *C12Y 204/01065* (2013.01)

(58) Field of Classification Search
None
See application file for complete search history.

(56) References Cited

U.S. PATENT DOCUMENTS

| | | | | |
|---|---|---|---|---|
| 7,601,891 | B2 | 10/2009 | Bakker et al. | |
| 7,847,165 | B2 * | 12/2010 | Mallmann .............. | A01H 6/823 800/317.3 |
| 7,884,264 | B2 | 2/2011 | Dickey et al. | |
| 8,193,415 | B2 | 6/2012 | Bakker et al. | |
| 8,309,795 | B2 | 11/2012 | Fujiyama et al. | |
| 8,716,577 | B1 | 5/2014 | Carrigan et al. | |
| 2004/0214273 | A1 | 10/2004 | Fujiyama et al. | |
| 2008/0034456 | A1 | 2/2008 | Fujiyama et al. | |
| 2008/0060092 | A1 | 3/2008 | Dickey et al. | |
| 2010/0154081 | A1 | 6/2010 | Weterings et al. | |
| 2010/0242128 | A1 | 9/2010 | Steinkellner et al. | |
| 2010/0287657 | A1 | 11/2010 | Weterings | |
| 2011/0008837 | A1 | 1/2011 | D-Aoust et al. | |
| 2011/0144308 | A1 | 6/2011 | Dickey et al. | |
| 2012/0083014 | A1 | 4/2012 | Weterings et al. | |
| 2012/0210466 | A9 | 8/2012 | Rouwendal et al. | |
| 2012/0237972 | A1 | 9/2012 | Bakker et al. | |
| 2013/0052683 | A1 | 2/2013 | Weterings et al. | |
| 2013/0164782 | A1 | 6/2013 | Fujiyama et al. | |

FOREIGN PATENT DOCUMENTS

| | | | | |
|---|---|---|---|---|
| CA | 2389217 | A1 | 5/2001 | |
| CA | 2637252 | A1 | 7/2007 | |
| CA | 2637254 | A1 | 7/2007 | |
| CA | 2646583 | A1 | 9/2007 | |
| CA | 2684370 | A1 | 10/2008 | |
| CA | 2687605 | A1 | 11/2008 | |
| CA | 2795379 | A1 | 12/2008 | |
| CA | 2704108 | A1 | 5/2009 | |
| CA | 2759276 | A1 | 10/2010 | |
| CA | 2765287 | A1 | 12/2010 | |
| CA | 2700180 | C | 1/2013 | |
| CA | 2434364 | C | 3/2013 | |
| WO | 2008141806 | A1 | 11/2008 | |
| WO | 2009056155 | A1 | 5/2009 | |
| WO | WO-2009056155 | A1 * | 5/2009 | ......... C12N 15/8246 |
| WO | 2013050155 | A1 | 4/2013 | |
| WO | 2016079739 | A2 | 5/2016 | |

OTHER PUBLICATIONS

Wilson et al. Analysis of Asn-linked glycans from vegetable foodstuffs: widespread occurrence of Lewis a, core alpha1,3-linked fucose and xylose sybstitutions. (2001) Glycobiogy; vol. 11; pp. 261-274 (Year: 2001).*

Bakker et al. An antibody produced in tobacco expressing a hybrid beta-1,4-galactosyltransferase is essentially devoid of plant carbohydrate epitopes. (2006) Proceedings of the National Academy of Sciences; vol. 103; pp. 7577-7582 (Year: 2006).*

Hobbs et al. The effect of T-DNA copy number, position and methylation on reporter gene expression in tobacco transformants. (1990) Plant Molecular Biology; vol. 15; pp. 851-864 (Year: 1990).*

Zhang et al. Generation and molecular characterization of CRISPR/Cas9-induced mutations in 63 immunity-associated genes in tomato reveals specificity and a range of gene modifications. (2020) Frontiers in Plant Science; vol. 11; pp. 1-13 (Year: 2020).*

Hobbs et al., "The effect of T-DNA copy number, position and methylation on reporter gene expression in tobacco transformants", Plant Molecular Biology 15: 851-864, Aug. 1990.

(Continued)

*Primary Examiner* — Cathy Kingdon Worley
(74) *Attorney, Agent, or Firm* — Bereskin & Parr LLP/S.E.N.C.R.L., s.r.l.; Ainslie Parsons

(57) ABSTRACT

A genetically modified plant or plant cell with reduced α1,3-fucosyltransferase and β1,2-xylosyltransferase activity compared to a wild type plant or plant cell, wherein less than 10% of the total glycan on a protein produced by the plant or plant cell is α1,3-fucosylated glycan and less than 3% of the total glycan on the protein is β1,2-xylosylated glycan is provided. In one embodiment, the plant or plant cell comprises three T-DNA insertions expressing five copies of RNAi targeting α1,3-fucosyltranserase and three copies of RNAi targeting β1,2xylosyltransferase.

5 Claims, 14 Drawing Sheets

Specification includes a Sequence Listing.

(56) References Cited

OTHER PUBLICATIONS

Cox, K.M., et al., Glycan optimization of a human monoclonal antibody in the aquatic plant *Lemna minor*. Nat Biotechnol, 2006. 24(12): p. 1591-7.

Strasser, R., et al., Generation of glyco-engineered Nicotiana benthamiana for the production of monoclonal antibodies with a homogeneous human-like N-glycan structure. Plant Biotechnol J, 2008. 6(4): p. 392-402.

* cited by examiner (A)

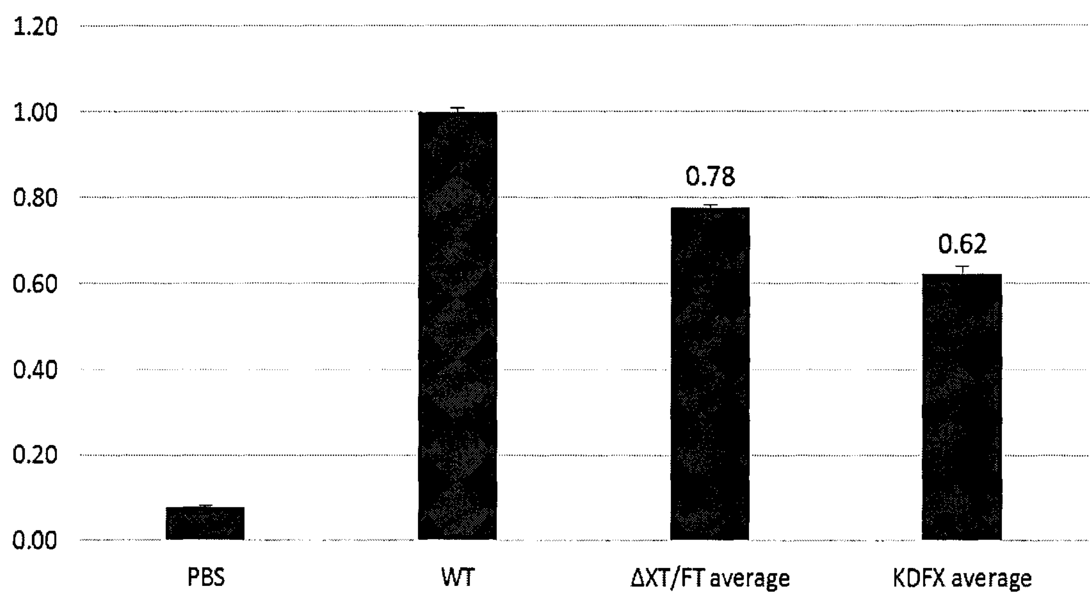
| Sample set | Mean | Standard Error |
|---|---|---|
| PBS | 0.08 | 0.005 |
| WT | 1.00 | 0.008 |
| KDFX1 | 0.47 | 0.002 |
| ΔXT/FT average | 0.78 | 0.007 |
| KDFX T5 average | 0.62 | 0.019 |
(B)
Figure 8 con't

KDFX T-DNA insertions
Insert 1
Sol genomics scaffold: Niben101Scf00158
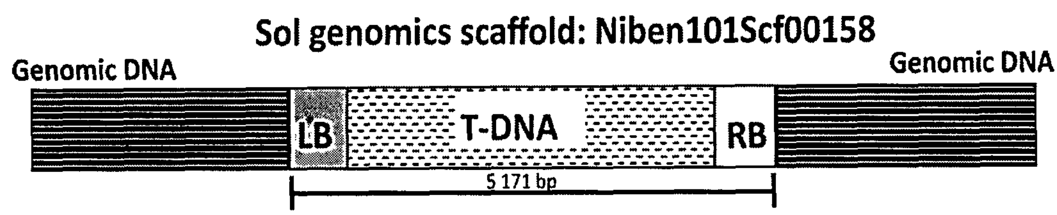
Insert 2
Sol genomics scaffold: Niben101Scf03778
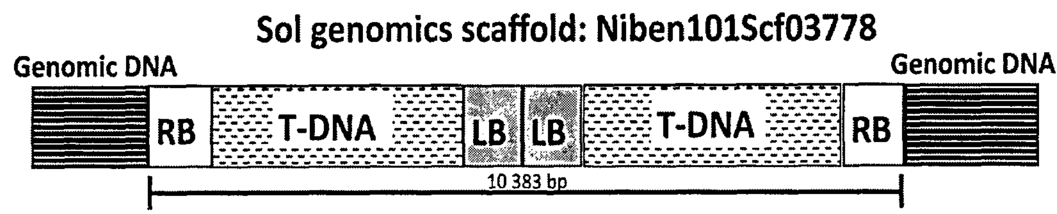
Insert 3
Sol genomics scaffold: Niben101Scf02246
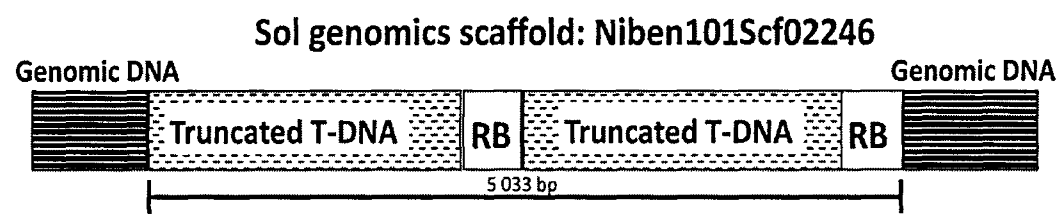
Figure 9

```
                                                                                         Right Border
Insert1KDFX          -50     ACTTACAAATTTAGTTTCATACTTAATGATAAAGCTACTTTTAATTAGCTTAGTTTAAACTGAAGGCGGGAAACGACAATCTTTAA SEQ ID NO: 18
Niben101Scf00158  392402     ACTTACAAATTTAGTTTCATACTTAATGATAAAGCTACTTTTAATTAGCT------------------------------------ SEQ ID NO: 19

Insert1KDFX           37     TTAATTAAGGCCGGCCAT-SEQ ID NO: 20--5071 bp----------------------TCGACGGCGCGCCA SEQ ID NO: 21
Niben101Scf00158  392452     --------------AAGTCAAATATGCTCTAGTAGTAGACTTGTCCAAAGTCTATATAACCAATC------------- SEQ ID NO: 22
                                        Left Border
Insert1KDFX         5135     TTAATCAGTACATTAAAAACGTCCGCAATGTGTTATTAAATGAACATGTGGTATAGAAAATGTCATTCATTTTTCTTTTAAACATA SEQ ID NO: 23
Niben101Scf00158  392503     ------------------------------------TAAATGAACATGTGGTATAGAAAATGTCATTCATTTTTCTTTTAAACATA SEQ ID NO: 24
```

```
                                                                                         Right Border
Insert2KDFX          -50     CTTATGTCTAATTTCAACTTTGATTATTTTTCACGTTTTTCTTTAACCTTCAAACACTGATAGTTTAAACTGAAGGCGGGAAACG SEQ ID NO: 25
Niben101Scf03778   97835     CTTATGTCTAATTTCAACTTTGATTATTTTTCACGTTTTTCTTTAACCT------------------------------------ SEQ ID NO: 26

Insert2KDFX           37     ACAATCTTTAATTA--SEQ ID NO: 27-----------10273 bp-------------------GCCGGCCTTAATTA SEQ ID NO: 28
Niben101Scf03778   97885     --------------TTTGTTTTTGGTACGTTCAGATTGCTTTC------------------------------------- SEQ ID NO: 29
                                        Right Border
Insert2KDFX        10337     AAGATTGTCGTTTCCCGCCTTCAGTTTAAACTATCACAAGTTCTAGTCAAAGCATTGATTGGAATAGATCAAGGTGACCAATTGGA SEQ ID NO: 30
Niben101Scf03778   97914     ------------------------------------CAAGTTCTAGTCAAAGCATTGATTGGAATAGATCAAGGTGACCAATTGGA SEQ ID NO: 31
```

```
                                                                                         Right Border
Insert3KDFX          -50     GATTGGGACAAAAAAATCTGGTGAATCTGGGAGCAAAGAGTCAGCTGGTTGTAGTTTAAACTGAAGGCGGGAAACGACAATCTTTAA SEQ ID NO: 32
Niben101Scf02246  166903     GATTGGGACAAAAAAATCTGGTGAATCTGGGAGCAAAGAGTCAGCTGGTTG------------------------------------ SEQ ID NO: 33
                                                                                                    XylT Intron
Insert3KDFX           37     TTAAGGCCGGCCAT--SEQ ID NO: 34-----------4933 bp-------------------GGGAAAGTCCAGTT SEQ ID NO: 35
Niben101Scf02246  166953     --------------GGACAACAAGATCACTCAGAAAGCGTCAGCAGGAAACTCCTCTGCATGGAATAGCAAATCTGCAGTC----- SEQ ID NO: 36
                                        XylT Intron
Insert3KDFX         4997     TAGACTTGTAGTTAGTTACTCTTCGTTATAGGATTTGAACAAGATGCCAATGGGAAAAATCAATGGAGTGGTAAAAGAACTTCAGA SEQ ID NO: 37
Niben101Scf02246  167021     ------------------------------------GAACAAGATGCCAATGGGAAAAATCAATGGAGTGGTAAAAGAACTTCAGA SEQ ID NO: 38
```

Figure 10

TRANSGENIC PLANT WITH REDUCED FUCOSYLTRANSFERASE AND XYLOSYLTRANSFERASE ACTIVITY

RELATED APPLICATIONS

This disclosure is a national phase entry of PCT/CA2017/051432 filed Nov. 29, 2017 (which designates the U.S.), which claims the benefit of priority to U.S. provisional application No. 62/428,700 filed Dec. 1, 2016, which is incorporated herein by reference in its entirety.

INCORPORATION OF SEQUENCE LISTING

A computer readable form of the Sequence Listing "20436-P51661US01_SequenceListing.txt" (50,688 bytes), submitted via EFS-WEB and created amended on Jan. 24, 2020, is herein incorporated by reference.

FIELD

The present disclosure relates to a transgenic host plant for protein production wherein the plant has reduced α1,3-fucosyltransferase and β1,2-xylosyltransferase activity.

BACKGROUND

A great challenge present in the production of therapeutic proteins in plant systems is ensuring that these products are not immunogenic in humans. Plant systems produce proteins carrying N-linked core α1,3-fucose and N-linked core β1,2-xylose which have been found to induce an immunogenic response in mice and rats (Bardor et al., 2002).

The first evidence of a human IgE-based allergic response to plant proteins bearing α1,3fucose- and β1,2-xylose-linked glycans was published in 1996 (Garcia-Casado et al. 1996). Prior, the specific cause of mammalian hypersensitivity to plant-derived glycoproteins was unknown. In this work, Garcia-Casado and colleagues demonstrated that the specific IgE response to plant-derived BMAI-1 was lost upon deglycosylation, and further that IgE antibodies from these patients are able to recognize other unrelated glycoproteins if those glycoproteins carry N-linked α1,3-fucose- or β1,2-xylose-containing complex glycans.

IgE antibodies directed towards fucose- and xylose-containing glycans are also cross-reactive to invertebrate animals (Aalberse et al. 1981; Aalberse and van Ree 1997). Approximately 28% of individuals allergic to honeybee venom display a strong IgE-based reaction to the α1,3-fucose-linked N-glycan on phospholipase $A_2$ (Tretter et al. 1993).

Several studies have published results from intravenous administration of plant-derived proteins. The first examples describe Elelyso (*Taliglucerase alfa*), a commercially available treatment for Gaucher disease. Published reports from Phase I (Aviezer et al. 2009) and Phase III (Zimran et al. 2011) clinical trials do not indicate a specific anti-α1,3-fucose- and/or β1,2-xylose immune response. Both studies support the safety and efficacy of the plant-produced *Taliglucerase alfa*. A second example examines the administration of a plant-produced influenza virus-like particle vaccine (Ward et al. 2014). In this study, 280 subjects received either one or two doses of plant-produce vaccine. Forty individuals had preexisting plant allergies. No subjects developed allergic or hypersensitivity symptoms. Approximately one-third developed transient IgG and/or IgE responses to plant glyco-epitopes, but without clinical symptoms.

Evidence from plant-produced *Taliglucerase alfa* and virus-like particle studies suggest that intravenous administration of proteins carrying fucose and xylose do not elicit an IgE hypersensitivity response. However, there are several unanswered questions. First, it is not currently known if the response to fucose and/or xylose linked to a monoclonal antibody (mAb) will be more severe than those responses to *Taliglucerase alfa* and the virus-like particles. Second, the minor elevated IgG and IgE serum levels noted (although not categorized as a "response") may negatively influence the pharmacokinetics and efficacy of a mAb, specifically in comparison to the innovator drug (i.e. development of a plant-produced biosimilar). Third, repeated dosing over time of a mAb with plant-specific glycans may elicit a slow adaptive immune response, and either reduce efficacy or cause an acute response at some point after administration. Finally, with the goal of making biosimilar products, the glycans recombinant proteins should resemble the innovator products as closely as possible.

Strasser et al. (2008) developed a stable line of transgenic *N. benthamiana* plants, called ΔXT/FT, with reduced xylosylation and fucosylsation. Although they report that tryptic glycopeptides of mAb 2G12 analyzed by LC-ESI-MS are <1% GnGnF, <1% GnGnX and <1% GnGnFX (Table 1 of Strasser et al), they show release of considerably more GnGnF glycans from endogenous plant proteins by MALDI-TOF/TOF MS (FIG. 2D of Strasser et al).

The development of ΔXT/FT (ΔFX) by Strasser et al (2008) was accomplished by a reduction of expression of xylosyl transferase (XylT) and fucosyl transferase (FucT) at the transcript level using RNA interference (RNAi). This technique involves the in vivo creation of an RNA hairpin which is then processed into 21-24 bp fragments which are then used to target endogenous transcripts. RNAi knockdown efficiency relies heavily on complementarity of a selected sequence to the targeted transcript. Strasser et al (2008) created two RNAi constructs: one based on the sequence of a single fucosyltransferase gene (FucT); the other, on the sequence of a single xylosyltransferase gene (XylT) from *Nicotiana benthamiana*. Two transgenic plant lines were developed: line 14, named ΔFT; line 1, named ΔXT. These two lines were bred to homozygosity and cross-pollinated. Progeny of this cross were analyzed by Western blot using anti-HRP antiserum. Several plantlets of the $F_1$ generation showed no anti-HRP staining and one of these was grown to maturity and named ΔXT/FT.

However, given the base levels of β1,2-xylosylation and α1,3-fucosylsation still present in ΔXT/FT, a need remains for an improved version of a *Nicotiana benthamiana* host plant demonstrating even lower amounts of β1,2-xylosylation and α1,3-fucosylsation for commercial production of proteins such as antibodies to be used in humans.

SUMMARY

The present disclosure describes a new genetically modified *N. benthamiana* plant that contains three transgenic insertion loci, in total expressing five copies of α1,3-fucosyltranserase RNAi and 3 copies of β1,2xylosyltransferase RNAi. This stable, transgenic plant line produces glycoproteins with only a trace amount of β1,2-xylosylated glycan and about 2% α1,3-fucosylated glycan out of the total glycan species.

Accordingly, the present disclosure provides a genetically modified plant or plant cell with reduced α1,3-fucosyltransferase and β1,2-xylosyltransferase activity compared to a wild type plant or plant cell, wherein less than 10% of the total glycan on a protein produced by the plant or plant cell is α1,3-fucosylated glycan.

In one embodiment, less than 3% of the total glycan on the protein is β1,2-xylosylated glycan.

In another embodiment, less than 4% of the total glycan on the protein is α1,3-fucosylated glycan and less than 1% of the total glycan on the protein is β1,2-xylosylated glycan.

In another embodiment, the genetically modified plant or plant cell comprises at least two T-DNA insertions.

In another embodiment, the at least two T-DNA insertions express three copies of RNAi targeting α1,3-fucosyltranserase and three copies of RNAi targeting β1,2xylosyltransferase.

In another embodiment, the genetically modified plant or plant cell comprises three T-DNA insertions.

In another embodiment, the at least three T-DNA insertions express five copies of RNAi targeting α1,3-fucosyltranserase and three copies of RNAi targeting β1,2xylosyltransferase.

In another embodiment, the three T-DNA insertions comprise SEQ ID NO: 15, 16 and 17, or sequences having at least 75% sequence identity to SEQ ID NO: 15, 16 and 17, respectively. In another embodiment, the plant or plant cell is homozygous for each of the three T-DNA insertions.

In another embodiment, the plant or plant cell is a *Nicotiana* plant, optionally a *Nicotiana benthamiana* plant or plant cell.

The disclosure also provides a method of producing a protein in a plant, comprising:

(a) introducing a nucleic acid molecule encoding the protein into a plant or plant cell described herein and
(b) growing the plant or plant cell to obtain a plant that expresses the protein, wherein less than 10% of the total glycan on the protein is α1,3-fucosylated glycan and less than 3% of the total glycan on the protein is β1,2-xylosylated glycan.

In one embodiment, less than 4% of the total glycan on the protein is α1,3-fucosylated glycan and less than 1% of the total glycan on the protein is β1,2-xylosylated glycan.

In another embodiment, the protein is a glycoprotein.

In another embodiment, the protein is an antibody.

The disclosure also provides a protein produced by the plant or plant cell described hereon, or by the method described herein.

Other features and advantages of the present disclosure will become apparent from the following detailed description. It should be understood, however, that the detailed description and the specific Example while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

FIG. 9 shows a cartoon modelling of KDFX T-DNA insertions 1 to 3. *N. benthamiana* genomic DNA is indicated by horizontal lined boxes, T-DNA right and left borders are indicated by gray boxes and elements in between T-DNA left and right borders are indicated by dashed boxes. Sizes are not to scale. End sequences for each insertion are given in FIG. 10. (i) Insert 1 is a single, complete T-DNA insertion. Although the T-DNA region of pPFC1408 given in FIG. 2 is 5418 base pairs, Insert 1 did not incorporate 117 base pairs from the left side of the LB sequence and likewise did not incorporate 130 base pairs from the right side of the RB sequence. (ii) Insert 2 is a double insertion consisting of two complete T-DNA regions, each of similar size to that of Insert 1. Note that the double insertions have opposite orientations. (iii) Insert 3 is a double insertion consisting of two truncated T-DNA regions. The truncations are similar in that they both involve deletions of more than 2.7 kilobase pairs of DNA sequence from and including the entire LB.

FIG. 10 shows an alignment of KDFX TDNA Insertion sites with corresponding *Nicotiana benthamiana* genomic DNA sequences from the Sol Genomics *N. benthamiana* genome sequencing project. Black boxes indicate genomic DNA common to both *N. benthamiana* genomic DNA and the KDFX line. Insert number and Sol Genomics scaffold sequence number are given on the far left; numbers to the right of these indicate T-DNA insert nucleotide number or genomic scaffold nucleotide number. In KDFX each T-DNA insertion occurs between the black boxes, flanking T-DNA LB and RB elements are indicated by white boxes with the element description written above. During transformation, insertion of T-DNA sequences into the KDFX line caused the deletion of native sequences at the locus of insertion, these deleted sequences are indicated by grey boxes. Absence of the sequences indicated by boxes in the KDFX line is one indicator of homozygosity for the T-DNA insert at the corresponding locus.

DETAILED DESCRIPTION

Figure 1:
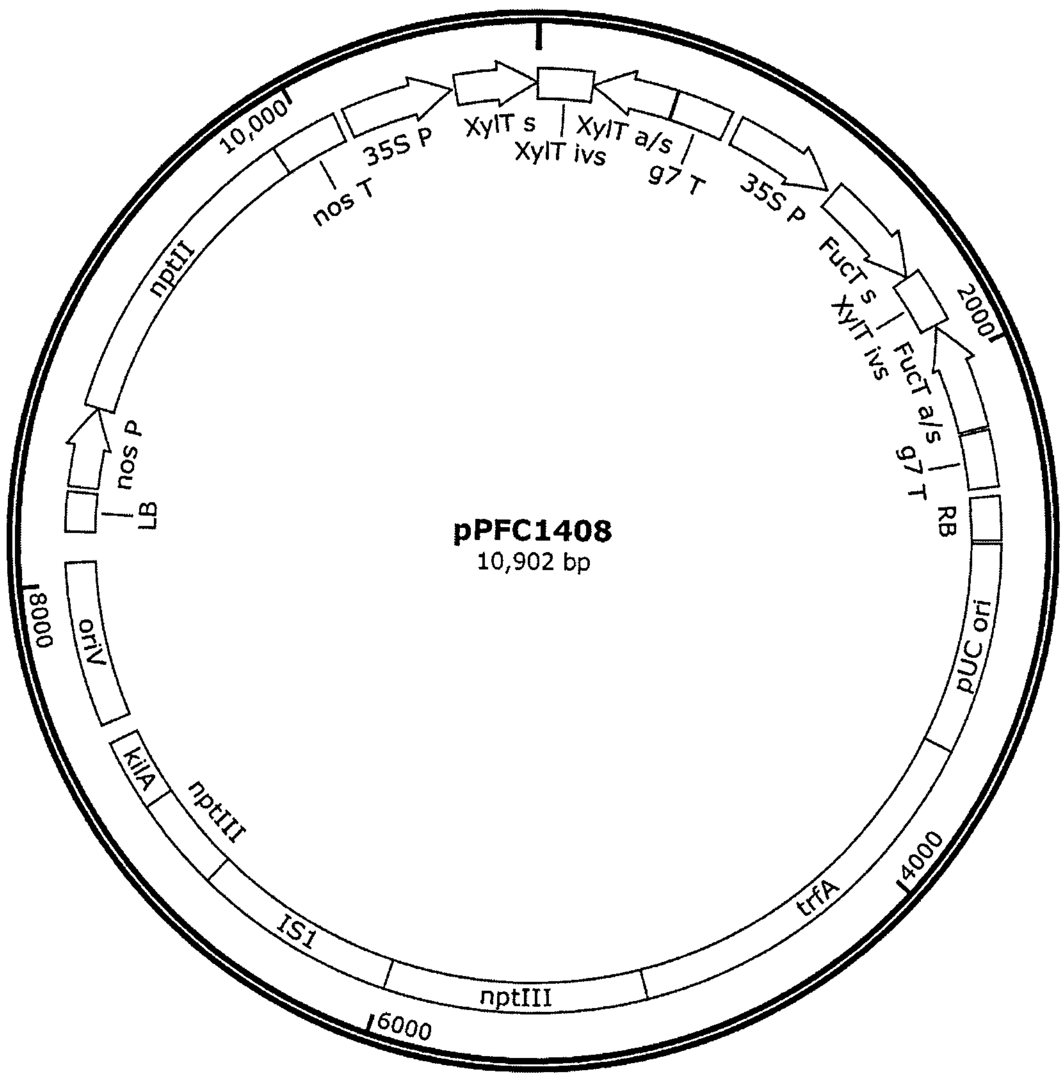
FIG. 1 shows a schematic map of plasmid pPFC1408. LB, left border of T-DNA region; Nos P, nopaline synthase promoter; nptII, neomycin phosphotransferase II coding sequence; Nos T, nopaline synthase terminator; 35S P, cauliflower mosaic virus 35S promoter; XylT s, sense sequence of xylosyltransferase gene; XylT ivs, xylosyltransferase gene intervening sequence; XylT a/s, antisense sequence of xylosyltransferase gene; g7 T, terminator sequence of *Agrobacterium tumefaciens* gene 7; FucT s, sense sequence of fucosyltransferase gene; FucT a/s, antisense sequence of fucosyltransferase gene; RB, right border of T-DNA region; pUC ori, origin of replication sequence from plasmid pUC18; trfA, trfA gene of plasmid RK2; nptIII, neomycin phosphotransferase III gene; kilA, kilA gene of plasmid RK2; oriV, replication origin of plasmid RK2.

The present disclosure describes a new genetically modified *N. benthamiana* plant that contains three transgenic insertion loci, in total expressing five copies of α1,3-fucosyltranserase RNAi and three copies of β1,2xylosyltransferase RNAi. This stable, transgenic plant line produces glycoproteins with only a trace amount of β1,2-xylosylated glycan and about 3% α1,3-fucosylated glycan out of the total glycan species.

Compositions of Matter

Plants and Plant Cells

Accordingly, the disclosure provides a genetically modified plant, or plant cell with reduced endogenous α1,3-fucosyltransferase and β1,2-xylosyltransferase activity compared to a wild type plant or plant cell.

Glycosylation is one of the most significant post-translational modifications of eukaryotic proteins. Glycan functions are often dependent on the structure of the oligosaccharide. Oligosaccharides are covalently attached to proteins primarily through two structural motifs: attached to the amide group of an asparagine, referred to as "N-linked glycans," or attached to the hydroxyl group on serine or threonine, referred to as "O-linked glycans".

Plant glycans carry N-linked β1,2-xylose and core α1,3-fucose, which are absent in mammals. β1,2xylosyltransferase and α1,3-fucosyltranserase are the enzymes responsible for β1,2-xylosylation and α1,3-fucosylation, respectively. Accordingly, the term "β1,2-xylosyltransferase activity" refers to the addition of a β1,2-xylose to an N-glycan and the term α1,3-fucosyltransferase activity" refers to the addition of an α1,3-fucose to a core glycan.

As used herein, the term "XylT" refers to genes encoding β(1,2)-xylosyltransferase and includes isoforms, analogs, variants or functional derivatives thereof. The term also includes sequences that have been modified from any of the known published sequences of XylT/β(1,2)-xylosyltransferase genes or proteins. The XylT gene or protein may have any of the known published sequences for XylT which can be obtained from public sources such as GenBank. In *N. benthamiana*, β(1,2)-xylosyltransferase (XylT) genes include XylT2 and XylT1 (GenBank Accessions: EF562628.1 and EF562629.1 respectively). The aforementioned sequences are incorporated herein by reference. As used herein, the term "FucT" refers to genes encoding α1,3-fucosyltranserase and includes isoforms, analogs, variants or functional derivatives thereof. The term also includes sequences that have been modified from any of the known published sequences of FucT/α1,3-fucosyltranserase genes or proteins. The FucT gene or protein may have any of the known published sequences for FucT which can be obtained from public sources such as GenBank. In *N. benthamiana,* α1,3-fucosyltranserase (FucT) genes include FucT1 (GenBank Accession: EF562630.1). In addition, analysis of the Sol Genomics Network draft of the *N. benthamiana* genome (available online at solgenomics.net; Fernandez-Pozo et al., 2014), reveals the presence of 2 additional putative FucT homologues for a total of 4 predicted FucT cNDA sequences in the draft genome: Niben101Scf02631g00007.1; Niben101Scf01272g00014.1; Niben101Scf05494g01011.1 and Niben101Scf05447g03009.1. Niben101Scf17626g 00001.1 is likely a FucT pseudogene. The aforementioned sequences are incorporated herein by reference.

In one embodiment of the present disclosure, endogenous α1,3-fucosyltransferase activity is reduced by at least 5%, 10%, 25%, 50%, 75% or 100% compared to a wild type plant or plant cell. In another embodiment, the plant or plant cell has no detectable α1,3-fucosyltransferase activity.

In another embodiment, endogenous β1,2-xylosyltransferase activity is reduced by at least 5%, 10%, 25%, 50%, 75% or 100% compared to a wild type plant or plant cell. In another embodiment, the plant or plant cell has no detectable β1,2-xylosyltransferase activity.

As used herein, the term "wild type" refers to a plant or plant cell which is not genetically modified. Optionally, a wild type plant or plant cell has normal (non-modified), endogenous expression levels of α1,3-fucosyltransferase and/or β1,2-xylosyltransferase genes or proteins.

As used herein, the term "plant" includes a plant cell and a plant part. The term "plant part" refers to any part of a plant including but not limited to the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like.

Endogenous α1,3-fucosyltransferase and β1,2-xylosyltransferase activity can be reduced by any method known in the art. In one embodiment of the present disclosure, endogenous α1,3-fucosyltransferase and β1,2-xylosyltransferase activity is reduced through the use of interfering RNA (RNAi) targeting genes encoding α1,3-fucosyltransferase and β1,2-xylosyltransferase, respectively.

RNAi techniques involve stable transformation using RNA interference (RNAi) plasmid constructs (Helliwell and Waterhouse, 2005). Such plasm ids (also referred to herein as vectors) are composed of the target gene or a fragment of the target gene to be silenced. The RNAi construct driven by a suitable promoter, for example, the Cauliflower mosaic virus (CaMV) 35S promoter, is integrated into the plant genome at an insertion locus (also referred to herein as a T-DNA (transfer DNA) insertion locus) and subsequent transcription of the transgene leads to an RNA molecule that folds back on itself to form a double-stranded hairpin RNA. This double-stranded RNA structure is recognized by the plant and cut into small RNAs (about 21-24 bp fragments) called small interfering RNAs (siRNAs). siRNAs associate with a protein complex (RISC) which goes on to direct degradation of the mRNA for the target gene.

As used herein, the term "RNAi cassette" or "RNAi expression cassette" or "RNAi knockdown cassette" refers to a single, operably linked set of regulatory elements that includes a promoter, a sense sequence of the target gene, an antisense sequence of the target gene, a sequence between the sense sequence and the antisense sequence, which, in the methods described herein, is optionally an intervening sequence from the XylT gene and a terminator sequence.

A single vector may contain one, two or multiple RNAi cassettes. For example, plasmid pPFC1408 as described herein includes two RNAi cassettes—one targeting XylT/β1,2-xylosyltransferase and one targeting FucT/α1,3-fucosyltransferase.

Figure 2:
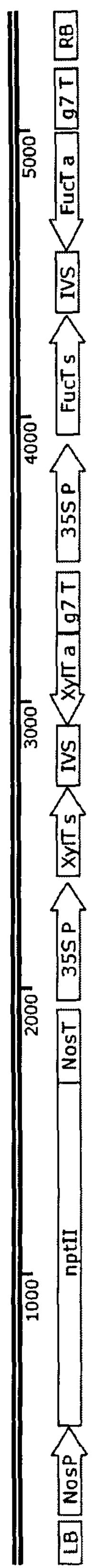
FIG. 2 shows a schematic map of the T-DNA region from plasmid pPFC1408. LB, left border of T-DNA region; Nos P, nopaline synthase promoter; nptII, neomycin phosphotransferase II coding sequence; Nos T, nopaline synthase terminator; 35S P, cauliflower mosaic virus 35S promoter; XylT s, sense sequence of xylosyltransferase gene; IVS, xylosyltransferase gene intervening sequence; XylT a, antisense sequence of xylosyltransferase gene; g7 T, terminator sequence of *Agrobacterium tumefaciens* gene 7; FucT s, sense sequence of fucosyltransferase gene; FucT a, antisense sequence of fucosyltransferase gene; RB, right border of T-DNA region. The entire size of the T-DNA region of pPFC1408, including LB and RB sequences, is 5418 base pairs.

As used herein, the term "T-DNA" refers to the entire nucleic acid molecule that is integrated into the plant genome. For example, FIG. 2 depicts a schematic map of the T-DNA region from plasmid pPFC1408, including a first RNAi cassette targeting XylT and a second RNAi cassette targeting FucT.

As known in the art, T-DNA expressed from a plasmid may integrate into a genome at one, two or multiple sites. These sites are referred to herein as T-DNA insertion loci or T-DNA insertion sites. The nucleic acid sequence inserted at the T-DNA insertion locus is referred to as a "T-DNA insertion". For example, the genome of the genetically modified plant described herein includes three T-DNA insertions as depicted in FIG. 9.

T-DNA insertions may comprise single, double or multiple insertions of various orientations. In other words, a T-DNA insertion can express one, two, three or more copies of RNAi targeting a specific gene. For example, as depicted in FIG. 9, "Insert 2" is a double insertion that expresses two copies of RNAi targeting XylT (i.e., β1,2xylosyltransferase) and two copies of RNAi targeting FucT (i.e., α1,3-fucosyltranserase).

In addition, the T-DNA insertions can be complete or incomplete. In a complete T-DNA insertion, the entire T-DNA region from the plasmid is inserted into the plant genome. In an incomplete insertion, only a portion of the T-DNA region from the plasmid is inserted into the plant genome (also known as a truncated T-DNA insertion). For example, as depicted in FIG. 9, insert 3 is an incomplete T-DNA insertion.

Accordingly, in one embodiment, a T-DNA insertion comprises a complete FucT-targeting RNAi sequence, meaning that the entire RNAi cassette targeting FucT is inserted at the insertion locus. In another embodiment, a T-DNA insertion comprises a complete XylT-targeting RNAi sequence, meaning that the entire RNAi cassette targeting XylT is inserted at the insertion locus.

Figure 12:
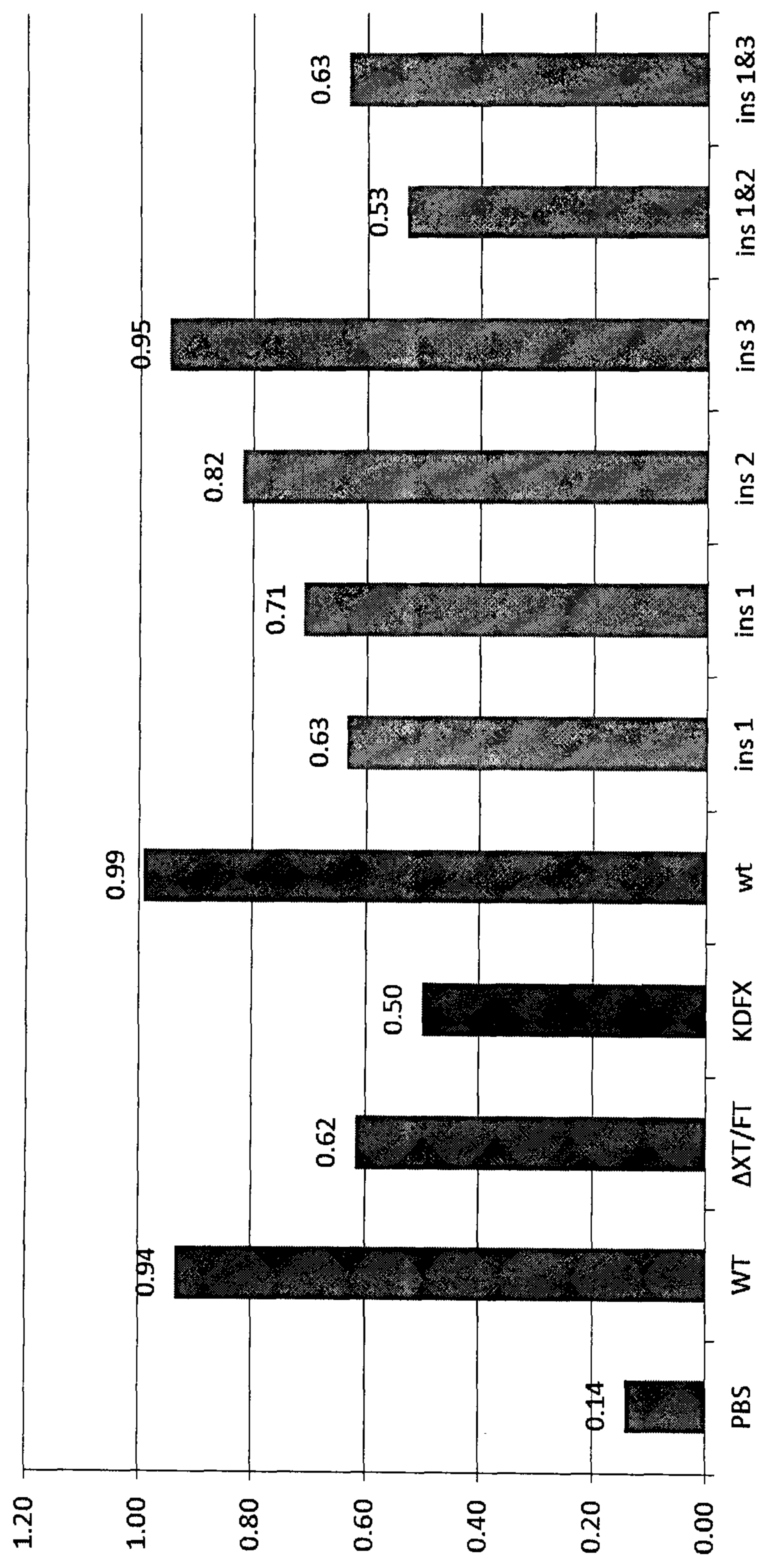
FIG. 12 shows anti-HRP ELISA on total soluble protein extracts from KDFX T-DNA locus segregants. First generation transgenic plants from primary transgenic plant #17 (i.e., plant $T_0$-17) were screened with the three T-DNA locus-specific PCR assays (shown above) for segregants homozygous at only 1 or 2 T-DNA loci, and total soluble protein extracts of these and control plants were subjected to anti-HRP ELISA. X-axis shows controls in upper case: PBS (phosphate-buffered saline control), WT (TW-16 wild-type plant), ΔXT/FT, line of Strasser et al. (2008)), KDFX (progeny plant from $T_5$ generation plant 17-7-26-9-3); segregants in lower case: wt (wild-type segregant, that contains no T-DNA inserts), ins 1 (T-DNA Insert 1 homozygote; note that 2 of these plants were identified in the PCR screen), ins 2 (T-DNA Insert 2 homozygote), ins 3 (T-DNA Insert 3 homozygote), ins 1&2 (T-DNA Insert 1 and Insert 2 homozygote), ins 1&3 (T-DNA Insert 1 and Insert 3 homozygote). Note that among the 3 individual T-DNA insertion loci, Insert 1 provides the best knock-down of xylosyltransferase and fucocyltransferase activities, while Insert 3 provides very little knock-down of xylosyltransferase and fucocyltransferase activities.

The present disclosure shows that T-DNA insertions 1 and 2 (see FIG. 9), which provide three complete FucT targeting RNAi genes and three complete XylT-targeting RNAi genes confer improved RNAi knockout of FucT and XylT activities over the prior art plant lines (FIG. 12).

Accordingly, in one embodiment of the present disclosure, the genetically modified plant or plant cell expresses at least three copies of RNAi targeting α1,3-fucosyltranserase and at least three copies of RNAi targeting β1,2xylosyltransferase. In another embodiment, the genetically modified plant or plant cell expresses five copies of RNAi targeting α1,3-fucosyltranserase and three copies of RNAi targeting β1,2xylosyltransferase.

Insertions 1, 2 and 3 shown in FIG. 9 have been sequenced. Thus, in another embodiment, the three T-DNA insertions comprise SEQ ID NO: 15, 16 and 17, respectively, or sequences having at least 75%, 80%, 85%, 90%, 95% or 99% sequence identity to SEQ ID NO: 15, 16 and 17, respectively.

Sequences of T-DNA insertion loci 1-3 in the KDFX line have been determined by Illumina sequencing of KDFX line 17-7-26:T2. Insertion loci are defined here by their localization in the Sol Genomics draft *N. benthamiana* genome assembly which places inserts 1-3 at Niben101Scf00158 (392453-392503), Niben101Scf03778(97886-97914) and Niben101Scf02246(166954-167021), respectively (FIG. 10).

As is well known in the art, T-DNA insertions can be homozygous (plant has two copies of the T-DNA insertion) or heterozygous (plant has one copy of the T-DNA insertion). In one embodiment of the present disclosure, the plant, plant part or plant cell is homozygous for each of the T-DNA insertions.

In another embodiment of the present disclosure, the plant or plant cell is a *Nicotiana* plant or plant cell, optionally a *Nicotiana benthamiana* plant or plant cell.

As used herein, the term "nucleic acid molecule" means a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases.

Examples of such modified bases include aza and deaza adenine, guanine, cytosine, thymidine and uracil; and xanthine and hypoxanthine.

As used herein, the term "vector" means a nucleic acid molecule, such as a plasmid, comprising regulatory elements and a site for introducing transgenic DNA, which is used to introduce said transgenic DNA into a plant or plant cell. The transgenic DNA can comprise a target gene or a fragment of the target gene to be silenced via RNAi. In one embodiment, the vector is pPFC1408 as depicted in FIG. 1. In other embodiments, the transgenic DNA can encode a heterologous protein, which can be expressed in and isolated from a plant or plant cell.

As used here, the term "sequence identity" refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions multiplied by 100%). In one embodiment, the two sequences are the same length. The determination of percent identity between two sequences can also be accomplished using a mathematical algorithm. One non-limiting example of a mathematical algorithm utilized for the comparison of two sequences is the algorithm of Karlin and Altschul (1990), modified as in Karlin and Altschul (1993). Such an algorithm is incorporated into the NBLAST and XBLAST programs of Altschul et al. (1990). BLAST nucleotide searches can be performed with the NBLAST nucleotide program parameters set, e.g., for score=100, wordlength=12 to obtain nucleotide sequences homologous to a nucleic acid molecules of the present disclosure. BLAST protein searches can be performed with the XBLAST program parameters set, e.g., to score-50, wordlength=3 to obtain amino acid sequences homologous to a protein molecule of the present disclosure. To obtain gapped alignments for comparison purposes, Gapped BLAST can be utilized as described in Altschul et al. (1997). Alternatively, PSI-BLAST can be used to perform an iterated search which detects distant relationships between molecules (Altschul et al., 1997). When utilizing BLAST, Gapped BLAST, and PSI-Blast programs, the default parameters of the respective programs (e.g., of XBLAST and NBLAST) can be used (see, e.g., the NCBI website). Another non-limiting example of a mathematical algorithm utilized for the comparison of sequences is the algorithm of Myers and Miller (1988). Such an algorithm is incorporated in the ALIGN program (version 2.0) which is part of the Genetics Computer Group (GCG) sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

The sequences of the present disclosure may be at least 75%, 80%, 85%, 90%, 95% or 99% identical to the sequences set out within. Importantly, the substantially identical sequences retain the activity and specificity of the reference sequence.

Proteins

Disclosed herein is a plant or plant cell that produces a protein having reduced levels of plant-specific glycans, optionally less than 10%, 9%, 8%, 7%, 6%, 5%, 4%, 3%, 2% or 1% plant-specific glycans. As used herein, the term "plant-specific glycans" refers to glycans normally present on proteins produced by plants but not present on proteins produced by mammals such as humans. Plant specific glycans include both β1,2-xylose and α1,3-fucose-linked glycans.

In one embodiment of the present disclosure, less than 10%, 9%, 8%, 7%, 6%, 5%, 4%, 3%, 2% or 1% of the total glycan on a protein produced by the plant or plant cell described herein is α1,3-fucosylated glycan. In another embodiment, the protein produced by the plant or plant cell has a trace amount of α1,3-fucosylated glycan, a non-measurable or non-detectable amount of α1,3-fucosylated glycan or a negligible amount of α1,3-fucosylated glycan. α1,3-fucosylated glycan may be measured or detected by any of the methods described herein.

In another embodiment of the present disclosure, less than 10%, 9%, 8%, 7%, 6%, 5%, 4%, 3%, 2% or 1% of the total glycan on a protein produced by the plant or plant cell described herein is β1,2-xylosylated glycan. In another embodiment, the protein produced by the plant or plant cell has a trace amount of β1,2-xylosylated glycan, a non-measurable or non-detectable amount of β1,2-xylosylated or a negligible amount of β1,2-xylosylated. β1,2-xylosylated glycan may be measured or detected by any of the methods described herein.

In one embodiment, the protein is a glycoprotein. As used herein, the term "glycoprotein" refers to any protein that has at least one carbohydrate group attached to the polypeptide chain.

As used herein, "total glycan on a protein" refers to all the glycan species on the protein and may also be referred to as the "total glycan pool". Total glycan can be released from a protein through enzymatic or chemical means, as known in the art.

In another embodiment, a protein produced by the plant or plant cell described herein has a "humanized glycosylation profile". As used herein, the term "glycosylation profile" means the characteristic "fingerprint" of the representative N-glycan species that have been released from a glycoprotein composition or glycoprotein product, either enzymatically or chemically, and then analyzed for their carbohydrate structure, for example, using LC-HPLC, or MALDI-TOF/TOF MS, and the like. See, for example, the review in Morelle and Michalski (2005). As used herein, the term "humanized glycosylation profile" means a glycosylation profile which contains <5% plant-specific glycans (β1,2-xylose or α1,3-fucose).

Levels of β1,2-xylosylated glycan and/or α1,3-fucosylated glycan can be determined by any method known in the art. For example, antibodies raised against horseradish peroxidase (HRP) display strong reactivity to xylose and plant-specific fucose linkages. Accordingly, in one embodiment, antibodies raised against horseradish peroxidase (HRP), which display strong reactivity to xylose and plant-specific fucose linkages (Tretter et al. 1993), are used in ELISA or western immunoblotting assays to measure relative amounts of these plant-specific glycans on protein samples. These assays typically involve use of standard control proteins containing known amounts of these glycans as references.

In a further embodiment, fucose binding lectins from *Aleuria auranti*, which bind all types of fucose linkages (Yamashita et al. 1985), are used in ELISA or western immunoblotting assays to measure relative amounts of fucose on protein samples. These assays typically involve use of standard control proteins containing known amounts of these glycans as references.

In another embodiment, mass spectrometry (for example (MALDI-TOF/TOF) is used to analyze the glycan produced by the plants described herein. Here, protein produced by the plant is treated with an enzyme (for example, PNGase A) to release the glycans. Mass spectrometry is then used to determine glycan species composition. In yet another embodiment, mass spectrometry (for example (LC-ESI-MS) is used to analyze peptides bearing the glycan produced by the plants described herein. Here, protein produced by the plant is treated with an enzyme (for example, trypsin) to produce peptide fragments, one or more of which bear the glycans. Mass spectrometry is then used to determine glycan species composition.

In one embodiment, the protein is an antibody or antibody fragment. As used herein, the term "antibody" refers to an immunoglobulin (Ig) molecule and immunologically active portions of an immunoglobulin molecule, i.e., molecules that contain an antigen binding site that specifically binds (immunoreacts with) an antigen. By "specifically bind", "immunoreacts with", or "directed against" is meant that the antibody reacts with one or more antigenic determinants of the desired antigen and does not react with other polypeptides or binds at much lower affinity ($K_d > 10^{-6}$). Antibodies include, but are not limited to, polyclonal antibodies, monoclonal antibodies, chimeric antibodies. The antibody may be from recombinant sources and/or produced in transgenic animals.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

An "antibody fragment" as used herein may include any suitable antigen-binding fragment known in the art. The term "antibody fragment" includes, without limitation, Fv (a molecule comprising the VL and VH), single chain Fv (scFV; a molecule comprising the VL and VH connected by a peptide linker, Fab, Fab', $F(ab')_2$, dsFv, ds-scFv, single domain antibodies (sdAB; molecules comprising a single variable domain and 3 CDR), and multivalent presentations of these. Also included are dimers, minibodies, diabodies, nanobodies, and multimers thereof, and bispecific antibody fragments. The antibody fragment of the present disclosure may be obtained by manipulation of a naturally occurring antibody (such as, but not limited to) enzymatic digestion, or may be obtained using recombinant methods.

In general, antibody molecules obtained from humans relate to any of the classes IgG, IgM, IgA, IgE and IgD, which differ from one another by the nature of the heavy chain present in the molecule. Certain classes have subclasses as well, such as IgG1, IgG2 (further divided into IgG2a and IgG2b), IgG3 and IgG4. Furthermore, in humans, the light chain may be a kappa chain or a lambda chain. Accordingly, in one embodiment, the antibody disclosed herein is an IgG antibody, optionally an IgG1 antibody.

Examples of antibodies contemplated for use in the methods described herein include, but are not limited to, therapeutic antibodies, such as abciximab, adalimumab, alemtuzumab, basiliximab, belimumab, bevacizumab, brentuximab vedotin, canakinumab, certolizumab, cetuximab, daclizumab, daratumumab, denosumab, eculizumab, efalizumab, golimumab, ibritumomab tiuxetan, infliximab, ipilimumab, muromonab-CD3, natalizumab, nivolumab, ofatumumab, omalizumab, palivizumab, panitumumab, pembrolizumab, rituximab, tocilizumab, atlizumab, tositumomab, trastuzumab and ustekinumab.

In one embodiment, the antibody is trastuzumab (Herceptin).

In another embodiment, the antibody is an anti-ricin antibody such as antibody D9 or humanized D9 (hD9) as described in PCT publication no. WO/2012/167346.

Also contemplated for use in the methods described herein are anti-epitope antibodies, including, but not limited to, anti-polyhistidine antibody, Penta-his antibody, anti-c-myc antibody, anti-myc antibody, anti-HA antibody, anti-hemagglutinin antibody, anti-FLAG antibody and anti-QCRL-1 antibody. In another embodiment, the protein is a serum or plasma protein such as a transport protein, regulatory protein, enzyme, protease inhibitor, clotting factor, lectin or globulin. Specific examples of these are alpha 1 antitrypsin, alpha 1 acid glycoprotein, alpha 1 fetoprotein, alpha2-macroglobulin, gamma globulins, beta-2 microglobulin, haptoglobin, ceruloplasm in, complement proteins, C-reactive protein (CRP), lipoproteins, transferrin, fibrinogen, prothrombin, thrombin, butyrylcholinesterase, acetylcholinesterase and plasma cholinesterases.

In one embodiment, the protein is butyrylcholinesterase (BuCheE). BuCheE is a cholinesterase enzyme and member of the type-B carboxylesterase/lipase family of proteins. The enzyme is involved in the detoxification of poisons including organophosphate nerve agents and pesticides, and the metabolism of drugs including cocaine, heroin and aspirin.

Also provided herein is a vector comprising two separate RNAi cassettes, one targeting XylT and one targeting FucT. In one embodiment, the RNAi cassette targeting XylT comprises SEQ ID NO: 2 or a sequence having at least 75%, 80%, 85%, 90%, 95% or 99% identity with SEQ ID NO: 2 and/or SEQ ID NO: 4 or a sequence having at least 75%, 80%, 85%, 90%, 95% or 99% identity with SEQ ID NO: 4. In another embodiment, the RNAi cassette targeting FucT comprises SEQ ID NO: 5 or a sequence having at least 75%, 80%, 85%, 90%, 95% or 99% identity with SEQ ID NO: 5 and/or SEQ ID NO: 6 or a sequence having at least 75%, 80%, 85%, 90%, 95% or 99% identity with SEQ ID NO: 6.

In one embodiment, each cassette is driven by a promoter, optionally the 35S CaMV promoter. Optionally, the vector comprises SEQ ID NO: 1, or a sequence having at least 75%, 80%, 85%, 90%, 95% or 99% identity with SEQ ID NO: 1. In another embodiment, the vector is pPFC1408 as set out in FIG. 1.

Methods

Further provided herein is a method of producing a protein in a plant, the method comprising:

(a) introducing a nucleic acid molecule encoding the protein into a plant or plant cell described herein and (b) growing the plant or plant cell to obtain a plant that expresses the protein, wherein less than 10% of the total glycan on the protein, optionally less than 9%, 8%, 7%, 6%, 5%, 4%, 3%, 2% or 1%, is $\alpha$1,3-fucosylated glycan and less than 3%, optionally less than 2% or 1% of the total glycan on the protein is $\beta$1,2-xylosylated glycan.

In one embodiment, the plant or plant cell is a plant or plant cell described herein, i.e., a genetically modified plant or plant cell with reduced $\alpha$1,3-fucosyltransferase and $\beta$1,2-xylosyltransferase activity compared to a wild type plant or plant cell, wherein less than 10% of the total glycan on a protein produced by the plant or plant cell is $\alpha$1,3-fucosylated glycan. In another embodiment, the plant or plant cell is a KDFX plant or plant cell.

In another embodiment, the protein is a recombinant protein. As used herein, the term "recombinant protein" refers to a protein that results from the expression of recombinant DNA. Recombinant DNA is DNA formed by laboratory methods of genetic recombination (such as molecular cloning) to create sequences that would not otherwise be found in the genome.

The phrase "introducing a nucleic acid molecule into a plant or plant cell" includes both the stable integration of the nucleic acid molecule into the genome of a plant cell to prepare a transgenic plant or plant cell as well as the transient integration of the nucleic acid into a plant or part thereof.

The nucleic acid molecule or vector containing the nucleic acid molecule may be introduced into the plant or plant cell using techniques known in the art including, without limitation, electroporation, an accelerated particle delivery method, a cell fusion method or by any other method to deliver the nucleic acid to a plant or plant cell, including *Agrobacterium* mediated delivery, or other bacterial delivery such as *Rhizobium* sp. NGR234*, Sinorhizobium meliloti* and *Mesorhizobium loti* (Chung et al., 2006).

The phrase "growing a plant or plant cell to obtain a plant that expresses protein" includes both growing transgenic plant cells into a mature plant as well as growing or culturing a mature plant that has received the nucleic acid molecules encoding the protein. One of skill in the art can readily determine the appropriate growth conditions in each case.

In one embodiment, plant expression vector(s) containing genes encoding the protein of interest (for example, antibody heavy chain and light chain genes) are introduced into *Agrobacterium tumefaciens* At542 or other suitable *Agrobacterium* isolates or other suitable bacterial species capable of introducing DNA to plants for transformation such as *Rhizobium* sp., *Sinorhizobium meliloti, Mesorhizobium loti* and other species (Broothaerts et al. 2005; Chung et al., 2006), by electroporation or other bacterial transformation procedures. For example, in one embodiment, the genetically modified plants described herein are seeded and grown in soil and then vacuum infiltrated with *Agrobacterium tumefaciens* strains harboring expression vectors for a protein of interest.

After selection of protein expressing primary transgenic plants, or concurrent with selection of protein expressing plants, derivation of homozygous stable transgenic plant lines may be performed. Primary transgenic plants would be grown to maturity, allowed to self-pollinate, and produce seed. Homozygosity would be verified by the observation of 100% resistance of seedlings on kanamycin plates (50 mg/L), or other selectable drug as indicated above. In one embodiment, a homozygous line with single T-DNA insertions, that are shown by molecular analysis to produce most amounts of protein, is chosen for breeding to homozygosity and seed production, ensuring subsequent sources of seed for homogeneous production of antibody by the stable transgenic or genetically modified crop (McLean et al., 2007; Olea-Popelka et al., 2005; Yu et al., 2008).

The protein may be purified or isolated from the plants using techniques known in the art, including homogenization, clarification of homogenate, affinity purification or other chromographic methods. Homogenization is any process that crushes or breaks up plant tissues and cells and produces homogeneous liquids from plant tissues, such as using a blender, or juicer, or grinder, or pulverizer such as mortar and pestle, etc. Clarification involves either/and/or centrifugation, filtration, etc. Affinity purification uses Protein A, Protein G, Protein L, and/or antibodies that bind proteins.

Other methods take advantage of specific biochemical characteristics of the protein of interest, such as pI, charge, hydrophobicity, hydrophilicity, size, etc. Purification methods would be adapted for these characteristics, such as isoelectric focusing, cation or anion exchange, hydrophobic interaction chromatography, size exclusion, metal binding, specific ligand binding.

Another form of affinity chromatography uses an antibody or antiserum against the protein of interest.

Chromatography can be exchanged for batch processes involving resins designed for cation exchange, anion exchange, hydrophobic interaction, metal binding, specific ligand binding.

As well, specific combinations of more than one of these techniques can be used to purify a protein of interest.

The nucleic acid vectors encoding proteins described herein will also contain other elements suitable for the proper expression of the protein in the plant or plant cell. In particular, each vector will also contain a promoter that promotes transcription in plants or plant cells. Suitable promoters include, but are not limited to, cauliflower mosaic virus promoters (such as CaMV35S and 19S), nopaline synthase promoters, alfalfa mosaic virus promoter, and other plant virus promoters. Constitutive promoters, such as plant actin gene promoters, and histone gene promoters can also be used.

Inducible promoters, such as light-inducible promoters: ribulose-1,5-bisphosphate carboxylase oxidase (a.k.a. RUBISCO) small subunit gene promoter; chlorophyll a/b binding (CAB) protein gene promoter; and other light inducible promoters may also be used. Other inducible promoters include chemically-inducible promoters, alcohol inducible promoters, and estrogen inducible promoters.

Synthetic promoters, such as the so-called superpromoter comprised of 3 mannopine synthase gene upstream activation sequences and the octopine synthase basal promoter sequence (Lee et al., 2007) can also be used.

Predicted promoters, such as can be found from genome database mining (Shahmuradov et al., 2003) may also be used.

The nucleic acid vectors will also contain suitable terminators useful for terminating transcription in the plant or plant cell. Examples of terminators include the nopaline synthase poly A addition sequence (nos poly A), cauliflower mosaic virus 19S terminator, actin gene terminator, alcohol dehydrogenase gene terminator, or any other terminator from the GenBank database.

The nucleic acid vectors may also include other components such as signal peptides that direct the polypeptide the secretory pathway of plant cells, such as the *Arabidopsis thaliana* basic chitinase SP (Samac et al., 1990) as described above.

Selectable marker genes can also be linked on the T-DNA, such as kanamycin resistance gene (also known as neomycin phosphotransferase gene II, or nptII), Basta resistance gene, hygromycin resistance gene, or others.

The following non-limiting Example is illustrative of the present disclosure:

EXAMPLE 1

Procedure: Vector Construction, Development and Screening of Primary Transgenic Plants A single RNAi expression vector based on the pBIN19 vector of Bevan, M. (1984) and the FucT and XylT sequences of Strasser et al (2008) was created. In particular, a single vector with 2 separate RNAi knockdown cassettes for each of XylT and FucT, each driven by the 35S CaMV promoter was produced and referred to as pPFC1408 (FIGS. 1 and 2).

SEQ ID NO: 1 provides the sequence of the pPFC1408 T-DNA region. The T-DNA region includes the following genetic elements:

| Nucleic acids | Description | SEQ ID NO |
|---|---|---|
| 1-148 | LB, left border region | |
| 169-475 | nopaline synthase promoter | |
| 476-1671 | nptII coding sequence | |
| 1672-1927 | nopaline synthase terminator | |
| 1964-2379 | Cauliflower mosaic virus 35S enhancer and promoter | |
| 2396-2711 | XylT sense sequence | SEQ ID NO: 2 |
| 2712-2921 | XylT intervening sequence | SEQ ID NO: 3 |
| 2922-3238 | XylT antisense sequence | SEQ ID NO: 4 |
| 3246-3457 | *Agrobacterium* gene 7 terminator | |
| 3498-3913 | Cauliflower mosaic virus 35S enhancer and promoter | |
| 3941-4366 | FucT sense sequence | SEQ ID NO: 5 |
| 4367-4576 | XylT intervening sequence | SEQ ID NO: 3 |
| 4580-5010 | FucT antisense sequence | SEQ ID NO: 6 |
| 5011-5222 | *Agrobacterium* gene 7 terminator | |
| 5257-5418 | RB, right border region | |

Figure 3:
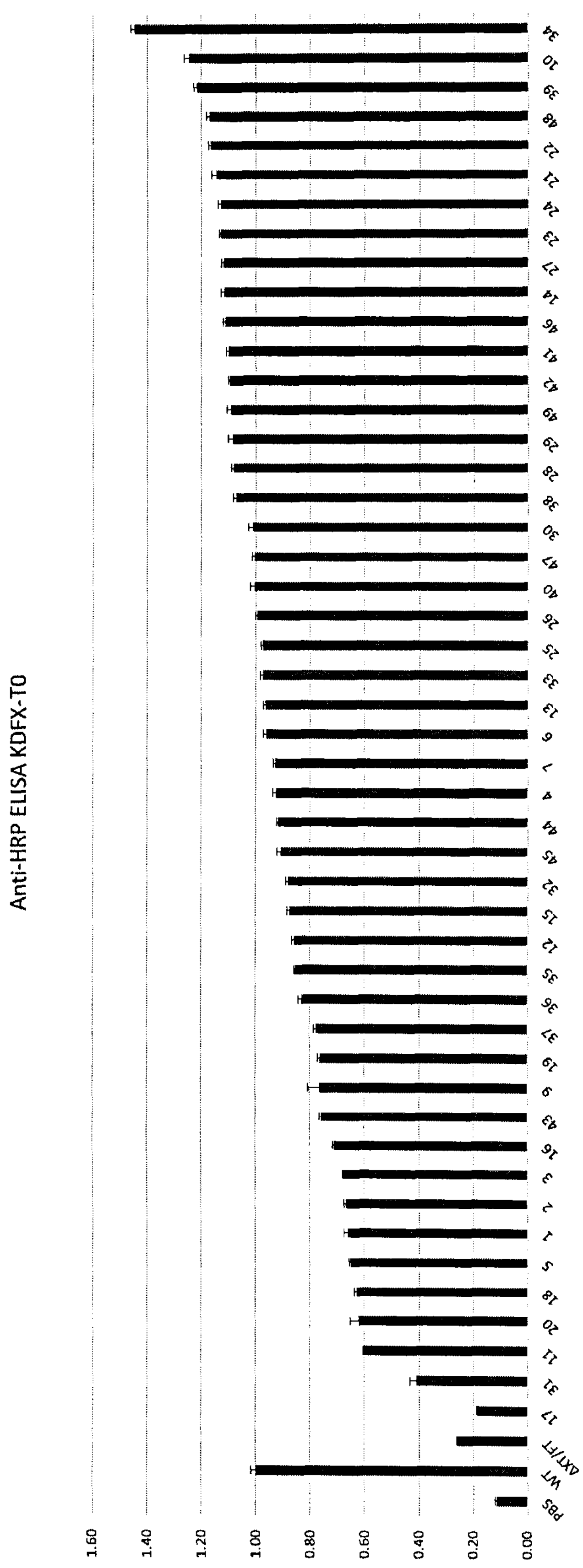
FIG. 3 shows primary transgenic plant ($T_0$) extracts screened with anti-HRP ELISA. PBS, phosphate-buffered saline blank well control; WT, wild-type *N. benthamiana* (USDA PI 555478, aka TW16); ΔXT/FT, line of Strasser et al. (2008); x-axis numbers indicate individual primary transgenic plant numbers. Note that 48 primary transgenic plants were screened, with primary transgenic plant average being 0.94+/−0.034 ([mean; std. error]; see Table 1). Primary transgenic plant number $T_0$-17 was chosen to go forward for line development based on low anti-HRP ELISA value (0.18+/−0.001 [mean; std. error]) compared with ΔXT/FT (0.26+/−0.001 [mean; std. error]).

Seed for wild-type (WT) *Nicotiana benthamiana* cultivar (PI 555478; also referred to as TW16) was obtained from the US Department of Agriculture in 2014 and propagated for initiation of development of the KDFX line mid-year. Briefly, WT *N. benthamiana* leaf discs were cut and exposed to an *Agrobacterium* At542 culture harboring pPFC1408 (vector designed to express fucosyl- and xylosyl-transferase RNAi knockdown cassettes). The leaf discs were grown on a selective medium to encourage callus growth only by those cells that had been transformed by the *Agrobacterium*. After small shoots emerged, they were transferred to a new medium to stimulate root growth. Finally, the rooted plants were transferred to soil in a controlled growth room, and allowed to grow and eventually produce seed. There were a total of 48 plants in this primary transgenic plant ($T_0$) population. Total soluble protein was isolated from each plant and examined via ELISA (α-HRP antibody) for α1,3-fucose and β1,2-xylose additions to endogenous protein. Of these 48 plants, transgenic plant #17 displayed lower amounts of α1,3-fucose and β1,2-xylose additions compared to that obtained with the Strasser ΔXT/FT line (FIG. 3). Antibodies raised against horseradish peroxidase (HRP) display strong reactivity to xylose and plant-specific fucose linkages (TRETTER et al. 1993). Thus, α-HRP primary antibodies are used as a screening tool to determine presence of those plant-specific monosaccharide linkages.

Production and Screening of Subsequent Generations of Transgenic Plants

Because primary transgenic plant #17 ($T_0$-17) displayed the lowest anti-HRP ELISA binding, it was self-pollinated to produce the $T_1$ seed lot. This seed lot was a mixture of homozygous wild-type, hemizygous, and homozygous T-DNA insertions.

Figure 4:
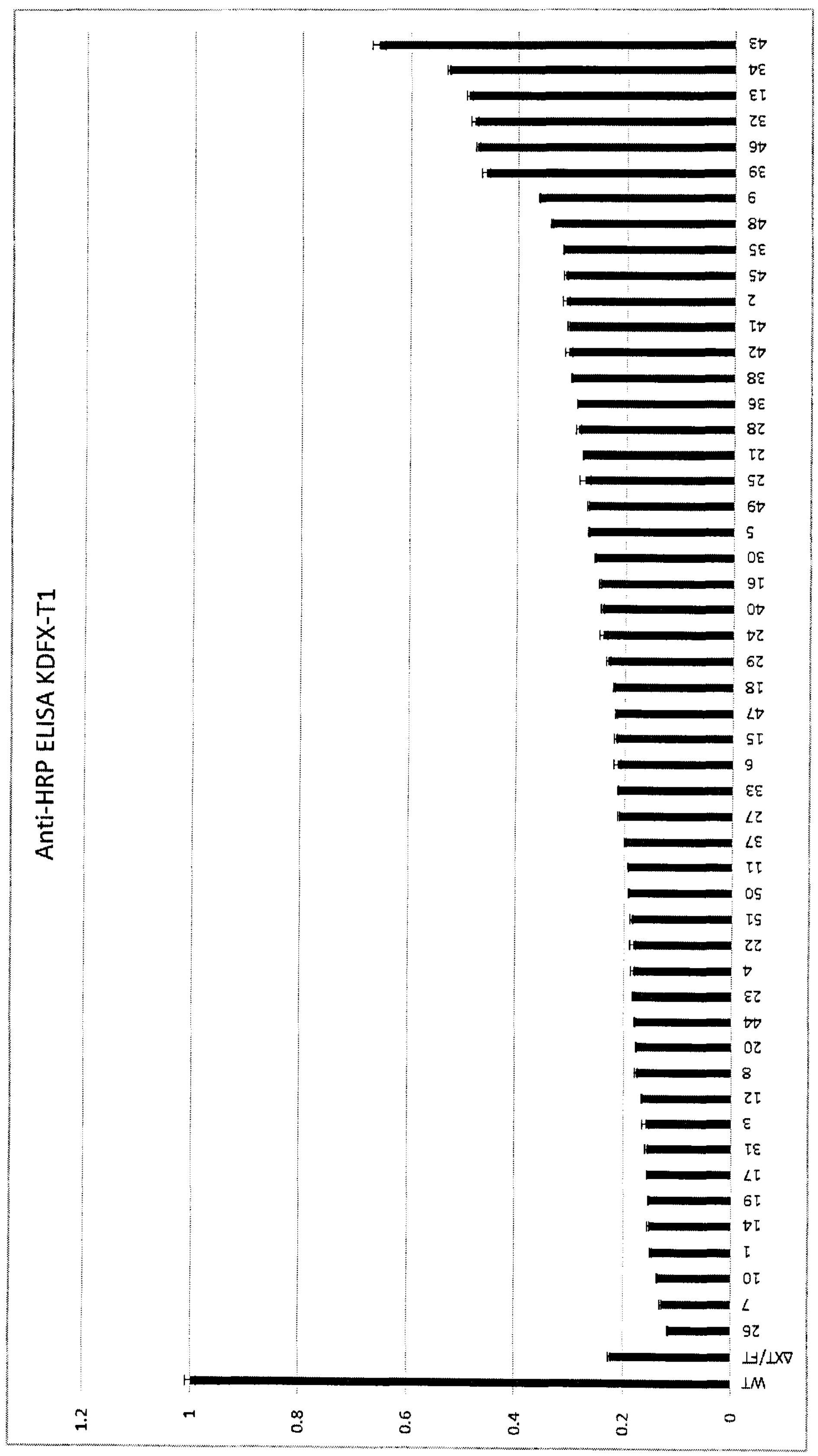
FIG. 4 shows first generation transgenic plant ($T_1$) extracts screened with anti-HRP ELISA. WT, wild-type *N. benthamiana* (USDA PI 555478, aka TW16); ΔXT/FT, line of Strasser et al. (2008); x-axis numbers indicate individual first generation transgenic plant numbers. Note that 51 first generation transgenic plants were screened. First generation transgenic plant number $T_1$-17-7 was chosen to go forward for line development based on low anti-HRP ELISA value (0.13+/−0.001 [mean; std. error]) compared with ΔXT/FT (0.22+/−0.003 [mean; std. error]).

Fifty-one seeds from the $T_1$ seed lot were grown, and the plant protein extracts were screened with the α-HRP ELISA assay. Plants #17-07 and #17-26 had extremely low HRP binding, indicating low α1,3-fucose- and β1,2-xylose-containing plant-specific glycans (FIG. 4). Genomic DNA from transgenic plants #17-07 and #17-26 were prepared by taking immature leaves from the shoot apical meristem and using the DNEasy Plant MiniKit (Qiagen, Hilden, Germany) according to the manufacturer's instructions. DNA samples were then quantified and sample purity was assessed using a NanoDrop 2000c spectrophotometer (Thermo Scientific, Delaware, USA). DNA Samples were sent to the TCAG Next Generation Sequencing Facility at Sick Kids Hospital in Toronto, Ontario, for whole-genome Illumina HiSeq sequencing. Analysis identified homozygosity at three T-DNA insertion locations (for more details, see below); however, at the time of sequencing it was unclear which plant would be carried forward for line development. Based on plant health, #17-07 was chosen and was self-pollinated to produce the $T_2$ seed lot.

Figure 5:
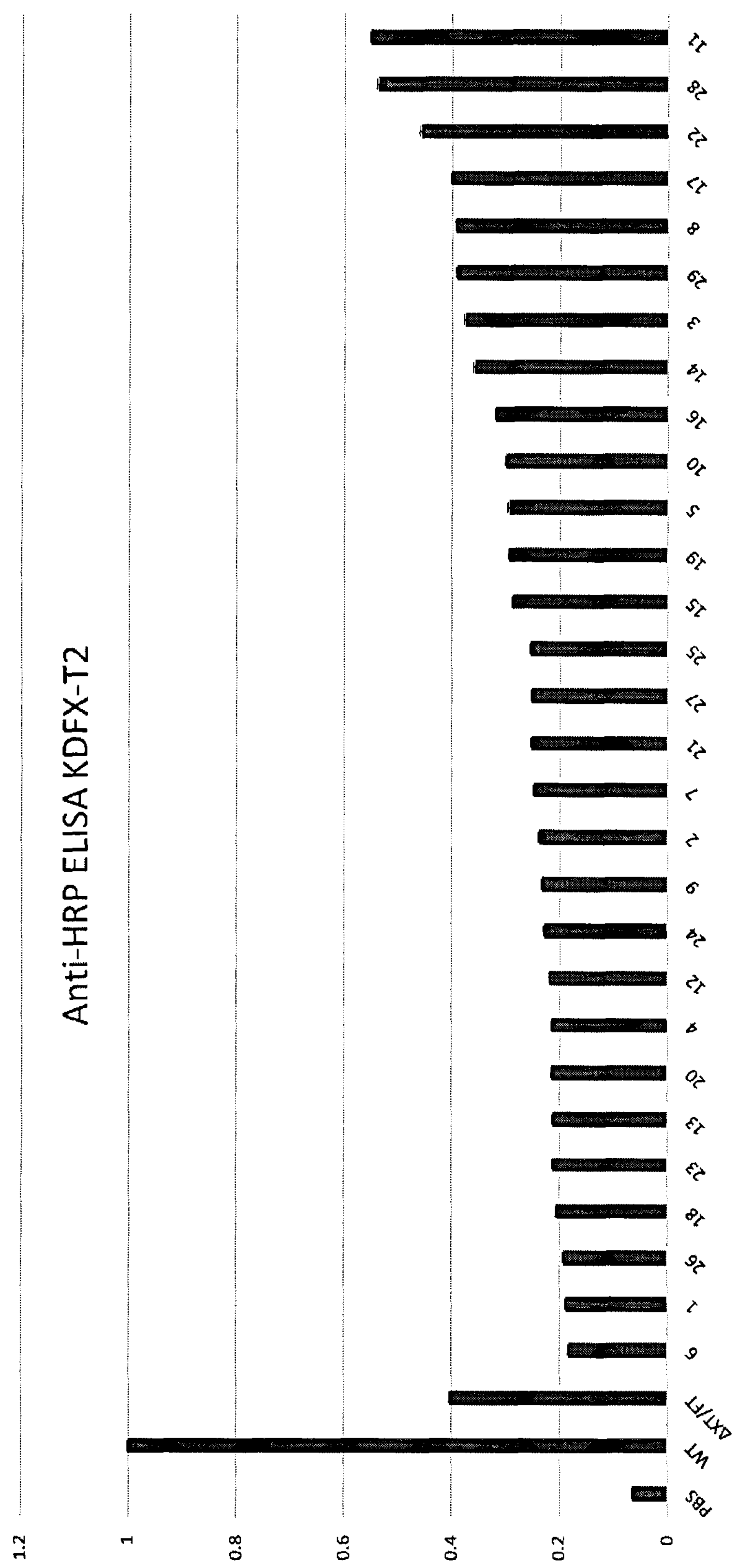
FIG. 5 shows second generation transgenic plant ($T_2$) extracts screened with anti-HRP ELISA. PBS, phosphate-buffered saline; WT, wild-type *N. benthamiana* (USDA PI 555478, aka TW16); ΔXT/FT, line of Strasser et al. (2008); x-axis numbers indicate individual second generation transgenic plant numbers. Note that 29 second generation transgenic plants were screened. Second generation transgenic plant number $T_2$-17-7-26 was chosen to go forward for line development based on low anti-HRP ELISA value (0.19+/−0.003 [mean; std. error]) compared with ΔXT/FT (0.40+/−0.006 [mean; std. error]).

Second generation transgenic plants ($T_2$ seed lot) were grown and protein extracts were screened with anti-HRP ELISA. In total, 29 second generation transgenic plants were screened. Second generation transgenic plant number $T_2$-17-7-26 was chosen to go forward for line development based on low anti-HRP ELISA value (0.19+/−0.003 [mean; std. error]) compared with ΔXT/FT (0.40+/−0.006 [mean; std. error]). See FIG. 5.

Illumina "next-generation" sequencing is powerful DNA sequencing method allowing for high throughput analysis due to multiple genome coverage. This technology was again used in order to sequence the genome of the $T_2$-17-7-26 plant. Sequencing returned 297,913,122 sequence pairs of data. Given that the *N. benthamiana* genome has an estimated size of over 3.5 Gb (Fernandez-Pozo et al., 2014) this dataset therefore provided 9.8-fold genome coverage assuming an even distribution of sequencing reads.

In order to locate genomic T-DNA insertions, the data set was searched for chimeric sequences having both *N. ben-*

*thamiana* genomic sequence as well as T-DNA right or T-DNA left border sequences (LB, RB) from pPFC1408 with a similarity fraction of at least 0.8 and length fraction of at least 0.2. These chimeric sequences were then browsed visually in order to identify the unique genomic DNA sequences that were contiguous with the LB and RB sequences of the T-DNA. Analysis of these chimeric sequence data revealed three independent T-DNA insertions in the genome of plant $T_2$-17-7-26. Genomic DNA sequences associated with insertion sites 1 to 3 were identified in the Sol Genomics database for *N. benthamiana* (Fernandez-Pozo et al., 2014). These public database sequences were used as references to align genomic sequence components of chimeric sequences with specific regions of the *N. benthamiana* genome into which T-DNA insertions occurred. T-DNA insertion can cause deletions in genomic DNA. Indeed, assembly of the genomic T-DNA integration loci revealed that there were small amounts of genomic DNA absent from these insert sites. Among T-DNA insertions 1, 2 and 3 in the DNA of plant $T_2$-17-7-26, 51 bp, 29 bp and 67 bp, respectively, were missing from associated native DNA sequences as reported in the Sol Genomics database for *N. benthamiana* (Fernandez-Pozo et al., 2014).

No evidence of each of these three deletion sequences could be found in the entire $T_2$-17-7-26 genomic sequence dataset, indicating that this plant was homozygous at all three T-DNA loci. In support of triple homozygosity, genomic DNA of sibling plant $T_2$-17-7-6, which also had low HRP binding (see FIG. 5) was likewise sequenced. Analysis of $T_2$-17-7-6 DNA revealed both absence of the 29-bp sequence in association with T-DNA insertion 2 sequence, as well as presence of the 29-bp sequence but only in association with adjacent *N. benthamiana* genomic DNA sequence, indicating hemizygosity for this plant at this T-DNA insertion locus as well as the power of whole-genome sequence analysis for determination of genotype at a given locus.

Because second generation transgenic plant $T_2$-17-7-26 was shown to be homozygous at all 3 T-DNA loci, it was self-pollinated and third generation transgenic plants were grown from its seed lot. Protein extracts were screened with anti-HRP ELISA. In total, 45 third generation transgenic plants were screened and plant number $T_3$-17-7-26-9 was chosen to go forward for line development based on low anti-HRP ELISA value (0.27+/−0.013 [mean; std. error]) compared with ΔXT/FT (0.60+/−0.004 [mean; std. error]). See FIG. 6.

Genomic DNA was prepared from third generation transgenic plant number $T_3$-17-7-26-9, which was also sequenced and analyzed in the same fashion as was its parent's DNA. This analysis confirmed that plant $T_3$-17-7-26-9 was homozygous at all three T-DNA insertion loci. Therefore, plant $T_3$-17-7-26-9 was self-pollinated to produce a fourth generation of transgenic plants.

Figure 7:
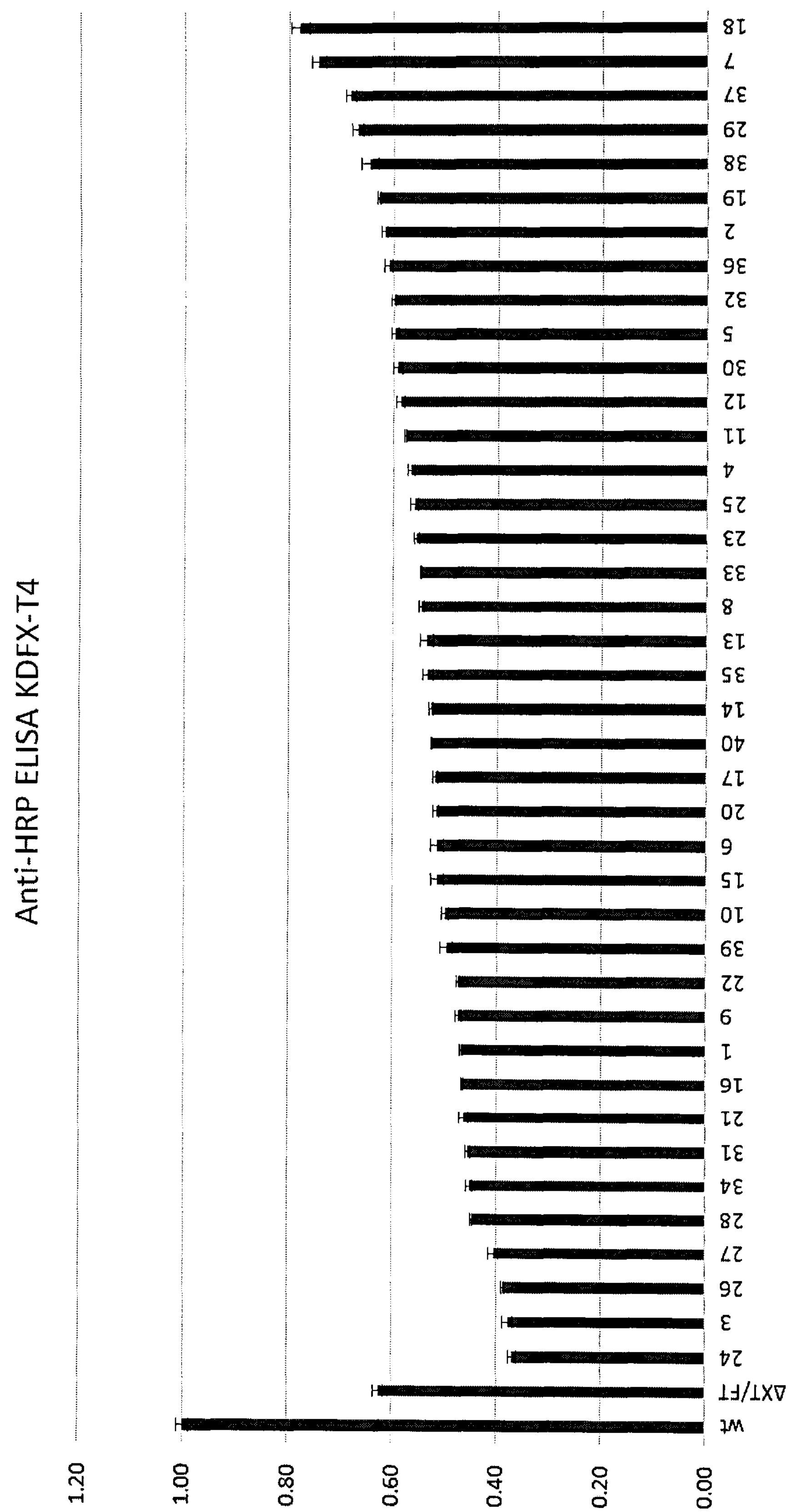
FIG. 7 shows fourth generation transgenic plant ($T_4$) extracts screened with anti-HRP ELISA. PBS, phosphate-buffered saline; wt, wild-type *N. benthamiana* (USDA PI 555478 aka TW16); ΔXT/FT, line of Strasser et al. (2008); x-axis numbers indicate individual fourth generation transgenic plant numbers. Note that 48 fourth generation transgenic plants were screened (not all are shown). Fourth generation transgenic plant number $T_4$-17-7-26-9-3 was chosen to go forward for line development based on low anti-HRP ELISA value (0.38+/−0.009 [mean; std. error]) compared with ΔXT/FT (0.63+/−0.010 [mean; std. error]).

Fourth generation transgenic plants ($T_4$) were likewise grown and protein extracts were screened with anti-HRP ELISA. Note that 48 fourth generation transgenic plants were screened (see FIG. 7; note that not all plants are shown). Fourth generation transgenic plant number $T_4$-17-7-26-9-3 was chosen to go forward for line development based on low anti-HRP ELISA value (0.38+/−0.009 [mean; std. error]) compared with ΔXT/FT (0.63+/−0.010 [mean; std. error]).

Genomic DNA was prepared from third generation transgenic plant number $T_3$-17-7-26-9, which was analyzed by PCR genotyping assay. This analysis confirmed that plant $T_3$-17-7-26-9 was homozygous at all three T-DNA insertion loci. Therefore, plant $T_4$-17-7-26-9-3 was self-pollinated to produce a fifth generation of transgenic plants.

Figure 8:
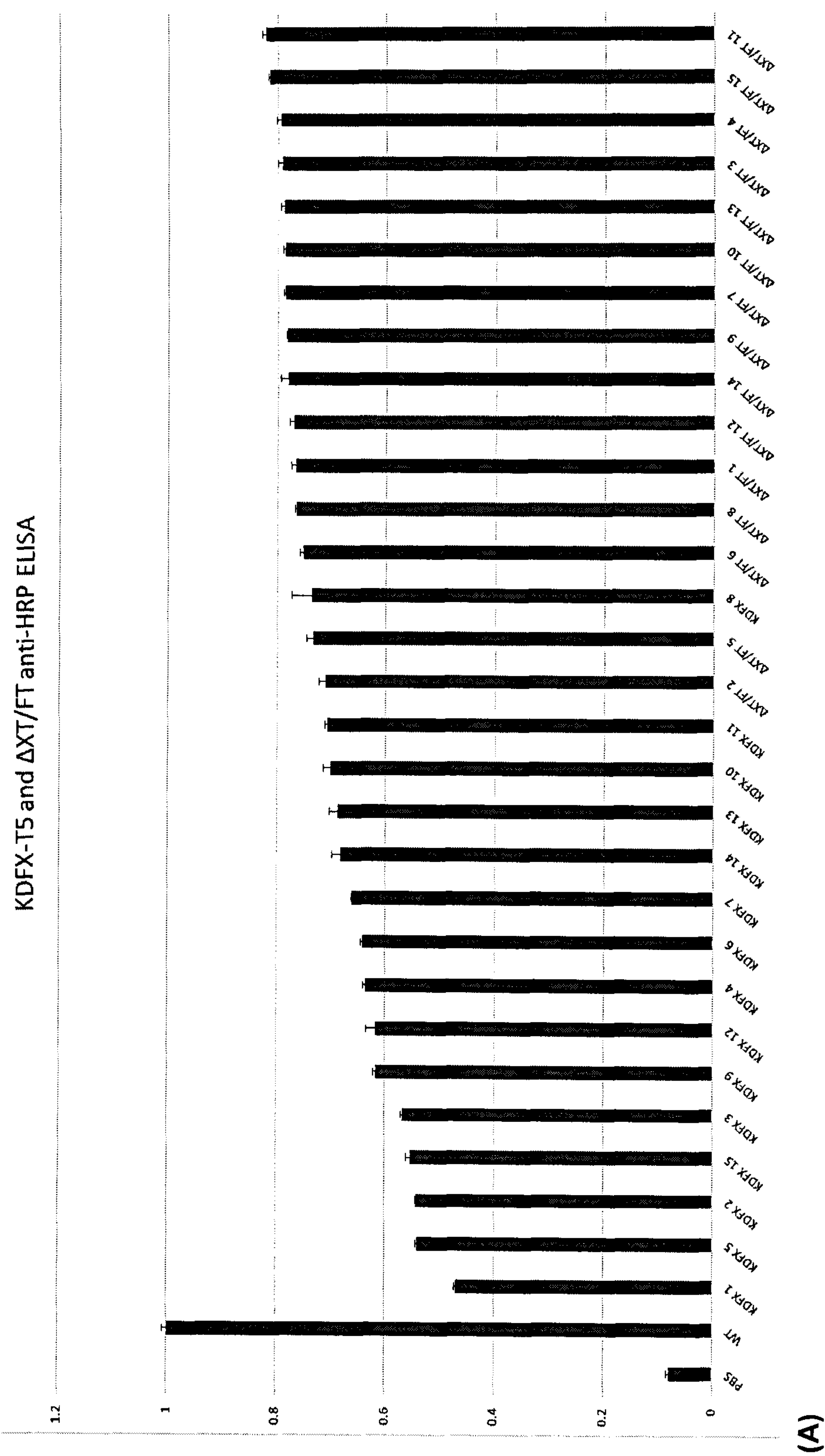
FIG. 8(A) shows fifth generation transgenic plant ($T_5$) extracts screened with anti-HRP ELISA. PBS, phosphate-buffered saline; WT, wild-type *N. benthamiana* (USDA PI 555478 aka TW16); 15 ΔXT/FT plants grown from line of Strasser et al. (2008), numbered ΔXT/FT1 through ΔXT/FT15; 15 KDFX $T_5$ plants, numbered KDFX1 through KDFX15. Note that in total 30 fifth generation transgenic plants were screened (not all are shown). Also, 30 ΔXT/FT plants were likewise screened (not all are shown).
FIG. 8(B) shows KDFX $T_5$ generation and ΔXT/FT averages and standard errors are given in inset.

Fifth generation transgenic plants ($T_5$) were likewise grown and protein extracts were screened with anti-HRP ELISA. In total 30 fifth generation transgenic plants were screened (see FIG. 8; not all plants are shown). Also, 30 ΔXT/FT plants were likewise screened. Fifth generation transgenic plant number $T_5$-17-7-26-9-3-1 would be a likely choice to proceed with for line development based on low anti-HRP ELISA value (0.47+/−0.002 [mean; standard error]) compared with ΔXT/FT (0.78+/−0.007 [mean; standard error]).

Furthermore, in addition to fifth generation transgenic plant $T_5$-17-7-26-9-3-1, four more plants (i.e., $T_5$-17-7-26-9-3-9, $T_5$-17-7-26-9-3-11, $T_5$-17-7-26-9-3-12, and $T_5$-17-7-26-9-3-10) have all been self-pollinated. Progeny from all 5 of these $T_5$ transgenic plants will be analyzed with the anti-HRP ELISA to demonstrate stable inheritance of the knock-down phenotype for the FucT and XylT genes.

Sequence Data Revealed that 2 of 3 T-DNA Loci Have Complex Insertions

Sequence analysis revealed that two of the three T-DNA insertions were more complex than a simple, single insertion of the T-DNA region of pPFC1408 (see FIG. 9). T-DNA insertion 1 is a simple, single and complete T-DNA insertion that incorporated 5171 base pairs of the 5418 bp T-DNA sequence of pPFC1408 given in FIG. 2 and SEQ ID NO: 1. T-DNA insertion 1 did not incorporate 117 base pairs from the left side of the left border (LB) of that 5418 bp T-DNA sequence and likewise did not incorporate 130 base pairs from the right side of the right border (RB) sequence of that 5418 T-DNA sequence.

T-DNA insertions 2 and 3 have complex insertions. Insertion 2 is a double, inverted insertion consisting of two complete T-DNA regions, each of similar, but non-identical, size to that of insertion 1. The double insertions at this locus have opposite orientations, with their LB sequences being adjacent and their RB sequences being at opposite ends of this complex insertion (FIG. 9). Furthermore, insertion 2 is of 10383 bp, and contains complete and duplicate sequences of the two RNAi genes of interest: namely, the FucT-targeting RNAi gene and the XylT-targeting RNAi gene.

Insertion 3 is a double, tandem insertion consisting of two truncated T-DNA regions. The truncations are similar in that they both involve deletions of more than 2.7 kilobase pairs (kbp) of DNA sequence from and including the entire LB. Furthermore, T-DNA insertion 3 does not contain a complete XylT-targeting RNAi gene; however, it does contain 2 complete FucT-targeting RNAi genes. Sequence data suggest that this insertion is of 5033 bp (FIG. 9).

FIG. 10 gives sequence alignments of the three T-DNA insertion sites with corresponding *Nicotiana benthamiana* genomic DNA sequences from the Sol Genomics Network *N. benthamiana* genome sequencing project (Fernandez-Pozo et al., 2014; solgenomics.net).

A PCR Assay was Developed to Demonstrate Genotype for Each of Three T-DNA Insertion Loci Knowledge of DNA sequences at each T-DNA insertion locus allowed for development of PCR-based assays for determination of genotype at each of these loci. Oligonucleotide primers were designed to be specific for binding to T-DNA sequence or for binding to flanking genomic sequence about each insertion locus. Table 1 gives each of these oligonucleotide sequences, as well as diagnostic sizes for T-DNA insertion-specific or genomic DNA-specific (i.e, "no-insertion") PCR products. PCR reactions were performed for each of the three T-DNA loci using these primers; see FIG. 11. As seen in this figure, $T_4$ generation plant $T_4$-17-7-26-9-3 is confirmed to be homozygous at all 3 T-DNA loci, as it has the smaller diagnostic PCR product predicted for each locus-specific reaction as given in Table 1. Also in FIG. 11, DNA from TW16 wild type plants are shown to be homozygous for lack of insertions (i.e., no insertion or null insertions) at each locus by virtue of having the larger diagnostic PCR product sizes for each of the three T-DNA locus specific reactions.

TABLE 1

Oligonucleotide primers and diagnostic PCR product sizes for 3 T-DNA insert loci.

| T-DNA Insert | Primer name | Binding site | Sequence (5'→3') | Predicted PCR product size (bp): T-DNA insert | Predicted PCR product size (bp): Genomic |
|---|---|---|---|---|---|
| Insert#1 | TD-RB-F1 | Insert1, T-DNA | GGCCGGCCTTAATTAAAGATT (SEQ ID NO: 7) | 250 | — |
| | KFX-Ins1-3G1 | Insert1, 3' genome flank | AAACTTTCCGTGCTTCTCCA (SEQ ID NO: 8) | | 454 |
| | KFX-Ins1-5G1 | Insert1, 5' genome flank | TTGCACTTTGTGTGGGAATG (SEQ ID NO: 9) | — | |
| Insert#2 | TD-RB-F1 | Insert2, T-DNA | GGCCGGCCTTAATTAAAGATT (SEQ ID NO: 7) | 234 + | — |
| | KFX-Ins2-3G1 | Insert2, 3' genome flank | GCATGTCCACTTGACACACC (SEQ ID NO: 10) | 205 | 358 |
| | KFX-Ins2-5G1 | Insert2, 5' genome flank | GACCTAAATCGTGGGTTTATGC (SEQ ID NO: 11) | | |
| Insert#3 | KFX-Ins3-3G1 | Insert3, 3' genome flank | AAGGGGAACCGGTCTAGTTG (SEQ ID NO: 12) | — | 1000 |
| | KFX-Ins3-5G66 | Insert3, 5' genome flank | TCTGCCATTCACCACTTCCATCC (SEQ ID NO: 13) | 500 | |
| | TD-PXT-F3 | Insert3, T-DNA | GGTATGCTCCTCTTCTTGTTC (SEQ ID NO: 14) | | — |

Figure 6:
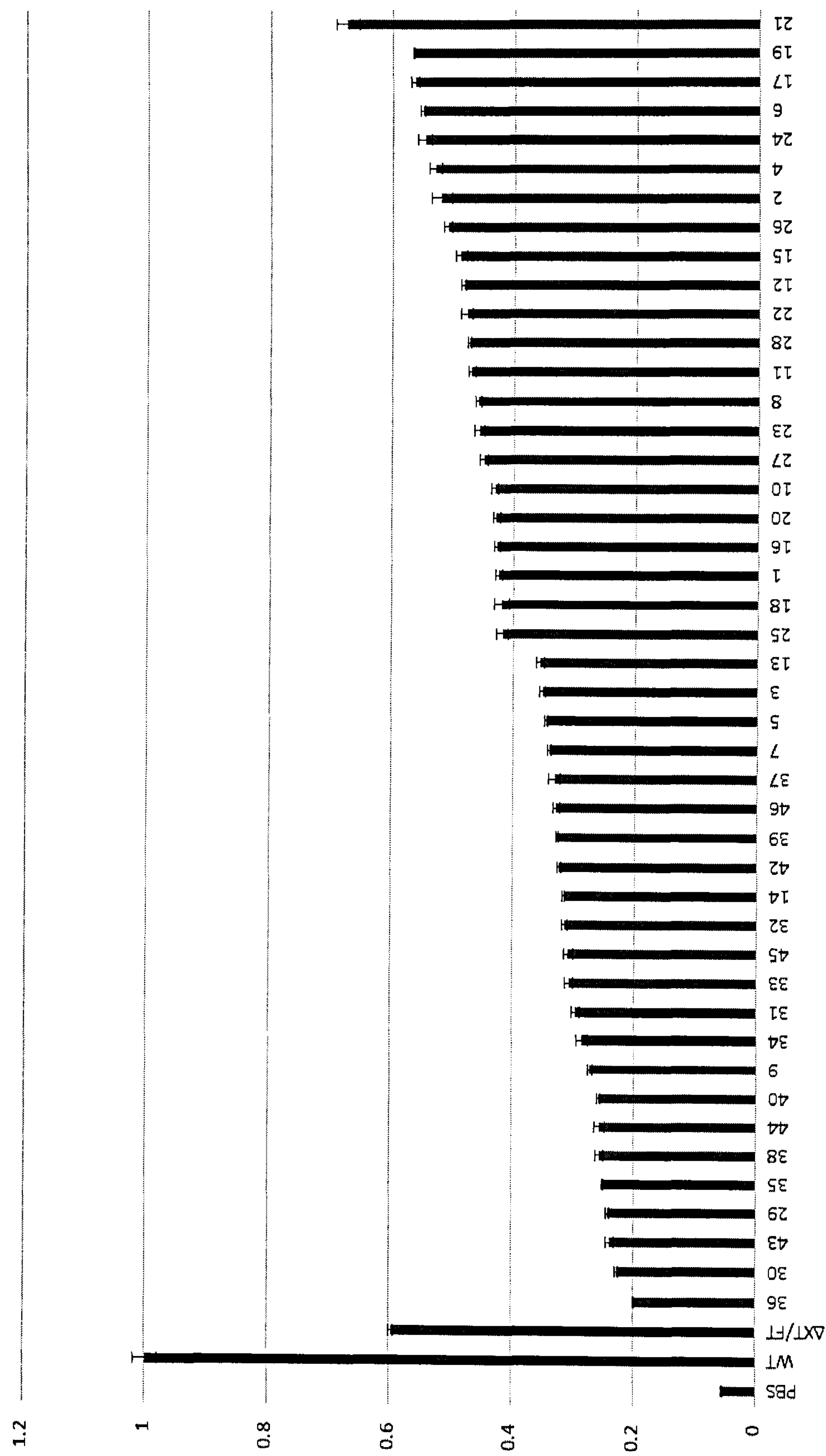
FIG. 6 shows third generation transgenic plant ($T_3$) extracts screened with anti-HRP ELISA. PBS, phosphate-buffered saline; WT, wild-type *N. benthamiana* (USDA PI 555478 aka TW16); ΔXT/FT, line of Strasser et al. (2008); x-axis numbers indicate individual third generation transgenic plant numbers. Note that 45 third generation transgenic plants were screened. Third generation transgenic plant number $T_3$-17-7-26-9 was chosen to go forward for line development based on low anti-HRP ELISA value (0.27+/−0.013 [mean; std. error]) compared with ΔXT/FT (0.60+/−0.004 [mean; std. error]).
Figure 11:
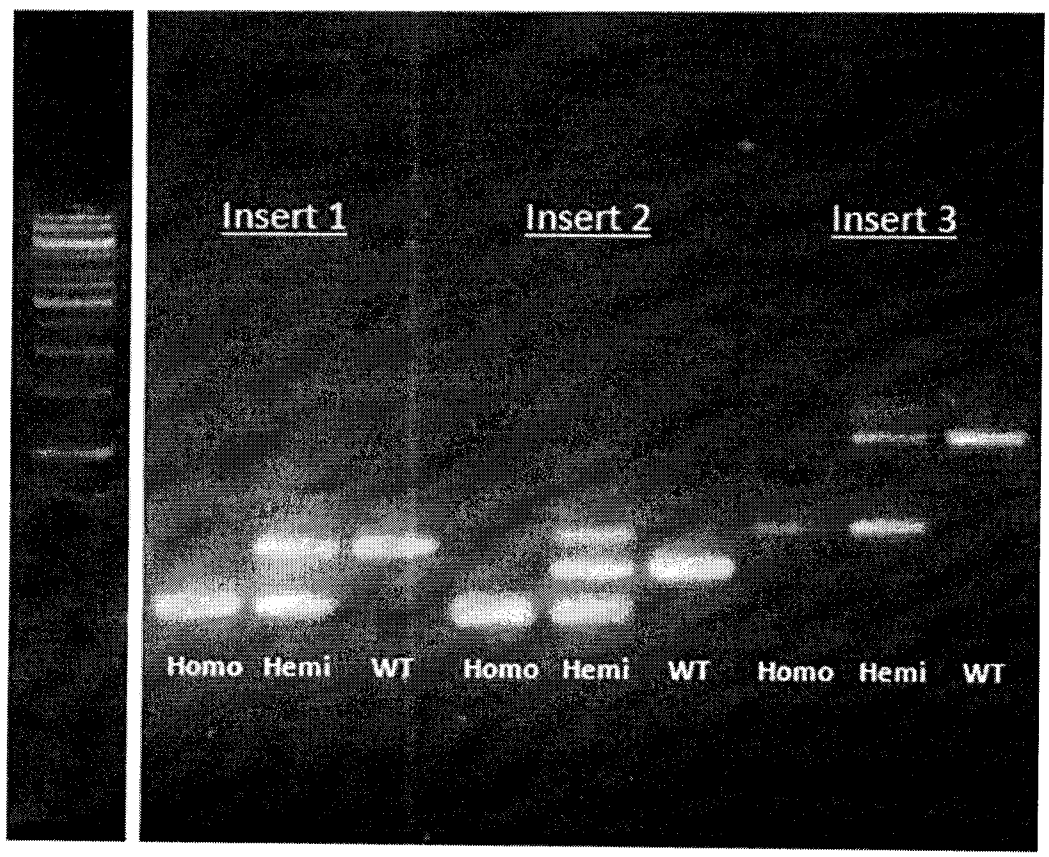
FIG. 11 shows a genotyping assay, using polymerase chain reaction (PCR) performed to detect presence or absence of T-DNA inserts at three locations in the *N. benthamiana* genome. Multiplex reactions were performed for each T-DNA locus using oligonucleotide primers for the amplification of the native DNA and insertion T-DNA. KDFX $T_4$ generation plant KDFX-17-7-26-9-3, which is homozygous at all 3 T-DNA loci, is indicated in the figure as "Homo." KDFX $T_1$ generation plant KDFX-17-6 of 2016, which is hemizygous at each of the 3 T-DNA loci, is indicated as "Hemi." WT indicates the TW16 wild type control plant. DNA standard ladder is on the left.

These PCR assays were also used to determine the genotypes of 64 more $T_1$ generation plants (i.e., in addition to the 51 $T_1$ generation plants screened with the anti-HRP ELISA as shown in FIG. 6). (These 64 additional T1 generation plants are referred to as "KDFX-17-x of 2016" where x=1 to 64.) From among these 64 plants, as seen in FIG. 11, $T_1$ generation plant KDFX-17-6 of 2016 was determined to be hemizygous at each of the 3 T-DNA insertion loci by virtue of having both the larger and the smaller diagnostic PCR product sizes for each of the three T-DNA locus-specific reactions. Dual presence of both product sizes for hemizygotes at each T-DNA locus demonstrates the robustness of these diagnostic PCR assays.

Among the 64 more $T_1$ generation plants described in the above paragraph, plants with six different genotypes were identified: wild-type revertant (i.e., homozygous for no insertions or null-T-DNA insertions at each of the three T-DNA loci); homozygote for T-DNA insertion 1 only (note that two plants of this genotype were identified; see FIG. 12); homozygote for T-DNA insertion 2 only; homozygote for T-DNA insertion 3 only; homozygote for both T-DNA insertions 1 and 2 (therefore, homozygous for null-T-DNA insertion at locus 3); and homozygote for T-DNA insertions 1 and 3 only (therefore, homozygous for null-T-DNA insertion at locus 2). These plants were screened with the anti-HRP ELISA and compared with ΔXT/FT (Strasser et al. (2008)), TW16 wild-type and $T_5$ generation plant 17-7-26-9-3 as controls (see FIG. 12). Note that among the 3 individual T-DNA insertion loci, homozygosity at insertion 1 provides the best knock-down of xylosyltransferase and fucocyltransferase activities, while homozygosity at insertion 3 provides very little knock-down of xylosyltransferase and fucocyltransferase activities. Furthermore, homozygosity at 2 T-DNA loci (insertions 1 and 2) provides for increased knockdown of xylosyltransferase and fucocyltransferase activities, being better than the ΔXT/FT control and similar to the $T_5$ generation plant 17-7-26-9-3 triple homozygote control.

Without being bound by theory, it is suggested that the multiple and complete T-DNA insertions at locus 1 and locus 2, which provide 3 complete FucT-targeting RNAi genes and 3 complete XylT-targeting RNAi genes, confer the improved RNAi knockdown of FucT- and XylT-activities over the ΔXT/FT line of Strasser et al. (2008) because ΔXT/FT may only possess single RNAi genes targeting FucT and XylT.

Furthermore, without being bound by theory, it is suggested that T-DNA insertion 3, which provides 2 complete FucT-targeting RNAi genes, also confers RNAi knockdown of FucT-activity; however, the anti-HRP ELISA is not sensitive enough to demonstrate this for the plant that is a single homozygote for T-DNA insertion 3 only (shown in FIG. 12).

For this research and development program, five generations of transgenic plants plus their progenitor cohort of $T_0$ primary transgenic plants were produced, each having individual plants shown with lower anti-HRP ELISA values than the ΔXT/FT plant line (Strasser et al., 2008); see Table 2. In this table, it can be seen that as the development of the plant line progressed through the generations, plants chosen for each generation had further improved anti-HRP ELISA values as compared with the ΔXT/FT plant line until generation $T_3$, after which the ELISA assay started to show sensitivity limits. This is because lesser ELISA reactivity was occurring in latter generations due to increasing improvements in knocking-down of xylosyltransferase and fucosyltransferase activities. Thus, ELISA development times required lengthening for development of the ELISA assay signal, causing reduced assay sensitivity.

TABLE 2

Summary of generation analyses using anti-HRP ELISA. Primary transgenic plants ($T_0$) plus five generations of progeny plants were screened to identify individual plants to produce seed for subsequent generations

| | ΔXT/FT (avg. +/− SE) | Chosen plant (#: avg. +/− SE) | Generation (avg. +/− SE) | | |
|---|---|---|---|---|---|
| 48 | 0.26 +/− 0.001 | 0.18 +/− 0.001 | 0.94 +/− 0.034 | 17 | 0.69 |
| 51 | 0.22 +/− 0.003 | 0.13 +/− 0.001 | 0.26 +/− 0.160 | 17-7 | 0.59 |
| 29 | 0.40 +/− 0.006 | 0.19 +/− 0.003 | 0.29 +/− 0.003 | 17-7-26 | 0.48 |
| 45 | 0.60 +/− 0.004 | 0.27 +/− 0.013 | 0.39 +/− 0.017 | 17-7-26-9 | 0.45 |
| 48 | 0.63 +/− 0.010 | 0.38 +/− 0.009 | 0.54 +/− 0.015 | 17-7-29-9-3 | 0.60 |
| 30 | 0.78 +/− 0.007 | 0.47 +/− 0.002 | 0.62 +/− 0.019 | 17-7-26-9-3-1 | 0.60 |

Thus a more sensitive assay was required for showing knockdown of xylosyltransferase and fucocyltransferase activities. Plants from two generations were grown and used for transient expression of a monoclonal antibody, which was purified and sent for mass spectrometry analysis (MS) at the diagnostic laboratory of the National Research Council of Canada (NRC, Ottawa); see Table 3. This occurred at 2 separate occasions, and the same monoclonal antibody was similarly and coincidentally expressed in ΔXT/FT plants to provide for comparison. MALDI-TOF/TOF MS analyses were performed on glycans released from the purified monoclonal antibodies by PNGase A. The table shows that glycans from a pool of 6 $T_2$ offspring plants of plant $T_1$: 17-7, and the glycans from a pool of 6 $T_3$ offspring plants of plant $T_2$: 17-7-26, had at least 6-fold less fucosylated glycan compared with the glycans of ΔXT/FT samples (compare percentage values given in Table 3 for fucosylation species $Hex_3Fuc_1HexNAc_4$, of calculated mass 1835.9). Note that xylosylated glycans were not detected in any of these samples (confirmed by LC-ESI-MS of glycans on tryptic fragments produced from the same monoclonal antibody samples; data not shown).

TABLE 3

MALDI-TOF/TOF mass spectroscopy analysis of glycans from antibody produced in ΔXT/FT and KDFX plant hosts: generation analysis.

| | | | | Relative abundance (%) | | | |
|---|---|---|---|---|---|---|---|
| Det. ion $[M + Na]^+$ | Cal. Mass $[M + Na]^+$ | Compositions | Structure | 2015 Sep. 22 ΔXT/FT | 2015 Dec. 8 ΔXT/FT | 2015 Sep. 22 17-7:$T_2$ | 2015 Dec. 8 17-7-26:$T_3$ |
| 1416.7 | 1416.7 | $Hex_3$ $HexNAc_3$ | | 8.5 | 11.1 | 8.5 | 10.5 |
| 1579.8 | 1579.8 | $Hex_5$ $HexNAc_2$ | | 3.7 | 6.0 | 4.1 | 4.8 |
| 1661.8 | 1661.9 | $Hex_3$ $HexNAc_4$ | | 69.3 | 55.8 | 76.1 | 73.6 |
| 1783.9 | 1783.9 | $Hex_6$ $HexNAc_2$ | | 2.0 | 0 | 2.3 | 0 |
| 1835.9 | 1835.9 | $Hex_3$ $Fuc_1$ $HexNAc_4$ | | 10.4 | 14.4 | 1.6 | 2.4 |
| 1988.0 | 1988.0 | $Hex_7$ $HexNAc_2$ | | 2.8 | 4.8 | 3.2 | 2.7 |

TABLE 3-continued

| MALDI-TOF/TOF mass spectroscopy analysis of glycans from antibody produced in ΔXT/FT and KDFX plant hosts: generation analysis. | | | | | | | |
|---|---|---|---|---|---|---|---|
| | | | | Relative abundance (%) | | | |
| Det. ion $[M + Na]^+$ | Cal. Mass $[M + Na]^+$ | Compositions | Structure | 2015 Sep. 22 ΔXT/FT | 2015 Dec. 8 ΔXT/FT | 2015 Sep. 22 17-7:$T_2$ | 2015 Dec. 8 17-7-26:$T_3$ |
| 2192.1 | 2192.1 | $Hex_9$ $HexNAc_2$ | 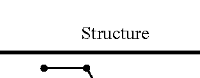 | 1.7 | 3.9 | 1.9 | 2.7 |
| 2396.2 | 2396.2 | $Hex_9$ $HexNAc_2$ | 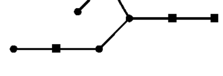 | 1.6 | 4.0 | 2.1 | 3.2 |

Trastuzumab antibody was transiently expressed in ΔXT/FT or KDFX host plants and treated with PNGase A to release glycans, which were analyzed using 4800 MALDI-TOF/TOF (Applied Biosystems). Detected ion and calculated mass for eight glycan species are given in the two leftmost columns. Glycan species composition and structure are given in the 3rd and 4th columns from the left, where filled circles signify mannose (Hex), filled squares signify N-acetylglucosamine (HexNAc), and filled triangle signifies fucose (Fuc). Relative percentage abundances of each glycan species are given for two independent samples pooled from several ΔXT/FT plants (ΔXT/FT), for one sample pooled from several KDFX $T_2$ generation plants of $T_1$-17-7 (17-7:$T_2$), and for one sample pooled from several KDFX $T_3$ generation plants of $T_2$-17-7-26 (17-7-26:$T_3$), with analyses being performed on either 2015 Sep. 22 or 2015 Dec. 8. Xylosylated species were not detected in any sample. Note that the two ΔXT/FT samples contain, on average, 6-fold greater $Hex_3$ $Fuc_1$ $HexNAc_4$ fucosylated glycan species than the KDFX $T_2$ and $T_3$ generation samples.

Thus, the knockdown lines described herein are superior to prior art plant lines for reduced xylosyltransferase and fucosyltransferase activities.

Figure 13:
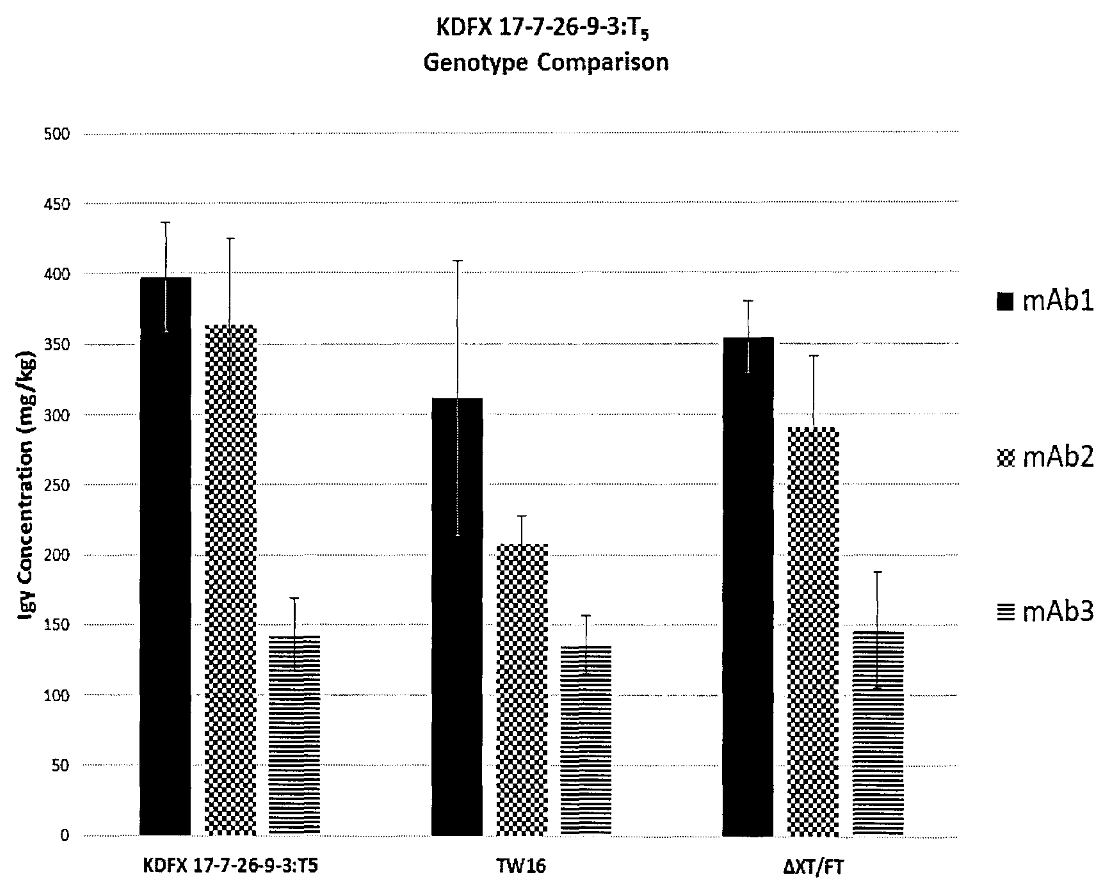
FIG. 13 shows antibody expression in $T_5$ generation offspring of KDFX 17-7-26-9-3 plant compared with wild-type progenitor (TW16) and ΔXT/FT plant lines. Three different monoclonal antibodies (mAb1-3) were transiently expressed in several $T_5$ offspring plants from KDFX $T_4$ plant 17-7-26-9-3, in wild-type *N. benthamiana* (USDA PI 555478, aka TW16) and in the ΔXT/FT line of Strasser et al. (2008). All plants were seeded on the same date and grown in a greenhouse in soil, then vacuum infiltrated with cocktails of *Agrobacterium tumefaciens* strains harboring expression vectors for three different mAbs (pPFC0058, pPFC0904 and pPFC0607) all at $OD_{600}$=0.2. Total leaves were harvested from plants for each treatment after 7 days, homogenized in buffer, extracts were clarified by centrifugation, and mAb expression was measured using a BLItz biosensor unit (fortéBio/Pall) equipped with protein A biosensor tips. Average mAb expression (mg mAb/kg fresh weight) +/− standard errors are given for 4 plants per treatment.

Lastly, antibody expression in $T_5$ generation offspring from plant 17-7-26-9-3 was compared with wild-type progenitor (TW16) and ΔXT/FT plant lines. Three different monoclonal antibodies (mAb1-3) were transiently expressed in several plants from this generation and compared with expression in wild-type *N. benthamiana* (USDA PI 555478, aka TW16) and ΔXT/FT plants (see FIG. 13). All plants were seeded on the same date and grown in a greenhouse in soil, then vacuum infiltrated with cocktails of *Agrobacterium tumefaciens* strains harboring expression vectors for three different mAbs (using vectors pPFC0058, pPFC0904 and pPFC0607), all at $OD_{600}$=0.2. Total leaves were harvested from plants for each treatment after 7 days, homogenized in buffer, extracts were clarified by centrifugation, and mAb expression was measured using a BLItz biosensor unit (fortéBio/Pall) equipped with protein A biosensor tips. Average mAb expression (mg mAb/kg fresh weight) +/− standard errors are given for 4 plants per antibody treatment. As can be seen in the figure, each of the 3 mAbs were expressed in progeny of $T_4$ generation plant 17-7-26-9-3 as well as or better than in either of the other 2 plant lines.

TABLE 4

| Sequences | | |
|---|---|---|
| SEQ ID NO: 1 | pPFC1408 T-DNA sequence | ctgatgggctgcctgtatcgagtggtgattttgtgccgagctgccggtcg<br>gggagctgttggctggctggtggcaggatatattgtggtgtaaacaaatt<br>gacgcttagacaacttaataacacattgcggacgtttttaatgtactgat<br>taatggcgcgccgtcgacgatcatgagcggagaattaagggagtcacgtt<br>atgacccccgccgatgacgcgggacaagccgttttacgtttggaactgac<br>agaaccgcaacgttgaaggagccactcagccgcgggtttctggagtttaa<br>tgagctaagcacatacgtcagaaaccattattgcgcgttcaaaagtcgcc<br>taaggtcactatcagctagcaaatatttcttgtcaaaaatgctccactga<br>cgttccataaattcccctcggtatccaattagagtctcatattcactctc<br>aatccaaataatctgcaccggatctggatcgtttcgcatgattgaacaag<br>atggattgcacgcaggttctccggccgcttgggtggagaggctattcggc<br>tatgactgggcacaacagacaatcggctgctctgatgccgccgtgttccg<br>gctgtcagcgcaggggcgcccggttctttttgtcaagaccgacctgtccg<br>gtgccctgaatgaactgcaggacgaggcagcgcggctatcgtggctggcc<br>acgacgggcgttccttgcgcagctgtgctcgacgttgtcactgaagcggg<br>aagggactggctgctattgggcgaagtgccggggcaggatctcctgtcat<br>ctcaccttgctcctgccgagaaagtatccatcatggctgatgcaatgcgg<br>cggctgcatacgcttgatccggctacctgcccattcgaccaccaagcgaa<br>acatcgcatcgagcgagcacgtactcggatggaagccggtcttgtcgatc<br>aggatgatctggacgaagagcatcaggggctcgcgccagccgaactgttc<br>gccaggctcaaggcgcgcatgcccgacggcgaggatctcgtcgtgaccca<br>tggcgatgcctgcttgccgaatatcatggtggaaaatggccgcttttctg<br>gattcatcgactgtggccggctgggtgtggcggaccgctatcaggacata<br>gcgttggctacccgtgatattgctgaagagcttggcggcgaatgggctga<br>ccgcttcctcgtgctttacggtatcgccgctcccgattcgcagcgcatcg<br>ccttctatcgccttcttgacgagttcttctgagcgggactctggggttcg<br>aaatgaccgaccaagcgacgcccaacctgccatcacgagatttcgattcc<br>accgccgccttctatgaaaggttgggcttcggaatcgttttccgggacgc<br>cggctggatgatcctccagcgcggggatctcatgctggagttcttcgccc<br>acgggatctctgcggaacaggcggtcgaaggtgccgatatcattacgaca<br>gcaacggccgacaagcacaacgccacgatcctgagcgacaatatgatcgg |

TABLE 4-continued

| Sequences |
|---|
| gcccggcgtccacatcaacggcgtcggcggcgactgcccaggcaagaccg<br>agatgcaccgcgatatcttgctgcgttcggatattttcgtggagttcccg<br>ccacagacccggatgatccccgatcgttcaaacatttggcaataaagttt<br>cttaagattgaatcctgttgccggtcttgcgatgattatcatataatttc<br>tgttgaattacgttaagcatgtaataattaacatgtaatgcatgacgtta<br>tttatgagatgggtttttatgattagagtcccgcaattatacatttaata<br>cgcgatagaaaacaaaatatagcgcgcaaactaggataaattatcgcgcg<br>cggtgtcatctatgttactagatcgggcctgcaggggggtccccaccaggt<br>ggtcgacctcgagaacatggtggagcacgacactctcgtctactccaaga<br>atatcaaagatacagtctcagaagaccaaagggctattgagacttttcaa<br>caaagggtaatatcgggaaacctcctcggattccattgcccagctatctg<br>tcacttcatcaaaaggacagtagaaaaggaaggtggcacctacaaatgcc<br>atcattgcgataaaggaaaggctatcgttcaagatgcctctgccgacagt<br>ggtcccaaagatggacccccacccacgaggagcatcgtggaaaaagaaga<br>cgttccaaccacgtcttcaaagcaagtggattgatgtgatatctccactg<br>acgtaagggatgacgcacaatcccactatccttcgcaagacccttcctct<br>atataaggaagttcatttcatttggagaggaccctcgaccaagcttctag<br>attagcaatgaagagcaagtatttgattccataaagagctgggccttaaa<br>ccactcggagtgcaaattaaatgtaattagtggattgtttgcccacatgt<br>ccatgaaagagcaagttcgagcaatccaagatgcttttgtcattgttggt<br>gctcatggagcaggtctaacccacatagtttctgcagcaccaaaagctgt<br>aatactagaaattataagcagcgaatataggcgcccccattttgctctga<br>ttgctcaatggaaaggattggagtaccatcccatatatttggaggggtct<br>tatgcggatccactgcacggtatgctcctcttcttgttcatggtcatgat<br>ccttatatgagcagggaaagtccagtttagacttgtagttagttactctt<br>cgttataggatttggatttcttgcgtgtttatggttttagtttccctcct<br>ttgatgaataaaattgaatcttgtatgagtttcatatccatgttgtgaat<br>ctttttgcagacgcagctaggaccgcataagacccctccaaatatatggg<br>atggtactccaatcctttccattgagcaatcagagcaaaatgggggcgcc<br>tatattcgctgcttataatttctagtattacagcttttggtgctgcagaa<br>actatgtgggttagacctgctccatgagcaccaacaatgacaaaagcatc<br>ttggattgctcgaacttgctctttcatggacatgtgggcaaacaatccac<br>taattacatttaatttgcactccgagtggtttaaggcccagctctttatg<br>gaatcaaatacttgctcttcattgctaatctagagctcgaccggtcgatg<br>agctaagctagctatatcatcaatttatgtattacacataatatcgcact<br>cagtctttcatctacggcaatgtaccagctgatataatcagttattgaaa<br>tatttctgaatttaaacttgcatcaataaatttatgtttttgcttggact<br>ataatacctgacttgttattttatcaataaatatttaaactatatttctt<br>tcaagatactcgaggcgatcgcataccagagaccgggtaccactagtaac<br>atggtggagcacgacactctcgtctactccaagaatatcaaagatacagt<br>ctcagaagaccaaagggctattgagacttttcaacaaagggtaatatcgg<br>gaaacctcctcggattccattgcccagctatctgtcacttcatcaaaagg<br>acagtagaaaaggaaggtggcacctacaaatgccatcattgcgataaagg<br>aaaggctatcgttcaagatgcctctgccgacagtggtcccaaagatggac<br>ccccacccacgaggagcatcgtggaaaaagaagacgttccaaccacgtct<br>tcaaagcaagtggattgatgtgatatctccactgacgtaagggatgacgc<br>acaatcccactatccttcgcaagacccttcctctatataaggaagttcat<br>ttcatttggagaggacgtacgccctcgaccaagctttagaggatccttgg<br>cagcggctttcatttctaattgtggtgctcgcaacttccgtttgcaagct<br>ttagaagcccttgaaagggcaaatatcagaattgactcttatggaagttg<br>tcatcataacagggatggaagagttgacaaagtggcagcactgaagcgtt<br>accagtttagcctggcttttgggaattctaatgaggaggactatgtaact<br>gaaaaattctttcagtctctggtagctgggtcaatccctgtggtggttgg<br>tgctccaaacatccaagactttgcgccttctcctaattcagttttacaca<br>ttaaagagataaaagatgctgaatcaattgccaataccatgaagtacctt<br>gctcaaaaccctattgcatataatgagtcattaaggtggaagtttgaggg<br>cccatctgatggatccactgcacggtatgctcctcttcttgttcatggtc<br>atgatccttatatgagcagggaaagtccagtttagacttgtagttagtta<br>ctcttcgttataggatttggatttcttgcgtgtttatggttttagtttcc<br>ctcctttgatgaataaaattgaatcttgtatgagtttcatatccatgttg<br>tgaatctttttgcagacgcagctaggtccggatccatcagatgggccctc<br>aaacttccaccttaatgactcattatatgcaatagggttttgagcaaggt<br>acttcatggtattggcaattgattcagcatcttttatctctttaatgtgt<br>aaaactgaattaggagaaggcgcaaagtcttggatgtttggagcaccaac<br>caccacagggattgacccagctaccagagactgaaagaatttttcagtta<br>catagtcctcctcattagaattcccaaaagccaggctaaactggtaacgc<br>ttcagtgctgccactttgtcaactcttccatccctgttatgatgacaact<br>tccataagagtcaattctgatatttgccctttcaagggcttctaaagctt<br>gcaaacggaagttgcgagcaccacaattagaaatgaaagccgctgccacg<br>tacgcctaggcgatgagctaagctagctatatcatcaatttatgtattac<br>acataatatcgcactcagtctttcatctacggcaatgtaccagctgatat<br>aatcagttattgaaatatttctgaatttaaacttgcatcaataaatttat<br>gtttttgcttggactataatacctgacttgttattttatcaataaatatt<br>taaactatatttctttcaagatactagttgtacaatcgatggccggcctt<br>aattaaagattgtcgtttcccgccttcagtttaaactatcagtgtttgac<br>aggatatattggcgggtaaacctaagagaaaagagcgtttattagaataa<br>tcggatatttaaaagggcgtgaaaaggtttatccgttcgtccatttgtat<br>gtgcatgccaaccacagg |

TABLE 4-continued

| Sequences | | |
|---|---|---|
| SEQ ID NO: 2 | XylT sense (from pPFC1408) | tctagattagcaatgaagagcaagtatttgattccataaagagctgggcct taaaccactcggagtgcaaattaaatgtaattagtggattgtttgcccaca tgtccatgaaagagcaagttcgagcaatccaagatgcttttgtcattgttg gtgctcatggagcaggtctaacccacatagtttctgcagcaccaaaagctg taatactagaaattataagcagcgaatataggcgcccccattttgctctga ttgctcaatggaaaggattggagtaccatcccatatatttggaggggtctt atgcggatcc |
| SEQ ID NO: 3 | IVS (from pPFC1408) | actgcacggtatgctcctcttcttgttcatggtcatgatccttatatgagc agggaaagtccagtttagacttgtagttagttactcttcgttataggattt ggatttcttgcgtgtttatggttttagtttccctcctttgatgaataaaat tgaatcttgtatgagtttcatatccatgttgtgaatctttttgcagacgca gctagg |
| SEQ ID NO: 4 | XylT antisense (from pPFC1408) | accgcataagacccctccaaatatatgggatggtactccaatcctttccat tgagcaatcagagcaaaatgggggcgcctatattcgctgcttataatttct agtattacagcttttggtgctgcagaaactatgtgggttagacctgctcca tgagcaccaacaatgacaaaagcatcttggattgctcgaacttgctctttc atggacatgtgggcaaacaatccactaattacatttaatttgcactccgag tggtttaaggcccagctctttatggaatcaaatacttgctcttcattgcta atctagagctc |
| SEQ ID NO: 5 | FucT sense (from pPFC1408) | ggatccttggcagcggctttcatttctaattgtggtgctcgcaacttccgt ttgcaagctttagaagcccttgaaagggcaaatatcagaattgactcttat ggaagttgtcatcataacagggatggaagagttgacaaagtggcagcactg aagcgttaccagtttagcctggcttttgggaattctaatgaggaggactat gtaactgaaaaattctttcagtctctggtagctgggtcaatccctgtggtg gttggtgctccaaacatccaagactttgcgccttctcctaattcagtttta cacattaaagagataaaagatgctgaatcaattgccaataccatgaagtac cttgctcaaaaccctattgcatataatgagtcattaaggtggaagtttgag ggcccatctgatggattc |
| SEQ ID NO: 6 | FucT anti-sense(from pPFC1408) | ggatccatcagatgggccctcaaacttccaccttaatgactcattatatgc aatagggttttgagcaaggtacttcatggtattggcaattgattcagcatc ttttatctctttaatgtgtaaaactgaattaggagaaggcgcaaagtcttg gatgtttggagcaccaaccaccacagggattgacccagctaccagagactg aaagaatttttcagttacatagtcctcctcattagaattcccaaaagccag gctaaactggtaacgcttcagtgctgccactttgtcaactcttccatccct gttatgatgacaacttccataagagtcaattctgatatttgccctttcaag ggcttctaaagcttgcaaacggaagttgcgagcaccacaattagaaatgaa agccgctgccacgtacgcctagg |
| SEQ ID NO: 7 | TD-RB-F1 | ggccggccttaattaaagatt |
| SEQ ID NO: 8 | KFX-Ins1-3G1 | aaactttccgtgcttctcca |
| SEQ ID NO: 9 | KFX-Ins1-5G1 | ttgcactttgtgtgggaatg |
| SEQ ID NO: 10 | KFX-Ins2-3G1 | gcatgtccacttgacacacc |
| SEQ ID NO: 11 | KFX-Ins2-5G1 | gacctaaatcgtgggtttatgc |
| SEQ ID NO: 12 | KFX-Ins3-3G1 | aaggggaaccggtctagttg |
| SEQ ID NO: 13 | KFX-Ins3-5G66 | tctgccattcaccacttccatcc |
| SEQ ID NO: 14 | TD-PXT-F3 | ggtatgctcctcttcttgttc |
| SEQ ID NO: 15 | KDFX Insert 1 5171 BP | ataacacattgcggacgtttttaatgtactgattaatggcgcgccgtcgac gatcatgagcggagaattaagggagtcacgttatgacccccgccgatgacg cgggacaagccgttttacgtttggaactgacagaaccgcaacgttgaagga gccactcagccgcgggtttctggagtttaatgagctaagcacatacgtcag aaaccattattgcgcgttcaaaagtcgcctaaggtcactatcagctagcaa atatttcttgtcaaaaatgctccactgacgttccataaattcccctcggta tccaattagagtctcatattcactctcaatccaaataatctgcaccggatc tggatcgtttcgcatgattgaacaagatggattgcacgcaggttctccggc cgcttgggtggagaggctattcggctatgactgggcacaacagacaatcgg ctgctctgatgccgccgtgttccggctgtcagcgcaggggcgcccggttct tttgtcaagaccgacctgtccggtgccctgaatgaactgcaggacgaggc |

TABLE 4-continued

| Sequences |
| --- |
| agcgcggctatcgtggctggccacgacgggcgttccttgcgcagctgtgct<br>cgacgttgtcactgaagcgggaagggactggctgctattgggcgaagtgcc<br>ggggcaggatctcctgtcatctcaccttgctcctgccgagaaagtatccat<br>catggctgatgcaatgcggcggctgcatacgcttgatccggctacctgccc<br>attcgaccaccaagcgaaacatcgcatcgagcgagcacgtactcggatgga<br>agccggtcttgtcgatcaggatgatctggacgaagagcatcaggggctcgc<br>gccagccgaactgttcgccaggctcaaggcgcgcatgcccgacggcgagga<br>tctcgtcgtgacccatggcgatgcctgcttgccgaatatcatggtggaaaa<br>tggccgcttttctggattcatcgactgtggccggctgggtgtggcggaccg<br>ctatcaggacatagcgttggctacccgtgatattgctgaagagcttggcgg<br>cgaatgggctgaccgcttcctcgtgctttacggtatcgccgctcccgattc<br>gcagcgcatcgccttctatcgccttcttgacgagttcttctgagcgggact<br>ctggggttcgaaatgaccgaccaagcgacgcccaacctgccatcacgagat<br>ttcgattccaccgccgccttctatgaaaggttgggcttcggaatcgttttc<br>cgggacgccggctggatgatcctccagcgcggggatctcatgctggagttc<br>ttcgcccacgggatctctgcggaacaggcggtcgaaggtgccgatatcatt<br>acgacagcaacggccgacaagcacaacgccacgatcctgagcgacaatatg<br>atcgggcccggcgtccacatcaacggcgtcggcggcgactgcccaggcaag<br>accgagatgcaccgcgatatcttgctgcgttcggatattttcgtggagttc<br>ccgccacagacccggatgatccccgatcgttcaaacatttggcaataaagt<br>ttcttaagattgaatcctgttgccggtcttgcgatgattatcatataattt<br>ctgttgaattacgttaagcatgtaataattaacatgtaatgcatgacgtta<br>tttatgagatgggtttttatgattagagtcccgcaattatacatttaatac<br>gcgatagaaaacaaaatatagcgcgcaaactaggataaattatcgcgcgcg<br>gtgtcatctatgttactagatcgggcctgcaggggggtccccaccaggtggt<br>cgacctcgagaacatggtggagcacgacactctcgtctactccaagaatat<br>caaagatacagtctcagaagaccaaagggctattgagacttttcaacaaag<br>ggtaatatcgggaaacctcctcggattccattgcccagctatctgtcactt<br>catcaaaaggacagtagaaaaggaaggtggcacctacaaatgccatcattg<br>cgataaaggaaaggctatcgttcaagatgcctctgccgacagtggtcccaa<br>agatggacccccacccacgaggagcatcgtggaaaaagaagacgttccaac<br>cacgtcttcaaagcaagtggattgatgtgatatctccactgacgtaaggga<br>tgacgcacaatcccactatccttcgcaagacccttcctctatataaggaag<br>ttcatttcatttggagaggaccctcgaccaagcttctagattagcaatgaa<br>gagcaagtatttgattccataaagagctgggccttaaaccactcggagtgc<br>aaattaaatgtaattagtggattgtttgcccacatgtccatgaaagagcaa<br>gttcgagcaatccaagatgcttttgtcattgttggtgctcatggagcaggt<br>ctaacccacatagtttctgcagcaccaaaagctgtaatactagaaattata<br>agcagcgaatataggcgcccccattttgctctgattgctcaatggaaagga<br>ttggagtaccatcccatatatttggaggggtcttatgcggatccactgcac<br>ggtatgctcctcttcttgttcatggtcatgatccttatatgagcagggaaa<br>gtccagtttagacttgtagttagttactcttcgttataggatttggatttc<br>ttgcgtgtttatggttttagtttccctcctttgatgaataaaattgaatct<br>tgtatgagtttcatatccatgttgtgaatctttttgcagacgcagctagga<br>ccgcataagacccctccaaatatatgggatggtactccaatcctttccatt<br>gagcaatcagagcaaaatgggggcgcctatattcgctgcttataatttcta<br>gtattacagcttttggtgctgcagaaactatgtgggttagacctgctccat<br>gagcaccaacaatgacaaaagcatcttggattgctcgaacttgctctttca<br>tggacatgtgggcaaacaatccactaattacatttaatttgcactccgagt<br>ggtttaaggcccagctctttatggaatcaaatacttgctcttcattgctaa<br>tctagagctcgaccggtcgatgagctaagctagctatatcatcaatttatg<br>tattacacataatatcgcactcagtctttcatctacggcaatgtaccagct<br>gatataatcagttattgaaatatttctgaatttaaacttgcatcaataaat<br>ttatgtttttgcttggactataatacctgacttgttattttatcaataaat<br>atttaaactatatttctttcaagatactcgaggcgatcgcataccagagac<br>cgggtaccactagtaacatggtggagcacgacactctcgtctactccaaga<br>atatcaaagatacagtctcagaagaccaaagggctattgagacttttcaac<br>aaagggtaatatcgggaaacctcctcggattccattgcccagctatctgtc<br>acttcatcaaaaggacagtagaaaaggaaggtggcacctacaaatgccatc<br>attgcgataaaggaaaggctatcgttcaagatgcctctgccgacagtggtc<br>ccaaagatggacccccacccacgaggagcatcgtggaaaaagaagacgttc<br>caaccacgtcttcaaagcaagtggattgatgtgatatctccactgacgtaa<br>gggatgacgcacaatcccactatccttcgcaagacccttcctctatataag<br>gaagttcatttcatttggagaggacgtacgccctcgaccaagctttagagg<br>atccttggcagcggctttcatttctaattgtggtgctcgcaacttccgttt<br>gcaagctttagaagcccttgaaagggcaaatatcagaattgactcttatgg<br>aagttgtcatcataacagggatggaagagttgacaaagtggcagcactgaa<br>gcgttaccagtttagcctggcttttgggaattctaatgaggaggactatgt<br>aactgaaaaattctttcagtctctggtagctgggtcaatccctgtggtggt<br>tggtgctccaaacatccaagactttgcgccttctcctaattcagttttaca<br>cattaaagagataaaagatgctgaatcaattgccaataccatgaagtacct<br>tgctcaaaaccctattgcatataatgagtcattaaggtggaagtttgaggg<br>cccatctgatggatccactgcacggtatgctcctcttcttgttcatggtca<br>tgatccttatatgagcagggaaagtccagtttagacttgtagttagttact<br>cttcgttataggatttggatttcttgcgtgtttatggttttagtttccctc<br>ctttgatgaataaaattgaatcttgtatgagtttcatatccatgttgtgaa<br>tctttttgcagacgcagctaggtccggatccatcagatgggccctcaaact<br>tccaccttaatgactcattatatgcaatagggttttgagcaaggtacttca |

TABLE 4-continued

| | | Sequences |
|---|---|---|
| | | tggtattggcaattgattcagcatcttttatctctttaatgtgtaaaactg aattaggagaaggcgcaaagtcttggatgtttggagcaccaaccaccacag ggattgacccagctaccagagactgaaagaattttcagttacatagtcct cctcattagaattcccaaaagccaggctaaactggtaacgcttcagtgctg ccactttgtcaactcttccatccctgttatgatgacaacttccataagagt caattctgatatttgccctttcaagggcttctaaagcttgcaaacggaagt tgcgagcaccacaattagaaatgaaagccgctgccacgtacgcctaggcga tgagctaagctagctatatcatcaatttatgtattacacataatatcgcac tcagtctttcatctacggcaatgtaccagctgatataatcagttattgaaa tatttctgaatttaaacttgcatcaataaatttatgtttttgcttggacta taatacctgacttgttattttatcaataaatatttaaactatatttctttc aagatactagttgtacaatcgatggccggccttaattaaagattgtcgttt cccgccttcagtttaaacta |
| SEQ ID NO: 16 | KDFX Insert 2 10383 BP | tcaaacactgatagtttaaactgaaggcgggaaacgacaatctttaattaa ggccggccatcgattgtacaactagtatcttgaaagaaatatagtttaaat atttattgataaaataacaagtcaggtattatagtccaagcaaaaacataa atttattgatgcaagtttaaattcagaaatatttcaataactgattatatc agctggtacattgccgtagatgaaagactgagtgcgatattatgtgtaata cataaattgatgatatagctagcttagctcatcgcctaggcgtacgtggca gcggctttcatttctaattgtggtgctcgcaacttccgtttgcaagcttta gaagcccttgaaagggcaaatatcagaattgactcttatggaagttgtcat cataacagggatggaagagttgacaaagtggcagcactgaagcgttaccag tttagcctggcttttgggaattctaatgaggaggactatgtaactgaaaaa ttctttcagtctctggtagctgggtcaatccctgtggtggttggtgctcca aacatccaagactttgcgccttctcctaattcagttttacacattaaagag ataaaagatgctgaatcaattgccaataccatgaagtaccttgctcaaaac cctattgcatataatgagtcattaaggtggaagtttgagggcccatctgat ggatccggacctagctgcgtctgcaaaaagattcacaacatggatatgaaa ctcatacaagattcaattttattcatcaaaggagggaaactaaaaccataa acacgcaagaaatccaaatcctataacgaagagtaactaactacaagtcta aactggactttccctgctcatataaggatcatgaccatgaacaagaagagg agcataccgtgcagtggatccatcagatgggccctcaaacttccaccttaa tgactcattatatgcaatagggttttgagcaaggtacttcatggtattggc aattgattcagcatcttttatctctttaatgtgtaaaactgaattaggaga aggcgcaaagtcttggatgtttggagcaccaaccaccacagggattgaccc agctaccagagactgaaagaattttcagttacatagtcctcctcattaga attcccaaaagccaggctaaactggtaacgcttcagtgctgccactttgtc aactcttccatccctgttatgatgacaacttccataagagtcaattctgat atttgccctttcaagggcttctaaagcttgcaaacggaagttgcgagcacc acaattagaaatgaaagccgctgccaaggatcctctaaagcttggtcgagg gcgtacgtcctctccaaatgaaatgaacttccttatatagaggaagggtct tgcgaaggatagtgggattgtgcgtcatcccttacgtcagtggagatatca catcaatccacttgctttgaagacgtggttggaacgtcttctttttccacg atgctcctcgtgggtgggggtccatctttgggaccactgtcggcagaggca tcttgaacgatagcctttcctttatcgcaatgatggcatttgtaggtgcca ccttcctttctactgtccttttgatgaagtgacagatagctgggcaatgg aatccgaggaggtttcccgatattaccctttgttgaaaagtctcaatagcc ctttggtcttctgagactgtatctttgatattcttggagtagacgagagtg tcgtgctccaccatgttactagtggtacccggtctctggtatgcgatcgcc tcgagtatcttgaaagaaatatagtttaaatatttattgataaaataacaa gtcaggtattatagtccaagcaaaaacataaatttattgatgcaagtttaa attcagaaatatttcaataactgattatatcagctggtacattgccgtaga tgaaagactgagtgcgatattatgtgtaatacataaattgatgatatagct agcttagctcatcgaccggtcgagctctagattagcaatgaagagcaagta tttgattccataaagagctgggccttaaaccactcggagtgcaaattaaat gtaattagtggattgtttgcccacatgtccatgaaagagcaagttcgagca atccaagatgcttttgtcattgttggtgctcatggagcaggtctaacccac atagtttctgcagcaccaaaagctgtaatactagaaattataagcagcgaa tataggcgcccccattttgctctgattgctcaatggaaaggattggagtac catcccatatatttggaggggtcttatgcggtcctagctgcgtctgcaaaa agattcacaacatggatatgaaactcatacaagattcaattttattcatca aaggagggaaactaaaaccataaacacgcaagaaatccaaatcctataacg aagagtaactaactacaagtctaaactggactttccctgctcatataagga tcatgaccatgaacaagaagaggagcataccgtgcagtggatccgcataag acccctccaaatatatgggatggtactccaatcctttccattgagcaatca gagcaaaatgggggcgcctatattcgctgcttataatttctagtattacag cttttggtgctgcagaaactatgtgggttagacctgctccatgagcaccaa caatgacaaaagcatcttggattgctcgaacttgctctttcatggacatgt gggcaaacaatccactaattacatttaatttgcactccgagtggtttaagg cccagctctttatggaatcaaatacttgctcttcattgctaatctagaagc ttggtcgagggtcctctccaaatgaaatgaacttccttatatagaggaagg gtcttgcgaaggatagtgggattgtgcgtcatcccttacgtcagtggagat atcacatcaatccacttgctttgaagacgtggttggaacgtcttctttttc cacgatgctcctcgtgggtgggggtccatctttgggaccactgtcggcaga ggcatcttgaacgatagcctttcctttatcgcaatgatggcatttgtaggt gccaccttcctttctactgtccttttgatgaagtgacagatagctgggca atggaatccgaggaggtttcccgatattaccctttgttgaaaagtctcaat |

TABLE 4-continued

| Sequences |
|---|
| agccctttggtcttctgagactgtatctttgatattcttggagtagacgag<br>agtgtcgtgctccaccatgttctcgaggtcgaccacctggtggggaccccc<br>tgcaggcccgatctagtaacatagatgacaccgcgcgcgataatttatcct<br>agtttgcgcgctatattttgttttctatcgcgtattaaatgtataattgcg<br>ggactctaatcataaaaacccatctcataaataacgtcatgcattacatgt<br>taattattacatgcttaacgtaattcaacagaaattatatgataatcatcg<br>caagaccggcaacaggattcaatcttaagaaactttattgccaaatgtttg<br>aacgatcggggatcatccgggtctgtggcgggaactccacgaaaatatccg<br>aacgcagcaagatatcgcggtgcatctcggtcttgcctgggcagtcgccgc<br>cgacgccgttgatgtggacgccgggcccgatcatattgtcgctcaggatcg<br>tggcgttgtgcttgtcggccgttgctgtcgtaatgatatcggcaccttcga<br>ccgcctgttccgcagagatcccgtgggcgaagaactccagcatgagatccc<br>cgcgctggaggatcatccagccggcgtcccggaaaacgattccgaagccca<br>acctttcatagaaggcggcggtggaatcgaaatctcgtgatggcaggttgg<br>gcgtcgcttggtcggtcatttcgaaccccagagtcccgctcagaagaactc<br>gtcaagaaggcgatagaaggcgatgcgctgcgaatcgggagcggcgatacc<br>gtaaagcacgaggaagcggtcagcccattcgccgccaagctcttcagcaat<br>atcacgggtagccaacgctatgtcctgatagcggtccgccacacccagccg<br>gccacagtcgatgaatccagaaaagcggccattttccaccatgatattcgg<br>caagcaggcatcgccatgggtcacgacgagatcctcgccgtcgggcatgcg<br>cgccttgagcctggcgaacagttcggctggcgcgagcccctgatgctcttc<br>gtccagatcatcctgatcgacaagaccggcttccatccgagtacgtgctcg<br>ctcgatgcgatgtttcgcttggtggtcgaatgggcaggtagccggatcaag<br>cgtatgcagccgccgcattgcatcagccatgatggatactttctcggcagg<br>agcaaggtgagatgacaggagatcctgccccggcacttcgcccaatagcag<br>ccagtcccttcccgcttcagtgacaacgtcgagcacagctgcgcaaggaac<br>gcccgtcgtggccagccacgatagccgcgctgcctcgtcctgcagttcatt<br>cagggcaccggacaggtcggtcttgacaaaaagaaccgggcgcccctgcgc<br>tgacagccggaacacggcggcatcagagcagccgattgtctgttgtgccca<br>gtcatagccgaatagcctctccacccaagcggccggagaacctgcgtgcaa<br>tccatcttgttcaatcatgcgaaacgatccagatccggtgcagattatttg<br>gattgagagtgaatatgagactctaattggataccgaggggaatttatgga<br>acgtcagtggagcatttttgacaagaaatatttgctagctgatagtgacct<br>taggcgacttttgaacgcgcaataatggtttctgacgtatgtgcttagctc<br>attaaactccagaaacccgcggctgagtggctccttcaacgttgcggttct<br>gtcagttccaaacgtaaaacggcttgtcccgcgtcatcggcgggggtcata<br>acgtgactcccttaattctccgctcatgatcgtcgacggcgcgccattaat<br>cagtacattaaaaacgtccgcaatgtgttattaagttgtctaagcgtcaat<br>ttgtttaataacacattgcggacgtttttaatgtactgattaatggcgcgc<br>cgtcgacgatcatgagcggagaattaagggagtcacgttatgacccccgcc<br>gatgacgcgggacaagccgttttacgtttggaactgacagaaccgcaacgt<br>tgaaggagccactcagccgcgggtttctggagtttaatgagctaagcacat<br>acgtcagaaaccattattgcgcgttcaaaagtcgcctaaggtcactatcag<br>ctagcaaatatttcttgtcaaaaatgctccactgacgttccataaattccc<br>ctcggtatccaattagagtctcatattcactctcaatccaaataatctgca<br>ccggatctggatcgtttcgcatgattgaacaagatggattgcacgcaggtt<br>ctccggccgcttgggtggagaggctattcggctatgactgggcacaacaga<br>caatcggctgctctgatgccgccgtgttccggctgtcagcgcaggggcgcc<br>cggttctttttgtcaagaccgacctgtccggtgccctgaatgaactgcagg<br>acgaggcagcgcggctatcgtggctggccacgacgggcgttccttgcgcag<br>ctgtgctcgacgttgtcactgaagcgggaagggactggctgctattgggcg<br>aagtgccggggcaggatctcctgtcatctcaccttgctcctgccgagaaag<br>tatccatcatggctgatgcaatgcggcggctgcatacgcttgatccggcta<br>cctgcccattcgaccaccaagcgaaacatcgcatcgagcgagcacgtactc<br>ggatggaagccggtcttgtcgatcaggatgatctggacgaagagcatcagg<br>ggctcgcgccagccgaactgttcgccaggctcaaggcgcgcatgcccgacg<br>gcgaggatctcgtcgtgacccatggcgatgcctgcttgccgaatatcatgg<br>tggaaaatggccgcttttctggattcatcgactgtggccggctgggtgtgg<br>cggaccgctatcaggacatagcgttggctacccgtgatattgctgaagagc<br>ttggcggcgaatgggctgaccgcttcctcgtgctttacggtatcgccgctc<br>ccgattcgcagcgcatcgccttctatcgccttcttgacgagttcttctgag<br>cgggactctggggttcgaaatgaccgaccaagcgacgcccaacctgccatc<br>acgagatttcgattccaccgccgccttctatgaaaggttgggcttcggaat<br>cgttttccgggacgccggctggatgatcctccagcgcggggatctcatgct<br>ggagttcttcgcccacgggatctctgcggaacaggcggtcgaaggtgccga<br>tatcattacgacagcaacggccgacaagcacaacgccacgatcctgagcga<br>caatatgatcgggcccggcgtccacatcaacggcgtcggcggcgactgccc<br>aggcaagaccgagatgcaccgcgatatcttgctgcgttcggatattttcgt<br>ggagttcccgccacagacccggatgatccccgatcgttcaaacatttggca<br>ataaagtttcttaagattgaatcctgttgccggtcttgcgatgattatcat<br>ataatttctgttgaattacgttaagcatgtaataattaacatgtaatgcat<br>gacgttatttatgagatgggtttttatgattagagtcccgcaattatacat<br>ttaatacgcgatagaaaacaaaatatagcgcgcaaactaggataaattatc<br>gcgcgcggtgtcatctatgttactagatcgggcctgcaggggggtccccacc<br>aggtggtcgacctcgagaacatggtggagcacgacactctcgtctactcca<br>agaatatcaaagatacagtctcagaagaccaaagggctattgagacttttc<br>aacaaagggtaatatcgggaaacctcctcggattccattgcccagctatct<br>gtcacttcatcaaaaggacagtagaaaaggaaggtggcacctacaaatgcc |

TABLE 4-continued

| | | Sequences |
|---|---|---|
| | | atcattgcgataaaggaaaggctatcgttcaagatgcctctgccgacagtg |
| | | gtcccaaagatggacccccacccacgaggagcatcgtggaaaaagaagacg |
| | | ttccaaccacgtcttcaaagcaagtggattgatgtgatatctccactgacg |
| | | taagggatgacgcacaatcccactatccttcgcaagacccttcctctatat |
| | | aaggaagttcatttcatttggagaggaccctcgaccaagcttctagattag |
| | | caatgaagagcaagtatttgattccataaagagctgggccttaaaccactc |
| | | ggagtgcaaattaaatgtaattagtggattgtttgcccacatgtccatgaa |
| | | agagcaagttcgagcaatccaagatgcttttgtcattgttggtgctcatgg |
| | | agcaggtctaacccacatagtttctgcagcaccaaaagctgtaatactaga |
| | | aattataagcagcgaatataggcgcccccattttgctctgattgctcaatg |
| | | gaaaggattggagtaccatcccatatatttggaggggtcttatgcggatcc |
| | | actgcacggtatgctcctcttcttgttcatggtcatgatccttatatgagc |
| | | agggaaagtccagtttagacttgtagttagttactcttcgttataggattt |
| | | ggatttcttgcgtgtttatggttttagtttccctcctttgatgaataaaat |
| | | tgaatcttgtatgagtttcatatccatgttgtgaatctttttgcagacgca |
| | | gctaggaccgcataagacccctccaaatatatgggatggtactccaatcct |
| | | ttccattgagcaatcagagcaaaatgggggcgcctatattcgctgcttata |
| | | atttctagtattacagcttttggtgctgcagaaactatgtgggttagacct |
| | | gctccatgagcaccaacaatgacaaaagcatcttggattgctcgaacttgc |
| | | tctttcatggacatgtgggcaaacaatccactaattacatttaatttgcac |
| | | tccgagtggtttaaggcccagctctttatggaatcaaatacttgctcttca |
| | | ttgctaatctagagctcgaccggtcgatgagctaagctagctatatcatca |
| | | atttatgtattacacataatatcgcactcagtctttcatctacggcaatgt |
| | | accagctgatataatcagttattgaaatatttctgaatttaaacttgcatc |
| | | aataaatttatgtttttgcttggactataatacctgacttgttattttatc |
| | | aataaatatttaaactatatttctttcaagatactcgaggcgatcgcatac |
| | | cagagaccgggtaccactagtaacatggtggagcacgacactctcgtctac |
| | | tccaagaatatcaaagatacagtctcagaagaccaaagggctattgagact |
| | | tttcaacaaagggtaatatcgggaaacctcctcggattccattgcccagct |
| | | atctgtcacttcatcaaaaggacagtagaaaaggaaggtggcacctacaaa |
| | | tgccatcattgcgataaaggaaaggctatcgttcaagatgcctctgccgac |
| | | agtggtcccaaagatggacccccacccacgaggagcatcgtggaaaaagaa |
| | | gacgttccaaccacgtcttcaaagcaagtggattgatgtgatatctccact |
| | | gacgtaagggatgacgcacaatcccactatccttcgcaagacccttcctct |
| | | atataaggaagttcatttcatttggagaggacgtacgccctcgaccaagct |
| | | ttagaggatccttggcagcggctttcatttctaattgtggtgctcgcaact |
| | | tccgtttgcaagctttagaagcccttgaaagggcaaatatcagaattgact |
| | | cttatggaagttgtcatcataacagggatggaagagttgacaaagtggcag |
| | | cactgaagcgttaccagtttagcctggcttttgggaattctaatgaggagg |
| | | actatgtaactgaaaaattctttcagtctctggtagctgggtcaatccctg |
| | | tggtggttggtgctccaaacatccaagactttgcgccttctcctaattcag |
| | | ttttacacattaaagagataaaagatgctgaatcaattgccaataccatga |
| | | agtaccttgctcaaaaccctattgcatataatgagtcattaaggtggaagt |
| | | ttgagggcccatctgatggatccactgcacggtatgctcctcttcttgttc |
| | | atggtcatgatccttatatgagcagggaaagtccagtttagacttgtagtt |
| | | agttactcttcgttataggatttggatttcttgcgtgtttatggttttagt |
| | | ttccctcctttgatgaataaaattgaatcttgtatgagtttcatatccatg |
| | | ttgtgaatctttttgcagacgcagctaggtccggatccatcagatgggccc |
| | | tcaaacttccaccttaatgactcattatatgcaatagggttttgagcaagg |
| | | tacttcatggtattggcaattgattcagcatcttttatctctttaatgtgt |
| | | aaaactgaattaggagaaggcgcaaagtcttggatgtttggagcaccaacc |
| | | accacagggattgacccagctaccagagactgaaagaattttttcagttaca |
| | | tagtcctcctcattagaattcccaaaagccaggctaaactggtaacgcttc |
| | | agtgctgccactttgtcaactcttccatccctgttatgatgacaacttcca |
| | | taagagtcaattctgatatttgccctttcaagggcttctaaagcttgcaaa |
| | | cggaagttgcgagcaccacaattagaaatgaaagccgctgccacgtacgcc |
| | | taggcgatgagctaagctagctatatcatcaatttatgtattacacataat |
| | | atcgcactcagtctttcatctacggcaatgtaccagctgatataatcagtt |
| | | attgaaatatttctgaatttaaacttgcatcaataaatttatgtttttgct |
| | | tggactataatacctgacttgttattttatcaataaatatttaaactatat |
| | | ttctttcaagatactagttgtacaatcgatggccggccttaattaaagatt |
| | | gtcgtttcccgccttcagtttaaactatca |
| SEQ ID | KDFX Insert | aaatcctataacgaagagtaactaactacaagtctaaactggactttccct |
| NO: 17 | 3 5033 BP | gctcatataaggatcatgaccatgaacaagaagaggagcataccgtgcagt |
| | | ggatccgcataagacccctccaaatatatgggatggtactccaatcctttc |
| | | cattgagcaatcagagcaaaatgggggcgcctatattcgctgcttataatt |
| | | tctagtattacagcttttggtgctgcagaaactatgtgggttagacctgct |
| | | ccatgagcaccaacaatgacaaaagcatcttggattgctcgaacttgctct |
| | | ttcatggacatgtgggcaaacaatccactaattacatttaatttgcactcc |
| | | gagtggtttaaggcccagctctttatggaatcaaatacttgctcttcattg |
| | | ctaatctagagctcgaccggtcgatgagctaagctagctatatcatcaatt |
| | | tatgtattacacataatatcgcactcagtctttcatctacggcaatgtacc |
| | | agctgatataatcagttattgaaatatttctgaatttaaacttgcatcaat |
| | | aaatttatgtttttgcttggactataatacctgacttgttattttatcaat |
| | | aaatatttaaactatatttctttcaagatactcgaggcgatcgcataccag |
| | | agaccgggtaccactagtaacatggtggagcacgacactctcgtctactcc |
| | | aagaatatcaaagatacagtctcagaagaccaaagggctattgagactttt |

TABLE 4-continued

| Sequences |
|---|
| caacaaagggtaatatcgggaaacctcctcggattccattgcccagctatc<br>tgtcacttcatcaaaaggacagtagaaaaggaaggtggcacctacaaatgc<br>catcattgcgataaaggaaaggctatcgttcaagatgcctctgccgacagt<br>ggtcccaaagatggacccccacccacgaggagcatcgtggaaaaagaagac<br>gttccaaccacgtcttcaaagcaagtggattgatgtgatatctccactgac<br>gtaagggatgacgcacaatcccactatccttcgcaagacccttcctctata<br>taaggaagttcatttcatttggagaggacgtacgccctcgaccaagcttta<br>gaggatccttggcagcggctttcatttctaattgtggtgctcgcaacttcc<br>gtttgcaagctttagaagcccttgaaagggcaaatatcagaattgactctt<br>atggaagttgtcatcataacagggatggaagagttgacaaagtggcagcac<br>tgaagcgttaccagtttagcctggcttttgggaattctaatgaggaggact<br>atgtaactgaaaaattctttcagtctctggtagctgggtcaatccctgtgg<br>tggttggtgctccaaacatccaagactttgcgccttctcctaattcagttt<br>tacacattaaagagataaaagatgctgaatcaattgccaataccatgaagt<br>accttgctcaaaaccctattgcatataatgagtcattaaggtggaagtttg<br>agggcccatctgatggatccactgcacggtatgctcctcttcttgttcatg<br>gtcatgatccttatatgagcagggaaagtccagtttagacttgtagttagt<br>tactcttcgttataggatttggatttcttgcgtgtttatggttttagtttc<br>cctcctttgatgaataaaattgaatcttgtatgagtttcatatccatgttg<br>tgaatctttttgcagacgcagctaggtccggatccatcagatgggccctca<br>aacttccaccttaatgactcattatatgcaatagggttttgagcaaggtac<br>ttcatggtattggcaattgattcagcatcttttatctctttaatgtgtaaa<br>actgaattaggagaaggcgcaaagtcttggatgtttggagcaccaaccacc<br>acagggattgacccagctaccagagactgaaagaatttttcagttacatag<br>tcctcctcattagaattcccaaaagccaggctaaactggtaacgcttcagt<br>gctgccactttgtcaactcttccatccctgttatgatgacaacttccataa<br>gagtcaattctgatatttgccctttcaagggcttctaaagcttgcaaacgg<br>aagttgcgagcaccacaattagaaatgaaagccgctgccacgtacgcctag<br>gcgatgagctaagctagctatatcatcaatttatgtattacacataatatc<br>gcactcagtctttcatctacggcaatgtaccagctgatataatcagttatt<br>gaaatatttctgaatttaaacttgcatcaataaatttatgtttttgcttgg<br>actataatacctgacttgttattttatcaataaatatttaaactatatttc<br>tttcaagatactagttgtacaatcgatggccggccttaattaaagattgtc<br>gtttcccgccttcagtttaaactatcagtgtttgaatggatatgaaactca<br>tacaagattcaattttattcatcaaaggagggaaactaaaaccataaacac<br>gcaagaaatccaaatcctataacgaagagtaactaactacaagtctaaact<br>ggactttccctgctcatataaggatcatgaccatgaacaagaagaggagca<br>taccgtgcagtggatccgcataagacccctccaaatatatgggatggtact<br>ccaatcctttccattgagcaatcagagcaaaatgggggcgcctatattcgc<br>tgcttataatttctagtattacagcttttggtgctgcagaaactatgtggg<br>ttagacctgctccatgagcaccaacaatgacaaaagcatcttggattgctc<br>gaacttgctctttcatggacatgtgggcaaacaatccactaattacattta<br>atttgcactccgagtggtttaaggcccagctctttatggaatcaaatactt<br>gctcttcattgctaatctagagctcgaccggtcgatgagctaagctagcta<br>tatcatcaatttatgtattacacataatatcgcactcagtctttcatctac<br>ggcaatgtaccagctgatataatcagttattgaaatatttctgaatttaaa<br>cttgcatcaataaatttatgtttttgcttggactataatacctgacttgtt<br>attttatcaataaatatttaaactatatttctttcaagatactcgaggcga<br>tcgcataccagagaccgggtaccactagtaacatggtggagcacgacactc<br>tcgtctactccaagaatatcaaagatacagtctcagaagaccaaagggcta<br>ttgagacttttcaacaaagggtaatatcgggaaacctcctcggattccatt<br>gcccagctatctgtcacttcatcaaaaggacagtagaaaaggaaggtggca<br>cctacaaatgccatcattgcgataaaggaaaggctatcgttcaagatgcct<br>ctgccgacagtggtcccaaagatggacccccacccacgaggagcatcgtgg<br>aaaaagaagacgttccaaccacgtcttcaaagcaagtggattgatgtgata<br>tctccactgacgtaagggatgacgcacaatcccactatccttcgcaagacc<br>cttcctctatataaggaagttcatttcatttggagaggacgtacgccctcg<br>accaagctttagaggatccttggcagcggctttcatttctaattgtggtgc<br>tcgcaacttccgtttgcaagctttagaagcccttgaaagggcaaatatcag<br>aattgactcttatggaagttgtcatcataacagggatggaagagttgacaa<br>agtggcagcactgaagcgttaccagtttagcctggcttttgggaattctaa<br>tgaggaggactatgtaactgaaaaattctttcagtctctggtagctgggtc<br>aatccctgtggtggttggtgctccaaacatccaagactttgcgccttctcc<br>taattcagttttacacattaaagagataaaagatgctgaatcaattgccaa<br>taccatgaagtaccttgctcaaaaccctattgcatataatgagtcattaag<br>gtggaagtttgagggcccatctgatggatccactgcacggtatgctcctct<br>tcttgttcatggtcatgatccttatatgagcagggaaagtccagtttagac<br>ttgtagttagttactcttcgttataggatttggatttcttgcgtgtttatg<br>gttttagtttccctcctttgatgaataaaattgaatcttgtatgagtttca<br>tatccatgttgtgaatctttttgcagacgcagctaggtccggatccatcag<br>atgggccctcaaacttccaccttaatgactcattatatgcaatagggtttt<br>gagcaaggtacttcatggtattggcaattgattcagcatcttttatctctt<br>taatgtgtaaaactgaattaggagaaggcgcaaagtcttggatgtttggag<br>caccaaccaccacagggattgacccagctaccagagactgaaagaattttt<br>cagttacatagtcctcctcattagaattcccaaaagccaggctaaactggt<br>aacgcttcagtgctgccactttgtcaactcttccatccctgttatgatgac<br>aacttccataagagtcaattctgatatttgccctttcaagggcttctaaag<br>cttgcaaacggaagttgcgagcaccacaattagaaatgaaagccgctgcca |

TABLE 4-continued

| Sequences |
| --- |
| cgtacgcctaggcgatgagctaagctagctatatcatcaatttatgtatta<br>cacataatatcgcactcagtctttcatctacggcaatgtaccagctgatat<br>aatcagttattgaaatatttctgaatttaaacttgcatcaataaatttatg<br>tttttgcttggactataatacctgacttgttattttatcaataaatattta<br>aactatatttctttcaagatactagttgtacaatcgatggccggccttaat<br>taaagattgtcgtttcccgccttcagtttaaacta |

DEPOSIT

A deposit of at least 625 seeds of *Nicotiana benthamiana* cultivar KDFX was made with the American Type Culture Collection (ATTC), 10801 University Boulevard, Manassas, Va. 20110 USA on Mar. 17, 2022 pursuant to the Budapest Treaty on the International Recognition of the Deposit of Microorganisms for the Purposes of Patent Procedure, Rule 10.2. The deposit has been assigned ATCC Accession number PTA-127135.

REFERENCES

Aalberse, R. C., V. Koshte and J. G. Clemens, 1981 Immunoglobulin E antibodies that crossreact with vegetable foods, pollen, and Hymenoptera venom. J Allergy Clin Immunol 68: 356-364.

Aalberse, R. C., and R. van Ree, 1997 Crossreactive carbohydrate determinants. Clin Rev Allergy Immunol 15: 375-387.

Aviezer, D., E. Brill-Almon, Y. Shaaltiel, S. Hashmueli, D. Bartfeld et al., 2009 A plant-derived recombinant human glucocerebrosidase enzyme—a preclinical and phase I investigation. PLoS One 4: e4792.

Bevan, M., 1984 Binary *Agrobacterium* vectors for plant transformation. Nucleic Acids Res 12: 8711-8721.

Cox, K. M., J. D. Sterling, J. T. Regan, J. R. Gasdaska, K. K. Frantz et al., 2006 Glycan optimization of a human monoclonal antibody in the aquatic plant *Lemna minor*. Nature Biotechnology 24: 1591-1597.

Garcia-Casado, G., R. Sanchez-Monge, M. J. Chrispeels, A. Armentia, G. Salcedo et al., 1996 Role of complex asparagine-linked glycans in the allergenicity of plant glycoproteins. Glycobiology 6: 471-477.

Strasser, R., J. Stadlmann, M. Schahs, G. Stiegler, H. Quendler et al., 2008 Generation of glyco-engineered *Nicotiana benthamiana* for the production of monoclonal antibodies with a homogeneous human-like N-glycan structure. Plant Biotechnology Journal 6: 392-402.

Tretter, V., F. Altmann, V. Kubelka, L. Marz and W. M. Becker, 1993 Fucose alpha 1,3-linked to the core region of glycoprotein N-glycans creates an important epitope for IgE from honeybee venom allergic individuals. Int Arch Allergy Immunol 102: 259-266.

Ward, B. J., N. Landry, S. Trepanier, G. Mercier, M. Dargis et al., 2014 Human antibody response to N-glycans present on plant-made influenza virus-like particle (VLP) vaccines. Vaccine 32: 6098-6106.

Yamashita K, Kochibe N, Ohkura T, Ueda I and Kobata A. 1985 Fractionation of L-fucose-containing oligosaccharides on immobilized *Aleuria aurantia* lectin J. Biol. Chem. 260: 4688-93.

Zimran, A., E. Brill-Almon, R. Chertkoff, M. Petakov, F. Blanco-Favela et al., 2011 Pivotal trial with plant cell-expressed recombinant glucocerebrosidase, *Taliglucerase alfa*, a novel enzyme replacement therapy for Gaucher disease. Blood 118: 5767-5773.

The invention claimed is:

1. A genetically modified *Nicotiana benthamiana* plant, plant part or plant cell wherein the plant, plant part or plant cell comprises (a) a first T-DNA insertion consisting of the reverse complement of SEQ ID NO: 15;

(b) a second T-DNA insertion consisting of SEQ ID NO: 16; and (c) a third T-DNA insertion consisting of the reverse complement of SEQ ID NO: 17, wherein seeds comprising said first, second, and third T-DNA insertions have been deposited at the ATCC under Accession No. PTA-127135.

2. A method of producing a protein in a plant, comprising:

(a) introducing a nucleic acid molecule encoding the protein into the *Nicotiana benthamiana* plant, plant part or plant cell of claim 1 and (b) growing the plant, plant part or plant cell to obtain a plant that expresses the protein.

3. The method of claim 2, wherein less than 10% of the total glycan on the protein is α1,3-fucosylated glycan and less than 3% of the total glycan on the protein is β1,2-xylosylated glycan.

4. The method of claim 2, wherein the protein is a glycoprotein.

5. The method of claim 2, wherein the protein is an antibody.

* * * * *

SEQUENCE LISTING

<160> NUMBER OF SEQ ID NOS: 38

<210> SEQ ID NO 1
<211> LENGTH: 5418
<212> TYPE: DNA
<213> ORGANISM: Artificial Sequence
<220> FEATURE:
<223> OTHER INFORMATION: Synthetic construct

<400> SEQUENCE: 1
ctgatgggct gcctgtatcg agtggtgatt ttgtgccgag ctgccggtcg gggagctgtt 60
ggctggctgg tggcaggata tattgtggtg taaacaaatt gacgcttaga caacttaata 120
acacattgcg gacgttttta atgtactgat taatggcgcg ccgtcgacga tcatgagcgg 180
agaattaagg gagtcacgtt atgacccccg ccgatgacgc gggacaagcc gttttacgtt 240
tggaactgac agaaccgcaa cgttgaagga gccactcagc cgcgggtttc tggagtttaa 300
tgagctaagc acatacgtca gaaaccatta ttgcgcgttc aaaagtcgcc taaggtcact 360
atcagctagc aaatatttct tgtcaaaaat gctccactga cgttccataa attcccctcg 420
gtatccaatt agagtctcat attcactctc aatccaaata atctgcaccg gatctggatc 480
gtttcgcatg attgaacaag atggattgca cgcaggttct ccggccgctt gggtggagag 540

```
gctattcggc tatgactggg cacaacagac aatcggctgc tctgatgccg ccgtgttccg    600
gctgtcagcg caggggcgcc cggttctttt tgtcaagacc gacctgtccg gtgccctgaa    660
tgaactgcag gacgaggcag cgcggctatc gtggctggcc acgacgggcg ttccttgcgc    720
agctgtgctc gacgttgtca ctgaagcggg aagggactgg ctgctattgg gcgaagtgcc    780
ggggcaggat ctcctgtcat ctcaccttgc tcctgccgag aaagtatcca tcatggctga    840
tgcaatgcgg cggctgcata cgcttgatcc ggctacctgc ccattcgacc accaagcgaa    900
acatcgcatc gagcgagcac gtactcggat ggaagccggt cttgtcgatc aggatgatct    960
ggacgaagag catcaggggc tcgcgccagc cgaactgttc gccaggctca aggcgcgcat   1020
gcccgacggc gaggatctcg tcgtgaccca tggcgatgcc tgcttgccga atatcatggt   1080
ggaaaatggc cgcttttctg gattcatcga ctgtggccgg ctgggtgtgg cggaccgcta   1140
tcaggacata gcgttggcta cccgtgatat tgctgaagag cttggcggcg aatgggctga   1200
ccgcttcctc gtgctttacg gtatcgccgc tcccgattcg cagcgcatcg ccttctatcg   1260
ccttcttgac gagttcttct gagcgggact ctggggttcg aaatgaccga ccaagcgacg   1320
cccaacctgc catcacgaga tttcgattcc accgccgcct tctatgaaag gttgggcttc   1380
ggaatcgttt tccgggacgc cggctggatg atcctccagc gcggggatct catgctggag   1440
ttcttcgccc acgggatctc tgcggaacag gcggtcgaag gtgccgatat cattacgaca   1500
gcaacggccg acaagcacaa cgccacgatc ctgagcgaca atatgatcgg gcccggcgtc   1560
cacatcaacg gcgtcggcgg cgactgccca ggcaagaccg agatgcaccg cgatatcttg   1620
ctgcgttcgg atattttcgt ggagttcccg ccacagaccc ggatgatccc cgatcgttca   1680
aacatttggc aataaagttt cttaagattg aatcctgttg ccggtcttgc gatgattatc   1740
atataatttc tgttgaatta cgttaagcat gtaataatta acatgtaatg catgacgtta   1800
tttatgagat gggtttttat gattagagtc ccgcaattat acatttaata cgcgatagaa   1860
aacaaaatat agcgcgcaaa ctaggataaa ttatcgcgcg cggtgtcatc tatgttacta   1920
gatcgggcct gcagggggtc cccaccaggt ggtcgacctc gagaacatgg tggagcacga   1980
cactctcgtc tactccaaga atatcaaaga tacagtctca gaagaccaaa gggctattga   2040
gacttttcaa caaagggtaa tatcgggaaa cctcctcgga ttccattgcc cagctatctg   2100
tcacttcatc aaaaggacag tagaaaagga aggtggcacc tacaaatgcc atcattgcga   2160
taaaggaaag gctatcgttc aagatgcctc tgccgacagt ggtcccaaag atggaccccc   2220
acccacgagg agcatcgtgg aaaaagaaga cgttccaacc acgtcttcaa agcaagtgga   2280
ttgatgtgat atctccactg acgtaaggga tgacgcacaa tcccactatc cttcgcaaga   2340
cccttcctct atataaggaa gttcatttca tttggagagg accctcgacc aagcttctag   2400
attagcaatg aagagcaagt atttgattcc ataaagagct gggccttaaa ccactcggag   2460
tgcaaattaa atgtaattag tggattgttt gcccacatgt ccatgaaaga gcaagttcga   2520
gcaatccaag atgcttttgt cattgttggt gctcatggag caggtctaac ccacatagtt   2580
tctgcagcac caaaagctgt aatactagaa attataagca gcgaatatag gcgcccccat   2640
tttgctctga ttgctcaatg gaaaggattg gagtaccatc ccatatattt ggaggggtct   2700
tatgcggatc cactgcacgg tatgctcctc ttcttgttca tggtcatgat ccttatatga   2760
gcagggaaag tccagtttag acttgtagtt agttactctt cgttatagga tttggatttc   2820
ttgcgtgttt atggttttag tttccctcct ttgatgaata aaattgaatc ttgtatgagt   2880
```

```
ttcatatcca tgttgtgaat ctttttgcag acgcagctag gaccgcataa gacccctcca   2940
aatatatggg atggtactcc aatcctttcc attgagcaat cagagcaaaa tgggggcgcc   3000
tatattcgct gcttataatt tctagtatta cagcttttgg tgctgcagaa actatgtggg   3060
ttagacctgc tccatgagca ccaacaatga caaaagcatc ttggattgct cgaacttgct   3120
ctttcatgga catgtgggca aacaatccac taattacatt taatttgcac tccgagtggt   3180
ttaaggccca gctctttatg gaatcaaata cttgctcttc attgctaatc tagagctcga   3240
ccggtcgatg agctaagcta gctatatcat caatttatgt attacacata atatcgcact   3300
cagtctttca tctacggcaa tgtaccagct gatataatca gttattgaaa tatttctgaa   3360
tttaaacttg catcaataaa tttatgtttt tgcttggact ataatacctg acttgttatt   3420
ttatcaataa atatttaaac tatatttctt tcaagatact cgaggcgatc gcataccaga   3480
gaccgggtac cactagtaac atggtggagc acgacactct cgtctactcc aagaatatca   3540
aagatacagt ctcagaagac caaagggcta ttgagacttt tcaacaaagg gtaatatcgg   3600
gaaacctcct cggattccat tgcccagcta tctgtcactt catcaaaagg acagtagaaa   3660
aggaaggtgg cacctacaaa tgccatcatt gcgataaagg aaaggctatc gttcaagatg   3720
cctctgccga cagtggtccc aaagatggac ccccacccac gaggagcatc gtggaaaaag   3780
aagacgttcc aaccacgtct tcaaagcaag tggattgatg tgatatctcc actgacgtaa   3840
gggatgacgc acaatcccac tatccttcgc aagacccttc ctctatataa ggaagttcat   3900
ttcatttgga gaggacgtac gccctcgacc aagctttaga ggatccttgg cagcggcttt   3960
catttctaat tgtggtgctc gcaacttccg tttgcaagct ttagaagccc ttgaaagggc   4020
aaatatcaga attgactctt atggaagttg tcatcataac agggatggaa gagttgacaa   4080
agtggcagca ctgaagcgtt accagtttag cctggctttt gggaattcta atgaggagga   4140
ctatgtaact gaaaaattct ttcagtctct ggtagctggg tcaatccctg tggtggttgg   4200
tgctccaaac atccaagact ttgcgccttc tcctaattca gttttacaca ttaaagagat   4260
aaaagatgct gaatcaattg ccaataccat gaagtacctt gctcaaaacc ctattgcata   4320
taatgagtca ttaaggtgga agtttgaggg cccatctgat ggatccactg cacggtatgc   4380
tcctcttctt gttcatggtc atgatcctta tatgagcagg gaaagtccag tttagacttg   4440
tagttagtta ctcttcgtta taggatttgg atttcttgcg tgtttatggt tttagtttcc   4500
ctcctttgat gaataaaatt gaatcttgta tgagtttcat atccatgttg tgaatctttt   4560
tgcagacgca gctaggtccg gatccatcag atgggccctc aaacttccac cttaatgact   4620
cattatatgc aatagggttt tgagcaaggt acttcatggt attggcaatt gattcagcat   4680
cttttatctc tttaatgtgt aaaactgaat taggagaagg cgcaaagtct tggatgtttg   4740
gagcaccaac caccacaggg attgacccag ctaccagaga ctgaaagaat ttttcagtta   4800
catagtcctc ctcattagaa ttcccaaaag ccaggctaaa ctggtaacgc ttcagtgctg   4860
ccactttgtc aactcttcca tccctgttat gatgacaact tccataagag tcaattctga   4920
tatttgccct ttcaagggct tctaaagctt gcaaacggaa gttgcgagca ccacaattag   4980
aaatgaaagc cgctgccacg tacgcctagg cgatgagcta agctagctat atcatcaatt   5040
tatgtattac acataatatc gcactcagtc tttcatctac ggcaatgtac cagctgatat   5100
aatcagttat tgaaatattt ctgaatttaa acttgcatca ataaatttat gtttttgctt   5160
ggactataat acctgacttg ttattttatc aataaatatt taaactatat ttctttcaag   5220
atactagttg tacaatcgat ggccggcctt aattaaagat tgtcgtttcc cgccttcagt   5280
```

ttaaactatc agtgtttgac aggatatatt ggcgggtaaa cctaagagaa aagagcgttt 5340
attagaataa tcggatattt aaaagggcgt gaaaaggttt atccgttcgt ccatttgtat 5400
gtgcatgcca accacagg 5418

<210> SEQ ID NO 2
<211> LENGTH: 316
<212> TYPE: DNA
<213> ORGANISM: Artificial Sequence
<220> FEATURE:
<223> OTHER INFORMATION: Synthetic construct

<400> SEQUENCE: 2
tctagattag caatgaagag caagtatttg attccataaa gagctgggcc ttaaaccact 60
cggagtgcaa attaaatgta attagtggat tgtttgccca catgtccatg aaagagcaag 120
ttcgagcaat ccaagatgct tttgtcattg ttggtgctca tggagcaggt ctaacccaca 180
tagtttctgc agcaccaaaa gctgtaatac tagaaattat aagcagcgaa tataggcgcc 240
cccattttgc tctgattgct caatggaaag gattggagta ccatcccata tatttggagg 300
ggtcttatgc ggatcc 316

<210> SEQ ID NO 3
<211> LENGTH: 210
<212> TYPE: DNA
<213> ORGANISM: Artificial Sequence
<220> FEATURE:
<223> OTHER INFORMATION: Synthetic construct

<400> SEQUENCE: 3
actgcacggt atgctcctct tcttgttcat ggtcatgatc cttatatgag cagggaaagt 60
ccagtttaga cttgtagtta gttactcttc gttataggat ttggatttct tgcgtgttta 120
tggttttagt ttccctcctt tgatgaataa aattgaatct tgtatgagtt tcatatccat 180
gttgtgaatc tttttgcaga cgcagctagg 210

<210> SEQ ID NO 4
<211> LENGTH: 317
<212> TYPE: DNA
<213> ORGANISM: Artificial Sequence
<220> FEATURE:
<223> OTHER INFORMATION: Synthetic construct

<400> SEQUENCE: 4
accgcataag acccctccaa atatatggga tggtactcca atcctttcca ttgagcaatc 60
agagcaaaat gggggcgcct atattcgctg cttataattt ctagtattac agcttttggt 120
gctgcagaaa ctatgtgggt tagacctgct ccatgagcac caacaatgac aaaagcatct 180
tggattgctc gaacttgctc tttcatggac atgtgggcaa acaatccact aattacattt 240
aatttgcact ccgagtggtt taaggcccag ctctttatgg aatcaaatac ttgctcttca 300
ttgctaatct agagctc 317

<210> SEQ ID NO 5
<211> LENGTH: 426
<212> TYPE: DNA
<213> ORGANISM: Artificial Sequence
<220> FEATURE:
<223> OTHER INFORMATION: Synthetic construct

<400> SEQUENCE: 5

```
ggatccttgg cagcggcttt catttctaat tgtggtgctc gcaacttccg tttgcaagct     60

ttagaagccc ttgaaagggc aaatatcaga attgactctt atggaagttg tcatcataac    120

agggatggaa gagttgacaa agtggcagca ctgaagcgtt accagtttag cctggctttt    180

gggaattcta atgaggagga ctatgtaact gaaaaattct ttcagtctct ggtagctggg    240

tcaatccctg tggtggttgg tgctccaaac atccaagact ttgcgccttc tcctaattca    300

gttttacaca ttaaagagat aaaagatgct gaatcaattg ccaataccat gaagtacctt    360

gctcaaaacc ctattgcata taatgagtca ttaaggtgga agtttgaggg cccatctgat    420

ggattc                                                               426


<210> SEQ ID NO 6
<211> LENGTH: 431
<212> TYPE: DNA
<213> ORGANISM: Artificial Sequence
<220> FEATURE:
<223> OTHER INFORMATION: Synthetic construct

<400> SEQUENCE: 6

ggatccatca gatgggccct caaacttcca ccttaatgac tcattatatg caatagggtt     60

ttgagcaagg tacttcatgg tattggcaat tgattcagca tcttttatct ctttaatgtg    120

taaaactgaa ttaggagaag gcgcaaagtc ttggatgttt ggagcaccaa ccaccacagg    180

gattgaccca gctaccagag actgaaagaa tttttcagtt acatagtcct cctcattaga    240

attcccaaaa gccaggctaa actggtaacg cttcagtgct gccactttgt caactcttcc    300

atccctgtta tgatgacaac ttccataaga gtcaattctg atatttgccc tttcaagggc    360

ttctaaagct tgcaaacgga agttgcgagc accacaatta gaaatgaaag ccgctgccac    420

gtacgcctag g                                                         431


<210> SEQ ID NO 7
<211> LENGTH: 21
<212> TYPE: DNA
<213> ORGANISM: Artificial Sequence
<220> FEATURE:
<223> OTHER INFORMATION: Synthetic construct

<400> SEQUENCE: 7

ggccggcctt aattaaagat t                                               21


<210> SEQ ID NO 8
<211> LENGTH: 20
<212> TYPE: DNA
<213> ORGANISM: Artificial Sequence
<220> FEATURE:
<223> OTHER INFORMATION: Synthetic construct

<400> SEQUENCE: 8

aaactttccg tgcttctcca                                                 20


<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9

ttgcactttg tgtgggaatg                                                 20
```

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
gcatgtccac ttgacacacc 20

<210> SEQ ID NO 11
<211> LENGTH: 22
<212> TYPE: DNA
<213> ORGANISM: Artificial Sequence
<220> FEATURE:
<223> OTHER INFORMATION: Synthetic construct

<400> SEQUENCE: 11
gacctaaatc gtgggtttat gc 22

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
aaggggaacc ggtctagttg 20

<210> SEQ ID NO 13
<211> LENGTH: 23
<212> TYPE: DNA
<213> ORGANISM: Artificial Sequence
<220> FEATURE:
<223> OTHER INFORMATION: Synthetic construct

<400> SEQUENCE: 13
tctgccattc accacttcca tcc 23

<210> SEQ ID NO 14
<211> LENGTH: 21
<212> TYPE: DNA
<213> ORGANISM: Artificial Sequence
<220> FEATURE:
<223> OTHER INFORMATION: Synthetic construct

<400> SEQUENCE: 14
ggtatgctcc tcttcttgtt c 21

<210> SEQ ID NO 15
<211> LENGTH: 10342
<212> TYPE: DNA
<213> ORGANISM: Artificial Sequence
<220> FEATURE:
<223> OTHER INFORMATION: Synthetic construct

<400> SEQUENCE: 15
ataacacatt gcggacgttt ttaatgtact gattaatggc gcgccgtcga cgatcatgag 60
cggagaatta agggagtcac gttatgaccc ccgccgatga cgcgggacaa gccgttttac 120
gtttggaact gacagaaccg caacgttgaa ggagccactc agccgcgggt ttctggagtt 180
taatgagcta agcacatacg tcagaaacca ttattgcgcg ttcaaaagtc gcctaaggtc 240
actatcagct agcaaatatt tcttgtcaaa aatgctccac tgacgttcca taaattcccc 300

-continued

```
tcggtatcca attagagtct catattcact ctcaatccaa ataatctgca ccggatctgg    360
atcgtttcgc atgattgaac aagatggatt gcacgcaggt tctccggccg cttgggtgga    420
gaggctattc ggctatgact gggcacaaca gacaatcggc tgctctgatg ccgccgtgtt    480
ccggctgtca gcgcaggggc gcccggttct ttttgtcaag accgacctgt ccggtgccct    540
gaatgaactg caggacgagg cagcgcggct atcgtggctg gccacgacgg gcgttccttg    600
cgcagctgtg ctcgacgttg tcactgaagc gggaagggac tggctgctat tgggcgaagt    660
gccggggcag gatctcctgt catctcacct tgctcctgcc gagaaagtat ccatcatggc    720
tgatgcaatg cggcggctgc atacgcttga tccggctacc tgcccattcg accaccaagc    780
gaaacatcgc atcgagcgag cacgtactcg gatggaagcc ggtcttgtcg atcaggatga    840
tctggacgaa gagcatcagg ggctcgcgcc agccgaactg ttcgccaggc tcaaggcgcg    900
catgcccgac ggcgaggatc tcgtcgtgac ccatggcgat gcctgcttgc cgaatatcat    960
ggtggaaaat ggccgctttt ctggattcat cgactgtggc cggctgggtg tggcggaccg   1020
ctatcaggac atagcgttgg ctacccgtga tattgctgaa gagcttggcg gcgaatgggc   1080
tgaccgcttc ctcgtgcttt acggtatcgc cgctcccgat tcgcagcgca tcgccttcta   1140
tcgccttctt gacgagttct tctgagcggg actctggggt tcgaaatgac cgaccaagcg   1200
acgcccaacc tgccatcacg agatttcgat tccaccgccg ccttctatga aaggttgggc   1260
ttcggaatcg ttttccggga cgccggctgg atgatcctcc agcgcgggga tctcatgctg   1320
gagttcttcg cccacgggat ctctgcggaa caggcggtcg aaggtgccga tatcattacg   1380
acagcaacgg ccgacaagca caacgccacg atcctgagcg acaatatgat cgggcccggc   1440
gtccacatca acggcgtcgg cggcgactgc ccaggcaaga ccgagatgca ccgcgatatc   1500
ttgctgcgtt cggatatttt cgtggagttc ccgccacaga cccggatgat ccccgatcgt   1560
tcaaacattt ggcaataaag tttcttaaga ttgaatcctg ttgccggtct tgcgatgatt   1620
atcatataat ttctgttgaa ttacgttaag catgtaataa ttaacatgta atgcatgacg   1680
ttatttatga gatgggtttt tatgattaga gtcccgcaat tatacattta atacgcgata   1740
gaaaacaaaa tatagcgcgc aaactaggat aaattatcgc gcgcggtgtc atctatgtta   1800
ctagatcggg cctgcagggg gtccccacca ggtggtcgac ctcgagaaca tggtggagca   1860
cgacactctc gtctactcca agaatatcaa agatacagtc tcagaagacc aaagggctat   1920
tgagactttt caacaaaggg taatatcggg aaacctcctc ggattccatt gcccagctat   1980
ctgtcacttc atcaaaagga cagtagaaaa ggaaggtggc acctacaaat gccatcattg   2040
cgataaagga aaggctatcg ttcaagatgc ctctgccgac agtggtccca aagatggacc   2100
cccacccacg aggagcatcg tggaaaaaga agacgttcca accacgtctt caaagcaagt   2160
ggattgatgt gatatctcca ctgacgtaag ggatgacgca caatcccact atccttcgca   2220
agacccttcc tctatataag gaagttcatt tcatttggag aggaccctcg accaagcttc   2280
tagattagca atgaagagca agtatttgat tccataaaga gctgggcctt aaaccactcg   2340
gagtgcaaat taaatgtaat tagtggattg tttgcccaca tgtccatgaa agagcaagtt   2400
cgagcaatcc aagatgcttt tgtcattgtt ggtgctcatg gagcaggtct aacccacata   2460
gtttctgcag caccaaaagc tgtaatacta gaaattataa gcagcgaata taggcgcccc   2520
cattttgctc tgattgctca atggaaagga ttggagtacc atcccatata tttggagggg   2580
tcttatgcgg atccactgca cggtatgctc ctcttcttgt tcatggtcat gatccttata   2640
tgagcaggga aagtccagtt tagacttgta gttagttact cttcgttata ggatttggat   2700
```

```
ttcttgcgtg tttatggttt tagtttccct cctttgatga ataaaattga atcttgtatg   2760
agtttcatat ccatgttgtg aatctttttg cagacgcagc taggaccgca taagacccct   2820
ccaaatatat gggatggtac tccaatcctt tccattgagc aatcagagca aaatgggggc   2880
gcctatattc gctgcttata atttctagta ttacagcttt tggtgctgca gaaactatgt   2940
gggttagacc tgctccatga gcaccaacaa tgacaaaagc atcttggatt gctcgaactt   3000
gctctttcat ggacatgtgg gcaaacaatc cactaattac atttaatttg cactccgagt   3060
ggtttaaggc ccagctcttt atggaatcaa atacttgctc ttcattgcta atctagagct   3120
cgaccggtcg atgagctaag ctagctatat catcaattta tgtattacac ataatatcgc   3180
actcagtctt tcatctacgg caatgtacca gctgatataa tcagttattg aaatatttct   3240
gaatttaaac ttgcatcaat aaatttatgt tttgcttgg actataatac ctgacttgtt   3300
attttatcaa taaatattta aactatattt ctttcaagat actcgaggcg atcgcatacc   3360
agagaccggg taccactagt aacatggtgg agcacgacac tctcgtctac tccaagaata   3420
tcaaagatac agtctcagaa gaccaaaggg ctattgagac ttttcaacaa agggtaatat   3480
cgggaaacct cctcggattc cattgcccag ctatctgtca cttcatcaaa aggacagtag   3540
aaaaggaagg tggcacctac aaatgccatc attgcgataa aggaaaggct atcgttcaag   3600
atgcctctgc cgacagtggt cccaaagatg gacccccacc cacgaggagc atcgtggaaa   3660
aagaagacgt tccaaccacg tcttcaaagc aagtggattg atgtgatatc tccactgacg   3720
taagggatga cgcacaatcc cactatcctt cgcaagaccc ttcctctata taaggaagtt   3780
catttcattt ggagaggacg tacgccctcg accaagcttt agaggatcct tggcagcggc   3840
tttcatttct aattgtggtg ctcgcaactt ccgtttgcaa gctttagaag cccttgaaag   3900
ggcaaatatc agaattgact cttatggaag ttgtcatcat aacagggatg gaagagttga   3960
caaagtggca gcactgaagc gttaccagtt tagcctggct tttgggaatt ctaatgagga   4020
ggactatgta actgaaaaat tctttcagtc tctggtagct gggtcaatcc ctgtggtggt   4080
tggtgctcca aacatccaag actttgcgcc ttctcctaat tcagttttac acattaaaga   4140
gataaaagat gctgaatcaa ttgccaatac catgaagtac cttgctcaaa accctattgc   4200
atataatgag tcattaaggt ggaagtttga gggcccatct gatggatcca ctgcacggta   4260
tgctcctctt cttgttcatg gtcatgatcc ttatatgagc agggaaagtc cagtttagac   4320
ttgtagttag ttactcttcg ttataggatt tggatttctt gcgtgtttat ggttttagtt   4380
tccctccttt gatgaataaa attgaatctt gtatgagttt catatccatg ttgtgaatct   4440
ttttgcagac gcagctaggt ccggatccat cagatgggcc ctcaaacttc caccttaatg   4500
actcattata tgcaataggg ttttgagcaa ggtacttcat ggtattggca attgattcag   4560
catcttttat ctctttaatg tgtaaaactg aattaggaga aggcgcaaag tcttggatgt   4620
ttggagcacc aaccaccaca gggattgacc cagctaccag agactgaaag aatttttcag   4680
ttacatagtc ctcctcatta gaattcccaa aagccaggct aaactggtaa cgcttcagtg   4740
ctgccacttt gtcaactctt ccatccctgt tatgatgaca acttccataa gagtcaattc   4800
tgatatttgc cctttcaagg gcttctaaag cttgcaaacg gaagttgcga gcaccacaat   4860
tagaaatgaa agccgctgcc acgtacgcct aggcgatgag ctaagctagc tatatcatca   4920
atttatgtat tacacataat atcgcactca gtctttcatc tacggcaatg taccagctga   4980
tataatcagt tattgaaata tttctgaatt taaacttgca tcaataaatt tatgtttttg   5040
```

```
cttggactat aatacctgac ttgttatttt atcaataaat atttaaacta tatttcttc   5100
aagatactag ttgtacaatc gatggccggc cttaattaaa gattgtcgtt tcccgccttc   5160
agtttaaact aataacacat tgcggacgtt tttaatgtac tgattaatgg cgcgccgtcg   5220
acgatcatga gcggagaatt aagggagtca cgttatgacc cccgccgatg acgcgggaca   5280
agccgtttta cgtttggaac tgacagaacc gcaacgttga aggagccact cagccgcggg   5340
tttctggagt ttaatgagct aagcacatac gtcagaaacc attattgcgc gttcaaaagt   5400
cgcctaaggt cactatcagc tagcaaatat ttcttgtcaa aaatgctcca ctgacgttcc   5460
ataaattccc ctcggtatcc aattagagtc tcatattcac tctcaatcca aataatctgc   5520
accggatctg gatcgtttcg catgattgaa caagatggat tgcacgcagg ttctccggcc   5580
gcttgggtgg agaggctatt cggctatgac tgggcacaac agacaatcgg ctgctctgat   5640
gccgccgtgt tccggctgtc agcgcagggg cgcccggttc tttttgtcaa gaccgacctg   5700
tccggtgccc tgaatgaact gcaggacgag gcagcgcggc tatcgtggct ggccacgacg   5760
ggcgttcctt gcgcagctgt gctcgacgtt gtcactgaag cgggaaggga ctggctgcta   5820
ttgggcgaag tgccggggca ggatctcctg tcatctcacc ttgctcctgc cgagaaagta   5880
tccatcatgg ctgatgcaat gcggcggctg catacgcttg atccggctac ctgcccattc   5940
gaccaccaag cgaaacatcg catcgagcga gcacgtactc ggatggaagc cggtcttgtc   6000
gatcaggatg atctggacga agagcatcag gggctcgcgc cagccgaact gttcgccagg   6060
ctcaaggcgc gcatgcccga cggcgaggat ctcgtcgtga cccatggcga tgcctgcttg   6120
ccgaatatca tggtggaaaa tggccgcttt tctggattca tcgactgtgg ccggctgggt   6180
gtggcggacc gctatcagga catagcgttg gctacccgtg atattgctga agagcttggc   6240
ggcgaatggg ctgaccgctt cctcgtgctt tacggtatcg ccgctcccga ttcgcagcgc   6300
atcgccttct atcgccttct tgacgagttc ttctgagcgg gactctgggg ttcgaaatga   6360
ccgaccaagc gacgcccaac ctgccatcac gagatttcga ttccaccgcc gccttctatg   6420
aaaggttggg cttcggaatc gttttccggg acgccggctg gatgatcctc cagcgcgggg   6480
atctcatgct ggagttcttc gcccacggga tctctgcgga acaggcggtc gaaggtgccg   6540
atatcattac gacagcaacg gccgacaagc acaacgccac gatcctgagc gacaatatga   6600
tcgggcccgg cgtccacatc aacggcgtcg gcggcgactg cccaggcaag accgagatgc   6660
accgcgatat cttgctgcgt tcggatattt tcgtggagtt cccgccacag acccggatga   6720
tccccgatcg ttcaaacatt tggcaataaa gtttcttaag attgaatcct gttgccggtc   6780
ttgcgatgat tatcatataa tttctgttga attacgttaa gcatgtaata attaacatgt   6840
aatgcatgac gttatttatg agatgggttt ttatgattag agtcccgcaa ttatacattt   6900
aatacgcgat agaaaacaaa atatagcgcg caaactagga taaattatcg cgcgcggtgt   6960
catctatgtt actagatcgg gcctgcaggg ggtccccacc aggtggtcga cctcgagaac   7020
atggtggagc acgacactct cgtctactcc aagaatatca aagatacagt ctcagaagac   7080
caaagggcta ttgagacttt tcaacaaagg gtaatatcgg gaaacctcct cggattccat   7140
tgcccagcta tctgtcactt catcaaaagg acagtagaaa aggaaggtgg cacctacaaa   7200
tgccatcatt gcgataaagg aaaggctatc gttcaagatg cctctgccga cagtggtccc   7260
aaagatggac ccccacccac gaggagcatc gtggaaaaag aagacgttcc aaccacgtct   7320
tcaaagcaag tggattgatg tgatatctcc actgacgtaa gggatgacgc acaatcccac   7380
tatccttcgc aagacccttc ctctatataa ggaagttcat ttcatttgga gaggaccctc   7440
```

```
gaccaagctt ctagattagc aatgaagagc aagtatttga ttccataaag agctgggcct   7500
taaaccactc ggagtgcaaa ttaaatgtaa ttagtggatt gtttgcccac atgtccatga   7560
aagagcaagt tcgagcaatc caagatgctt ttgtcattgt tggtgctcat ggagcaggtc   7620
taacccacat agtttctgca gcaccaaaag ctgtaatact agaaattata agcagcgaat   7680
ataggcgccc ccattttgct ctgattgctc aatggaaagg attggagtac catcccatat   7740
atttggaggg gtcttatgcg gatccactgc acggtatgct cctcttcttg ttcatggtca   7800
tgatccttat atgagcaggg aaagtccagt ttagacttgt agttagttac tcttcgttat   7860
aggatttgga tttcttgcgt gtttatggtt ttagtttccc tcctttgatg aataaaattg   7920
aatcttgtat gagtttcata tccatgttgt gaatcttttt gcagacgcag ctaggaccgc   7980
ataagacccc tccaaatata tgggatggta ctccaatcct ttccattgag caatcagagc   8040
aaaatggggg cgcctatatt cgctgcttat aatttctagt attacagctt ttggtgctgc   8100
agaaactatg tgggttagac ctgctccatg agcaccaaca atgacaaaag catcttggat   8160
tgctcgaact tgctctttca tggacatgtg ggcaaacaat ccactaatta catttaattt   8220
gcactccgag tggtttaagg cccagctctt tatggaatca aatacttgct cttcattgct   8280
aatctagagc tcgaccggtc gatgagctaa gctagctata tcatcaattt atgtattaca   8340
cataatatcg cactcagtct ttcatctacg gcaatgtacc agctgatata atcagttatt   8400
gaaatatttc tgaatttaaa cttgcatcaa taaatttatg tttttgcttg gactataata   8460
cctgacttgt tattttatca ataaatattt aaactatatt tctttcaaga tactcgaggc   8520
gatcgcatac cagagaccgg gtaccactag taacatggtg gagcacgaca ctctcgtcta   8580
ctccaagaat atcaaagata cagtctcaga agaccaaagg gctattgaga cttttcaaca   8640
aagggtaata tcgggaaacc tcctcggatt ccattgccca gctatctgtc acttcatcaa   8700
aaggacagta gaaaaggaag gtggcaccta caaatgccat cattgcgata aaggaaaggc   8760
tatcgttcaa gatgcctctg ccgacagtgg tcccaaagat ggacccccac ccacgaggag   8820
catcgtggaa aaagaagacg ttccaaccac gtcttcaaag caagtggatt gatgtgatat   8880
ctccactgac gtaagggatg acgcacaatc ccactatcct tcgcaagacc cttcctctat   8940
ataaggaagt tcatttcatt tggagaggac gtacgccctc gaccaagctt tagaggatcc   9000
ttggcagcgg ctttcatttc taattgtggt gctcgcaact tccgtttgca agctttagaa   9060
gcccttgaaa gggcaaatat cagaattgac tcttatggaa gttgtcatca taacagggat   9120
ggaagagttg acaaagtggc agcactgaag cgttaccagt ttagcctggc ttttgggaat   9180
tctaatgagg aggactatgt aactgaaaaa ttctttcagt ctctggtagc tgggtcaatc   9240
cctgtggtgg ttggtgctcc aaacatccaa gactttgcgc cttctcctaa ttcagtttta   9300
cacattaaag agataaaaga tgctgaatca attgccaata ccatgaagta ccttgctcaa   9360
aaccctattg catataatga gtcattaagg tggaagtttg agggcccatc tgatggatcc   9420
actgcacggt atgctcctct tcttgttcat ggtcatgatc cttatatgag cagggaaagt   9480
ccagtttaga cttgtagtta gttactcttc gttataggat ttggatttct tgcgtgttta   9540
tggttttagt ttccctcctt tgatgaataa aattgaatct tgtatgagtt tcatatccat   9600
gttgtgaatc tttttgcaga cgcagctagg tccggatcca tcagatgggc cctcaaactt   9660
ccaccttaat gactcattat atgcaatagg gttttgagca aggtacttca tggtattggc   9720
aattgattca gcatctttta tctctttaat gtgtaaaact gaattaggag aaggcgcaaa   9780
```

```
gtcttggatg tttggagcac caaccaccac agggattgac ccagctacca gagactgaaa   9840
gaatttttca gttacatagt cctcctcatt agaattccca aaagccaggc taaactggta   9900
acgcttcagt gctgccactt tgtcaactct tccatccctg ttatgatgac aacttccata   9960
agagtcaatt ctgatatttg ccctttcaag ggcttctaaa gcttgcaaac ggaagttgcg  10020
agcaccacaa ttagaaatga aagccgctgc cacgtacgcc taggcgatga gctaagctag  10080
ctatatcatc aatttatgta ttacacataa tatcgcactc agtctttcat ctacggcaat  10140
gtaccagctg atataatcag ttattgaaat atttctgaat ttaaacttgc atcaataaat  10200
ttatgttttt gcttggacta taatacctga cttgttattt tatcaataaa tatttaaact  10260
atatttcttt caagatacta gttgtacaat cgatggccgg ccttaattaa agattgtcgt  10320
ttcccgcctt cagtttaaac ta                                           10342
```

<210> SEQ ID NO 16
<211> LENGTH: 10383
<212> TYPE: DNA
<213> ORGANISM: Artificial Sequence
<220> FEATURE:
<223> OTHER INFORMATION: Synthetic construct

<400> SEQUENCE: 16

```
tcaaacactg atagtttaaa ctgaaggcgg gaaacgacaa tctttaatta aggccggcca     60
tcgattgtac aactagtatc ttgaaagaaa tatagtttaa atatttattg ataaaataac    120
aagtcaggta ttatagtcca agcaaaaaca taaatttatt gatgcaagtt taaattcaga    180
aatatttcaa taactgatta tatcagctgg tacattgccg tagatgaaag actgagtgcg    240
atattatgtg taatacataa attgatgata tagctagctt agctcatcgc ctaggcgtac    300
gtggcagcgg ctttcatttc taattgtggt gctcgcaact tccgtttgca agctttagaa    360
gcccttgaaa gggcaaatat cagaattgac tcttatggaa gttgtcatca taacagggat    420
ggaagagttg acaaagtggc agcactgaag cgttaccagt ttagcctggc ttttgggaat    480
tctaatgagg aggactatgt aactgaaaaa ttctttcagt ctctggtagc tgggtcaatc    540
cctgtggtgg ttggtgctcc aaacatccaa gactttgcgc cttctcctaa ttcagtttta    600
cacattaaag agataaaaga tgctgaatca attgccaata ccatgaagta ccttgctcaa    660
aaccctattg catataatga gtcattaagg tggaagtttg agggcccatc tgatggatcc    720
ggacctagct gcgtctgcaa aaagattcac aacatggata tgaaactcat acaagattca    780
attttattca tcaaaggagg gaaactaaaa ccataaacac gcaagaaatc caaatcctat    840
aacgaagagt aactaactac aagtctaaac tggactttcc ctgctcatat aaggatcatg    900
accatgaaca agaagaggag cataccgtgc agtggatcca tcagatgggc cctcaaactt    960
ccaccttaat gactcattat atgcaatagg gttttgagca aggtacttca tggtattggc   1020
aattgattca gcatctttta tctctttaat gtgtaaaact gaattaggag aaggcgcaaa   1080
gtcttggatg tttggagcac caaccaccac agggattgac ccagctacca gagactgaaa   1140
gaatttttca gttacatagt cctcctcatt agaattccca aaagccaggc taaactggta   1200
acgcttcagt gctgccactt tgtcaactct tccatccctg ttatgatgac aacttccata   1260
agagtcaatt ctgatatttg ccctttcaag ggcttctaaa gcttgcaaac ggaagttgcg   1320
agcaccacaa ttagaaatga aagccgctgc caaggatcct ctaaagcttg gtcgagggcg   1380
tacgtcctct ccaaatgaaa tgaacttcct tatatagagg aagggtcttg cgaaggatag   1440
tgggattgtg cgtcatccct tacgtcagtg gagatatcac atcaatccac ttgctttgaa   1500
```

```
gacgtggttg gaacgtcttc tttttccacg atgctcctcg tgggtggggg tccatctttg   1560
ggaccactgt cggcagaggc atcttgaacg atagcctttc ctttatcgca atgatggcat   1620
ttgtaggtgc caccttcctt ttctactgtc cttttgatga agtgacagat agctgggcaa   1680
tggaatccga ggaggtttcc cgatattacc ctttgttgaa aagtctcaat agccctttgg   1740
tcttctgaga ctgtatcttt gatattcttg gagtagacga gagtgtcgtg ctccaccatg   1800
ttactagtgg tacccggtct ctggtatgcg atcgcctcga gtatcttgaa agaaatatag   1860
tttaaatatt tattgataaa ataacaagtc aggtattata gtccaagcaa aaacataaat   1920
ttattgatgc aagtttaaat tcagaaatat ttcaataact gattatatca gctggtacat   1980
tgccgtagat gaaagactga gtgcgatatt atgtgtaata cataaattga tgatatagct   2040
agcttagctc atcgaccggt cgagctctag attagcaatg aagagcaagt atttgattcc   2100
ataaagagct gggccttaaa ccactcggag tgcaaattaa atgtaattag tggattgttt   2160
gcccacatgt ccatgaaaga gcaagttcga gcaatccaag atgcttttgt cattgttggt   2220
gctcatggag caggtctaac ccacatagtt tctgcagcac caaaagctgt aatactagaa   2280
attataagca gcgaatatag gcgcccccat tttgctctga ttgctcaatg gaaaggattg   2340
gagtaccatc ccatatattt ggaggggtct tatgcggtcc tagctgcgtc tgcaaaaaga   2400
ttcacaacat ggatatgaaa ctcatacaag attcaatttt attcatcaaa ggagggaaac   2460
taaaaccata aacacgcaag aaatccaaat cctataacga agagtaacta actacaagtc   2520
taaactggac tttccctgct catataagga tcatgaccat gaacaagaag aggagcatac   2580
cgtgcagtgg atccgcataa gacccctcca aatatatggg atggtactcc aatcctttcc   2640
attgagcaat cagagcaaaa tgggggcgcc tatattcgct gcttataatt tctagtatta   2700
cagcttttgg tgctgcagaa actatgtggg ttagacctgc tccatgagca ccaacaatga   2760
caaaagcatc ttggattgct cgaacttgct ctttcatgga catgtgggca aacaatccac   2820
taattacatt taatttgcac tccgagtggt ttaaggccca gctctttatg gaatcaaata   2880
cttgctcttc attgctaatc tagaagcttg gtcgagggtc ctctccaaat gaaatgaact   2940
tccttatata gaggaagggt cttgcgaagg atagtgggat tgtgcgtcat cccttacgtc   3000
agtggagata tcacatcaat ccacttgctt tgaagacgtg gttggaacgt cttctttttc   3060
cacgatgctc ctcgtgggtg ggggtccatc tttgggacca ctgtcggcag aggcatcttg   3120
aacgatagcc tttcctttat cgcaatgatg gcatttgtag gtgccacctt ccttttctac   3180
tgtccttttg atgaagtgac agatagctgg gcaatggaat ccgaggaggt ttcccgatat   3240
taccctttgt tgaaaagtct caatagccct ttggtcttct gagactgtat ctttgatatt   3300
cttggagtag acgagagtgt cgtgctccac catgttctcg aggtcgacca cctggtgggg   3360
accccctgca ggcccgatct agtaacatag atgacaccgc gcgcgataat ttatcctagt   3420
ttgcgcgcta tattttgttt tctatcgcgt attaaatgta taattgcggg actctaatca   3480
taaaaaccca tctcataaat aacgtcatgc attacatgtt aattattaca tgcttaacgt   3540
aattcaacag aaattatatg ataatcatcg caagaccggc aacaggattc aatcttaaga   3600
aactttattg ccaaatgttt gaacgatcgg ggatcatccg ggtctgtggc gggaactcca   3660
cgaaaatatc cgaacgcagc aagatatcgc ggtgcatctc ggtcttgcct gggcagtcgc   3720
cgccgacgcc gttgatgtgg acgccgggcc cgatcatatt gtcgctcagg atcgtggcgt   3780
tgtgcttgtc ggccgttgct gtcgtaatga tatcggcacc ttcgaccgcc tgttccgcag   3840
```

```
agatcccgtg ggcgaagaac tccagcatga gatccccgcg ctggaggatc atccagccgg   3900
cgtcccggaa aacgattccg aagcccaacc tttcatagaa ggcggcggtg gaatcgaaat   3960
ctcgtgatgg caggttgggc gtcgcttggt cggtcatttc gaaccccaga gtcccgctca   4020
gaagaactcg tcaagaaggc gatagaaggc gatgcgctgc gaatcgggag cggcgatacc   4080
gtaaagcacg aggaagcggt cagcccattc gccgccaagc tcttcagcaa tatcacgggt   4140
agccaacgct atgtcctgat agcggtccgc cacacccagc cggccacagt cgatgaatcc   4200
agaaaagcgg ccattttcca ccatgatatt cggcaagcag gcatcgccat gggtcacgac   4260
gagatcctcg ccgtcgggca tgcgcgcctt gagcctggcg aacagttcgg ctggcgcgag   4320
cccctgatgc tcttcgtcca gatcatcctg atcgacaaga ccggcttcca tccgagtacg   4380
tgctcgctcg atgcgatgtt tcgcttggtg gtcgaatggg caggtagccg gatcaagcgt   4440
atgcagccgc cgcattgcat cagccatgat ggatactttc tcggcaggag caaggtgaga   4500
tgacaggaga tcctgccccg gcacttcgcc caatagcagc cagtcccttc ccgcttcagt   4560
gacaacgtcg agcacagctg cgcaaggaac gcccgtcgtg gccagccacg atagccgcgc   4620
tgcctcgtcc tgcagttcat tcagggcacc ggacaggtcg gtcttgacaa aaagaaccgg   4680
gcgcccctgc gctgacagcc ggaacacggc ggcatcagag cagccgattg tctgttgtgc   4740
ccagtcatag ccgaatagcc tctccaccca agcggccgga gaacctgcgt gcaatccatc   4800
ttgttcaatc atgcgaaacg atccagatcc ggtgcagatt atttggattg agagtgaata   4860
tgagactcta attggatacc gaggggaatt tatggaacgt cagtggagca tttttgacaa   4920
gaaatatttg ctagctgata gtgaccttag gcgacttttg aacgcgcaat aatggtttct   4980
gacgtatgtg cttagctcat taaactccag aaacccgcgg ctgagtggct ccttcaacgt   5040
tgcggttctg tcagttccaa acgtaaaacg gcttgtcccg cgtcatcggc gggggtcata   5100
acgtgactcc cttaattctc cgctcatgat cgtcgacggc gcgccattaa tcagtacatt   5160
aaaaacgtcc gcaatgtgtt attaagttgt ctaagcgtca atttgtttaa taacacattg   5220
cggacgtttt taatgtactg attaatggcg cgccgtcgac gatcatgagc ggagaattaa   5280
gggagtcacg ttatgacccc cgccgatgac gcgggacaag ccgttttacg tttggaactg   5340
acagaaccgc aacgttgaag gagccactca gccgcgggtt tctggagttt aatgagctaa   5400
gcacatacgt cagaaaccat tattgcgcgt tcaaaagtcg cctaaggtca ctatcagcta   5460
gcaaatattt cttgtcaaaa atgctccact gacgttccat aaattcccct cggtatccaa   5520
ttagagtctc atattcactc tcaatccaaa taatctgcac cggatctgga tcgtttcgca   5580
tgattgaaca agatggattg cacgcaggtt ctccggccgc ttgggtggag aggctattcg   5640
gctatgactg ggcacaacag acaatcggct gctctgatgc cgccgtgttc cggctgtcag   5700
cgcaggggcg cccggttctt tttgtcaaga ccgacctgtc cggtgccctg aatgaactgc   5760
aggacgaggc agcgcggcta tcgtggctgg ccacgacggg cgttccttgc gcagctgtgc   5820
tcgacgttgt cactgaagcg ggaagggact ggctgctatt gggcgaagtg ccggggcagg   5880
atctcctgtc atctcacctt gctcctgccg agaaagtatc catcatggct gatgcaatgc   5940
ggcggctgca tacgcttgat ccggctacct gcccattcga ccaccaagcg aaacatcgca   6000
tcgagcgagc acgtactcgg atggaagccg gtcttgtcga tcaggatgat ctggacgaag   6060
agcatcaggg gctcgcgcca gccgaactgt tcgccaggct caaggcgcgc atgcccgacg   6120
gcgaggatct cgtcgtgacc catggcgatg cctgcttgcc gaatatcatg gtggaaaatg   6180
gccgcttttc tggattcatc gactgtggcc ggctgggtgt ggcggaccgc tatcaggaca   6240
```

```
tagcgttggc tacccgtgat attgctgaag agcttggcgg cgaatgggct gaccgcttcc   6300
tcgtgcttta cggtatcgcc gctcccgatt cgcagcgcat cgccttctat cgccttcttg   6360
acgagttctt ctgagcggga ctctggggtt cgaaatgacc gaccaagcga cgcccaacct   6420
gccatcacga gatttcgatt ccaccgccgc cttctatgaa aggttgggct tcggaatcgt   6480
tttccgggac gccggctgga tgatcctcca gcgcggggat ctcatgctgg agttcttcgc   6540
ccacgggatc tctgcggaac aggcggtcga aggtgccgat atcattacga cagcaacggc   6600
cgacaagcac aacgccacga tcctgagcga caatatgatc gggcccggcg tccacatcaa   6660
cggcgtcggc ggcgactgcc caggcaagac cgagatgcac cgcgatatct tgctgcgttc   6720
ggatattttc gtggagttcc cgccacagac ccggatgatc cccgatcgtt caaacatttg   6780
gcaataaagt ttcttaagat tgaatcctgt tgccggtctt gcgatgatta tcatataatt   6840
tctgttgaat tacgttaagc atgtaataat taacatgtaa tgcatgacgt tatttatgag   6900
atgggttttt atgattagag tcccgcaatt atacatttaa tacgcgatag aaaacaaaat   6960
atagcgcgca aactaggata aattatcgcg cgcggtgtca tctatgttac tagatcgggc   7020
ctgcaggggg tccccaccag gtggtcgacc tcgagaacat ggtggagcac gacactctcg   7080
tctactccaa gaatatcaaa gatacagtct cagaagacca aagggctatt gagacttttc   7140
aacaaagggt aatatcggga aacctcctcg gattccattg cccagctatc tgtcacttca   7200
tcaaaaggac agtagaaaag gaaggtggca cctacaaatg ccatcattgc gataaaggaa   7260
aggctatcgt tcaagatgcc tctgccgaca gtggtcccaa agatggaccc ccacccacga   7320
ggagcatcgt ggaaaaagaa gacgttccaa ccacgtcttc aaagcaagtg gattgatgtg   7380
atatctccac tgacgtaagg gatgacgcac aatcccacta tccttcgcaa gacccttcct   7440
ctatataagg aagttcattt catttggaga ggaccctcga ccaagcttct agattagcaa   7500
tgaagagcaa gtatttgatt ccataaagag ctgggcctta aaccactcgg agtgcaaatt   7560
aaatgtaatt agtggattgt ttgcccacat gtccatgaaa gagcaagttc gagcaatcca   7620
agatgctttt gtcattgttg gtgctcatgg agcaggtcta acccacatag tttctgcagc   7680
accaaaagct gtaatactag aaattataag cagcgaatat aggcgccccc attttgctct   7740
gattgctcaa tggaaaggat tggagtacca tcccatatat ttggaggggt cttatgcgga   7800
tccactgcac ggtatgctcc tcttcttgtt catggtcatg atccttatat gagcagggaa   7860
agtccagttt agacttgtag ttagttactc ttcgttatag gatttggatt tcttgcgtgt   7920
ttatggtttt agtttccctc ctttgatgaa taaaattgaa tcttgtatga gtttcatatc   7980
catgttgtga atctttttgc agacgcagct aggaccgcat aagacccctc caaatatatg   8040
ggatggtact ccaatccttt ccattgagca atcagagcaa aatgggggcg cctatattcg   8100
ctgcttataa tttctagtat tacagctttt ggtgctgcag aaactatgtg ggttagacct   8160
gctccatgag caccaacaat gacaaaagca tcttggattg ctcgaacttg ctctttcatg   8220
gacatgtggg caaacaatcc actaattaca tttaatttgc actccgagtg gtttaaggcc   8280
cagctcttta tggaatcaaa tacttgctct tcattgctaa tctagagctc gaccggtcga   8340
tgagctaagc tagctatatc atcaatttat gtattacaca taatatcgca ctcagtcttt   8400
catctacggc aatgtaccag ctgatataat cagttattga aatatttctg aatttaaact   8460
tgcatcaata aatttatgtt tttgcttgga ctataatacc tgacttgtta ttttatcaat   8520
aaatatttaa actatatttc tttcaagata ctcgaggcga tcgcatacca gagaccgggt   8580
```

```
accactagta acatggtgga gcacgacact ctcgtctact ccaagaatat caaagataca   8640

gtctcagaag accaaagggc tattgagact tttcaacaaa gggtaatatc gggaaacctc   8700

ctcggattcc attgcccagc tatctgtcac ttcatcaaaa ggacagtaga aaaggaaggt   8760

ggcacctaca aatgccatca ttgcgataaa ggaaaggcta tcgttcaaga tgcctctgcc   8820

gacagtggtc ccaaagatgg acccccaccc acgaggagca tcgtggaaaa agaagacgtt   8880

ccaaccacgt cttcaaagca agtggattga tgtgatatct ccactgacgt aagggatgac   8940

gcacaatccc actatccttc gcaagaccct tcctctatat aaggaagttc atttcatttg   9000

gagaggacgt acgccctcga ccaagcttta gaggatcctt ggcagcggct ttcatttcta   9060

attgtggtgc tcgcaacttc cgtttgcaag ctttagaagc ccttgaaagg gcaaatatca   9120

gaattgactc ttatggaagt tgtcatcata acagggatgg aagagttgac aaagtggcag   9180

cactgaagcg ttaccagttt agcctggctt ttgggaattc taatgaggag gactatgtaa   9240

ctgaaaaatt ctttcagtct ctggtagctg ggtcaatccc tgtggtggtt ggtgctccaa   9300

acatccaaga ctttgcgcct tctcctaatt cagttttaca cattaaagag ataaaagatg   9360

ctgaatcaat tgccaatacc atgaagtacc ttgctcaaaa ccctattgca tataatgagt   9420

cattaaggtg gaagtttgag ggcccatctg atggatccac tgcacggtat gctcctcttc   9480

ttgttcatgg tcatgatcct tatatgagca gggaaagtcc agtttagact tgtagttagt   9540

tactcttcgt tataggattt ggatttcttg cgtgtttatg gttttagttt ccctcctttg   9600

atgaataaaa ttgaatcttg tatgagtttc atatccatgt tgtgaatctt tttgcagacg   9660

cagctaggtc cggatccatc agatgggccc tcaaacttcc accttaatga ctcattatat   9720

gcaatagggt tttgagcaag gtacttcatg gtattggcaa ttgattcagc atcttttatc   9780

tctttaatgt gtaaaactga attaggagaa ggcgcaaagt cttggatgtt tggagcacca   9840

accaccacag ggattgaccc agctaccaga gactgaaaga atttttcagt tacatagtcc   9900

tcctcattag aattcccaaa agccaggcta aactggtaac gcttcagtgc tgccactttg   9960

tcaactcttc catccctgtt atgatgacaa cttccataag agtcaattct gatatttgcc  10020

ctttcaaggg cttctaaagc ttgcaaacgg aagttgcgag caccacaatt agaaatgaaa  10080

gccgctgcca cgtacgccta ggcgatgagc taagctagct atatcatcaa tttatgtatt  10140

acacataata tcgcactcag tctttcatct acggcaatgt accagctgat ataatcagtt  10200

attgaaatat ttctgaattt aaacttgcat caataaattt atgtttttgc ttggactata  10260

atacctgact tgttatttta tcaataaata tttaaactat atttctttca agatactagt  10320

tgtacaatcg atggccggcc ttaattaaag attgtcgttt cccgccttca gtttaaacta  10380

tca                                                                10383
```

<210> SEQ ID NO 17
<211> LENGTH: 5033
<212> TYPE: DNA
<213> ORGANISM: Artificial Sequence
<220> FEATURE:
<223> OTHER INFORMATION: Synthetic construct

<400> SEQUENCE: 17

```
aaatcctata acgaagagta actaactaca agtctaaact ggactttccc tgctcatata     60

aggatcatga ccatgaacaa gaagaggagc ataccgtgca gtggatccgc ataagacccc    120

tccaaatata tgggatggta ctccaatcct ttccattgag caatcagagc aaaatggggg    180

cgcctatatt cgctgcttat aatttctagt attacagctt ttggtgctgc agaaactatg    240
```

```
tgggttagac ctgctccatg agcaccaaca atgacaaaag catcttggat tgctcgaact    300
tgctctttca tggacatgtg ggcaaacaat ccactaatta catttaattt gcactccgag    360
tggtttaagg cccagctctt tatggaatca aatacttgct cttcattgct aatctagagc    420
tcgaccggtc gatgagctaa gctagctata tcatcaattt atgtattaca cataatatcg    480
cactcagtct ttcatctacg gcaatgtacc agctgatata atcagttatt gaaatatttc    540
tgaatttaaa cttgcatcaa taaatttatg tttttgcttg gactataata cctgacttgt    600
tattttatca ataaatattt aaactatatt tctttcaaga tactcgaggc gatcgcatac    660
cagagaccgg gtaccactag taacatggtg gagcacgaca ctctcgtcta ctccaagaat    720
atcaaagata cagtctcaga agaccaaagg gctattgaga cttttcaaca aagggtaata    780
tcgggaaacc tcctcggatt ccattgccca gctatctgtc acttcatcaa aaggacagta    840
gaaaaggaag gtggcaccta caaatgccat cattgcgata aaggaaaggc tatcgttcaa    900
gatgcctctg ccgacagtgg tcccaaagat ggacccccac ccacgaggag catcgtggaa    960
aaagaagacg ttccaaccac gtcttcaaag caagtggatt gatgtgatat ctccactgac   1020
gtaagggatg acgcacaatc ccactatcct tcgcaagacc cttcctctat ataaggaagt   1080
tcatttcatt tggagaggac gtacgccctc gaccaagctt tagaggatcc ttggcagcgg   1140
ctttcatttc taattgtggt gctcgcaact tccgtttgca agctttagaa gcccttgaaa   1200
gggcaaatat cagaattgac tcttatggaa gttgtcatca taacagggat ggaagagttg   1260
acaaagtggc agcactgaag cgttaccagt ttagcctggc ttttgggaat tctaatgagg   1320
aggactatgt aactgaaaaa ttctttcagt ctctggtagc tgggtcaatc cctgtggtgg   1380
ttggtgctcc aaacatccaa gactttgcgc cttctcctaa ttcagtttta cacattaaag   1440
agataaaaga tgctgaatca attgccaata ccatgaagta ccttgctcaa aaccctattg   1500
catataatga gtcattaagg tggaagtttg agggcccatc tgatggatcc actgcacggt   1560
atgctcctct tcttgttcat ggtcatgatc cttatatgag cagggaaagt ccagtttaga   1620
cttgtagtta gttactcttc gttataggat ttggatttct tgcgtgttta tggttttagt   1680
ttccctcctt tgatgaataa aattgaatct tgtatgagtt tcatatccat gttgtgaatc   1740
tttttgcaga cgcagctagg tccggatcca tcagatgggc cctcaaactt ccaccttaat   1800
gactcattat atgcaatagg gttttgagca aggtacttca tggtattggc aattgattca   1860
gcatctttta tctctttaat gtgtaaaact gaattaggag aaggcgcaaa gtcttggatg   1920
tttggagcac caaccaccac agggattgac ccagctacca gagactgaaa gaatttttca   1980
gttacatagt cctcctcatt agaattccca aaagccaggc taaactggta acgcttcagt   2040
gctgccactt tgtcaactct tccatccctg ttatgatgac aacttccata agagtcaatt   2100
ctgatatttg ccctttcaag ggcttctaaa gcttgcaaac ggaagttgcg agcaccacaa   2160
ttagaaatga aagccgctgc cacgtacgcc taggcgatga gctaagctag ctatatcatc   2220
aatttatgta ttacacataa tatcgcactc agtctttcat ctacggcaat gtaccagctg   2280
atataatcag ttattgaaat atttctgaat ttaaacttgc atcaataaat ttatgttttt   2340
gcttggacta taatacctga cttgttattt tatcaataaa tatttaaact atatttcttt   2400
caagatacta gttgtacaat cgatggccgg ccttaattaa agattgtcgt ttcccgcctt   2460
cagtttaaac tatcagtgtt tgaatggata tgaaactcat acaagattca attttattca   2520
tcaaaggagg gaaactaaaa ccataaacac gcaagaaatc caaatcctat aacgaagagt   2580
```

-continued

```
aactaactac aagtctaaac tggactttcc ctgctcatat aaggatcatg accatgaaca   2640
agaagaggag cataccgtgc agtggatccg cataagaccc ctccaaatat atgggatggt   2700
actccaatcc tttccattga gcaatcagag caaaatgggg gcgcctatat tcgctgctta   2760
taatttctag tattacagct tttggtgctg cagaaactat gtgggttaga cctgctccat   2820
gagcaccaac aatgacaaaa gcatcttgga ttgctcgaac ttgctctttc atggacatgt   2880
gggcaaacaa tccactaatt acatttaatt tgcactccga gtggtttaag gcccagctct   2940
ttatggaatc aaatacttgc tcttcattgc taatctagag ctcgaccggt cgatgagcta   3000
agctagctat atcatcaatt tatgtattac acataatatc gcactcagtc tttcatctac   3060
ggcaatgtac cagctgatat aatcagttat tgaaatattt ctgaatttaa acttgcatca   3120
ataaatttat gtttttgctt ggactataat acctgacttg ttattttatc aataaatatt   3180
taaactatat ttctttcaag atactcgagg cgatcgcata ccagagaccg ggtaccacta   3240
gtaacatggt ggagcacgac actctcgtct actccaagaa tatcaaagat acagtctcag   3300
aagaccaaag ggctattgag acttttcaac aaagggtaat atcgggaaac ctcctcggat   3360
tccattgccc agctatctgt cacttcatca aaaggacagt agaaaaggaa ggtggcacct   3420
acaaatgcca tcattgcgat aaaggaaagg ctatcgttca agatgcctct gccgacagtg   3480
gtcccaaaga tggaccccca cccacgagga gcatcgtgga aaaagaagac gttccaacca   3540
cgtcttcaaa gcaagtggat tgatgtgata tctccactga cgtaagggat gacgcacaat   3600
cccactatcc ttcgcaagac ccttcctcta tataaggaag ttcatttcat ttggagagga   3660
cgtacgccct cgaccaagct ttagaggatc cttggcagcg gctttcattt ctaattgtgg   3720
tgctcgcaac ttccgtttgc aagctttaga agcccttgaa agggcaaata tcagaattga   3780
ctcttatgga agttgtcatc ataacaggga tggaagagtt gacaaagtgg cagcactgaa   3840
gcgttaccag tttagcctgg cttttgggaa ttctaatgag gaggactatg taactgaaaa   3900
attctttcag tctctggtag ctgggtcaat ccctgtggtg gttggtgctc caaacatcca   3960
agactttgcg ccttctccta attcagtttt acacattaaa gagataaaag atgctgaatc   4020
aattgccaat accatgaagt accttgctca aaaccctatt gcatataatg agtcattaag   4080
gtggaagttt gagggcccat ctgatggatc cactgcacgg tatgctcctc ttcttgttca   4140
tggtcatgat ccttatatga gcagggaaag tccagtttag acttgtagtt agttactctt   4200
cgttatagga tttggatttc ttgcgtgttt atggttttag tttccctcct ttgatgaata   4260
aaattgaatc ttgtatgagt ttcatatcca tgttgtgaat ctttttgcag acgcagctag   4320
gtccggatcc atcagatggg ccctcaaact tccaccttaa tgactcatta tatgcaatag   4380
ggttttgagc aaggtacttc atggtattgg caattgattc agcatctttt atctctttaa   4440
tgtgtaaaac tgaattagga gaaggcgcaa agtcttggat gtttggagca ccaaccacca   4500
cagggattga cccagctacc agagactgaa agaatttttc agttacatag tcctcctcat   4560
tagaattccc aaaagccagg ctaaactggt aacgcttcag tgctgccact ttgtcaactc   4620
ttccatccct gttatgatga caacttccat aagagtcaat tctgatattt gccctttcaa   4680
gggcttctaa agcttgcaaa cggaagttgc gagcaccaca attagaaatg aaagccgctg   4740
ccacgtacgc ctaggcgatg agctaagcta gctatatcat caatttatgt attacacata   4800
atatcgcact cagtctttca tctacggcaa tgtaccagct gatataatca gttattgaaa   4860
tatttctgaa tttaaacttg catcaataaa tttatgtttt tgcttggact ataatacctg   4920
acttgttatt ttatcaataa atatttaaac tatatttctt tcaagatact agttgtacaa   4980
```

tcgatggccg gccttaatta aagattgtcg tttcccgcct tcagtttaaa cta 5033

<210> SEQ ID NO 18
<211> LENGTH: 86
<212> TYPE: DNA
<213> ORGANISM: Artificial Sequence
<220> FEATURE:
<223> OTHER INFORMATION: Synthetic construct

<400> SEQUENCE: 18
acttacaaat ttagtttcat acttaatgat aaagctactt ttaattagct tagtttaaac 60
tgaaggcggg aaacgacaat ctttaa 86

<210> SEQ ID NO 19
<211> LENGTH: 50
<212> TYPE: DNA
<213> ORGANISM: Artificial Sequence
<220> FEATURE:
<223> OTHER INFORMATION: Synthetic construct

<400> SEQUENCE: 19
acttacaaat ttagtttcat acttaatgat aaagctactt ttaattagct 50

<210> SEQ ID NO 20
<211> LENGTH: 18
<212> TYPE: DNA
<213> ORGANISM: Artificial Sequence
<220> FEATURE:
<223> OTHER INFORMATION: Synthetic construct

<400> SEQUENCE: 20
ttaattaagg ccggccat 18

<210> SEQ ID NO 21
<211> LENGTH: 14
<212> TYPE: DNA
<213> ORGANISM: Artificial Sequence
<220> FEATURE:
<223> OTHER INFORMATION: Synthetic construct

<400> SEQUENCE: 21
tcgacggcgc gcca 14

<210> SEQ ID NO 22
<211> LENGTH: 51
<212> TYPE: DNA
<213> ORGANISM: Artificial Sequence
<220> FEATURE:
<223> OTHER INFORMATION: Synthetic construct

<400> SEQUENCE: 22
aagtcaaata tgctctagta gtagacttgt ccaaagtcta tataaccaat c 51

<210> SEQ ID NO 23
<211> LENGTH: 86
<212> TYPE: DNA
<213> ORGANISM: Artificial Sequence
<220> FEATURE:
<223> OTHER INFORMATION: Synthetic construct

<400> SEQUENCE: 23
ttaatcagta cattaaaaac gtccgcaatg tgttattaaa tgaacatgtg gtatagaaaa 60
tgtcattcat ttttctttta aacata 86

<210> SEQ ID NO 24
<211> LENGTH: 50
<212> TYPE: DNA
<213> ORGANISM: Artificial Sequence
<220> FEATURE:
<223> OTHER INFORMATION: Synthetic construct

<400> SEQUENCE: 24
taaatgaaca tgtggtatag aaaatgtcat tcatttttct tttaaacata 50

<210> SEQ ID NO 25
<211> LENGTH: 86
<212> TYPE: DNA
<213> ORGANISM: Artificial Sequence
<220> FEATURE:
<223> OTHER INFORMATION: Synthetic construct

<400> SEQUENCE: 25
cttatgtcta atttcaactt tgattatttt tcacgttttt tctttaacct tcaaacactg 60
atagtttaaa ctgaaggcgg gaaacg 86

<210> SEQ ID NO 26
<211> LENGTH: 50
<212> TYPE: DNA
<213> ORGANISM: Artificial Sequence
<220> FEATURE:
<223> OTHER INFORMATION: Synthetic construct

<400> SEQUENCE: 26
cttatgtcta atttcaactt tgattatttt tcacgttttt tctttaacct 50

<210> SEQ ID NO 27
<211> LENGTH: 14
<212> TYPE: DNA
<213> ORGANISM: Artificial Sequence
<220> FEATURE:
<223> OTHER INFORMATION: Synthetic construct

<400> SEQUENCE: 27
acaatcttta atta 14

<210> SEQ ID NO 28
<211> LENGTH: 14
<212> TYPE: DNA
<213> ORGANISM: Artificial Sequence
<220> FEATURE:
<223> OTHER INFORMATION: Synthetic construct

<400> SEQUENCE: 28
gccggcctta atta 14

<210> SEQ ID NO 29
<211> LENGTH: 29
<212> TYPE: DNA
<213> ORGANISM: Artificial Sequence
<220> FEATURE:
<223> OTHER INFORMATION: Synthetic construct

<400> SEQUENCE: 29
tttgtttttg gtacgttcag attgctttc 29

<210> SEQ ID NO 30
<211> LENGTH: 86
<212> TYPE: DNA
<213> ORGANISM: Artificial Sequence
<220> FEATURE:
<223> OTHER INFORMATION: Synthetic construct

<400> SEQUENCE: 30
aagattgtcg tttcccgcct tcagtttaaa ctatcacaag ttctagtcaa agcattgatt 60
ggaatagatc aaggtgacca attgga 86

<210> SEQ ID NO 31
<211> LENGTH: 50
<212> TYPE: DNA
<213> ORGANISM: Artificial Sequence
<220> FEATURE:
<223> OTHER INFORMATION: Synthetic construct

<400> SEQUENCE: 31
caagttctag tcaaagcatt gattggaata gatcaaggtg accaattgga 50

<210> SEQ ID NO 32
<211> LENGTH: 86
<212> TYPE: DNA
<213> ORGANISM: Artificial Sequence
<220> FEATURE:
<223> OTHER INFORMATION: Synthetic construct

<400> SEQUENCE: 32
gattgggaca aaaaatctgg tgaatctggg agcaaagagt cagctggttg tagtttaaac 60
tgaaggcggg aaacgacaat ctttaa 86

<210> SEQ ID NO 33
<211> LENGTH: 50
<212> TYPE: DNA
<213> ORGANISM: Artificial Sequence
<220> FEATURE:
<223> OTHER INFORMATION: Synthetic cosntruct

<400> SEQUENCE: 33
gattgggaca aaaaatctgg tgaatctggg agcaaagagt cagctggttg 50

<210> SEQ ID NO 34
<211> LENGTH: 14
<212> TYPE: DNA
<213> ORGANISM: Artificial Sequence
<220> FEATURE:
<223> OTHER INFORMATION: Synthetic construct

<400> SEQUENCE: 34
ttaaggccgg ccat 14

<210> SEQ ID NO 35
<211> LENGTH: 14
<212> TYPE: DNA
<213> ORGANISM: Artificial Sequence
<220> FEATURE:
<223> OTHER INFORMATION: Synthetic construct

<400> SEQUENCE: 35
gggaaagtcc agtt 14

<210> SEQ ID NO 36
<211> LENGTH: 67
<212> TYPE: DNA
<213> ORGANISM: Artificial Sequence
<220> FEATURE:
<223> OTHER INFORMATION: Synthetic construct -continued

```
<400> SEQUENCE: 36

ggacaacaag atcactcaga aagcgtcagc aggaaactcc tctgcatgga atagcaaatc     60

tgcagtc                                                               67


<210> SEQ ID NO 37
<211> LENGTH: 86
<212> TYPE: DNA
<213> ORGANISM: Artificial Sequence
<220> FEATURE:
<223> OTHER INFORMATION: Synthetic construct

<400> SEQUENCE: 37

tagacttgta gttagttact cttcgttata ggatttgaac aagatgccaa tgggaaaaat     60

caatggagtg gtaaaagaac ttcaga                                          86


<210> SEQ ID NO 38
<211> LENGTH: 50
<212> TYPE: DNA
<213> ORGANISM: Artificial Sequence
<220> FEATURE:
<223> OTHER INFORMATION: Synthetic construct

<400> SEQUENCE: 38

gaacaagatg ccaatgggaa aaatcaatgg agtggtaaaa gaacttcaga                50
```